(12) United States Patent
Roux et al.

(10) Patent No.: US 9,108,919 B2
(45) Date of Patent: Aug. 18, 2015

(54) COMPOUNDS USEFUL FOR TREATING CANCER

(71) Applicants: CENTRE NATIONALE DE RECHERCHE SCIENTIFIQUE, Paris (FR); INSTITUT CURIE, Paris (FR); SOCIETE SPLICOS, Montpellier (FR); UNIVERSITE MONTPELLIER 2, Montpellier (FR)

(72) Inventors: Pierre Roux, Saint-Gely-du-Fesc (FR); Florence Mahuteau, Saint Remy les Chevreuse (FR); Romain Najman, L'Hay les Roses (FR); Jamal Tazi, Clapiers (FR); Gilles Gadea, Matelles (FR); Didier Scherrer, Castelnau le Lez (FR); Carsten Brock, Montpellier (FR); Nathalie Cahuzac, Jacou (FR)

(73) Assignees: ABIVAX, Paris (FR); CENTRE NATIONALE DE RECHERCHE SCIENTIFIQUE, Paris (FR); INSTITUT CURIE, Paris (FR); UNIVERSITE MONTPELLIER 2, Montpellier (FR)

(*) Notice: Subject to any disclaimer, the term of this patent is extended or adjusted under 35 U.S.C. 154(b) by 0 days.

(21) Appl. No.: 14/087,762

(22) Filed: Nov. 22, 2013

(65) Prior Publication Data

US 2014/0080831 A1 Mar. 20, 2014

Related U.S. Application Data

(63) Continuation of application No. 13/377,745, filed as application No. PCT/IB2010/052650 on Jun. 14, 2010, now abandoned.

(60) Provisional application No. 61/186,552, filed on Jun. 12, 2009, provisional application No. 61/186,544, filed on Jun. 12, 2009.

(30) Foreign Application Priority Data

Jun. 12, 2009 (EP) .................................... 09162630
Jun. 12, 2009 (EP) .................................... 09305540

(51) Int. Cl.
C07D 401/12 (2006.01)
A61K 31/47 (2006.01)
C07D 215/42 (2006.01)
C07D 213/74 (2006.01)
C07D 215/38 (2006.01)
C07D 241/44 (2006.01)
C07D 403/12 (2006.01)
C07D 215/46 (2006.01)

(52) U.S. Cl.
CPC ............ *C07D 215/42* (2013.01); *C07D 213/74* (2013.01); *C07D 215/38* (2013.01); *C07D 215/46* (2013.01); *C07D 241/44* (2013.01); *C07D 401/12* (2013.01); *C07D 403/12* (2013.01)

(58) Field of Classification Search
None
See application file for complete search history.

(56) References Cited

U.S. PATENT DOCUMENTS

| 7,019,147 B1 | 3/2006 | Barth et al. |
| 2004/0038969 A1 | 2/2004 | Doherty et al. |
| 2005/0119225 A1 | 6/2005 | Schumacher et al. |
| 2006/0089380 A1 | 4/2006 | Barnham et al. |

(Continued)

FOREIGN PATENT DOCUMENTS

| EP | 0 394 112 A2 | 10/1990 |
| FR | 2 387 229 A1 | 11/1978 |
| FR | 2 436 786 A1 | 4/1980 |

(Continued)

OTHER PUBLICATIONS

El-Sayed et al., "Synthesis of Some Novel Quinoline-3-carboxylic Acids and Pyrimidoquinoline Derivatives as Potential Antimicrobial Agents", Archiv der Pharmize, 2002, pp. 403-410, vol. 335(9).
Silberg et al., "N-Acyl-N, N-dipyridyl and N-acyl-N-pyridyl-N-quinoyl amine based palladium complexes. Synthesis, X-ray structures, heterogenization and use in Heck couplings", Journal of Organmetallic Chemistry, 2001, pp. 6-18, vol. 622.
File Registry on STN, 195876-33-6/RN, entered on Oct. 23, 1997.
File Registry on STN, 70125-24-5/RN, entered on Nov. 16, 1984.
Aug. 15, 2014 Office Action issued in U.S. Appl. No. 13/377,753.
Jun. 27, 2014 Office Action issued in U.S. Appl. No. 13/993,990.
Jul. 18, 2014 Office Action issued in U.S. Appl. No. 13/377,760.

(Continued)

Primary Examiner — Zinna Northington Davis
(74) Attorney, Agent, or Firm — Oliff PLC

(57) ABSTRACT

A method of preventing, inhibiting, or treating cancer that includes contacting a cell with at least one compound of formula (Ia) or a pharmaceutically acceptable salt thereof:

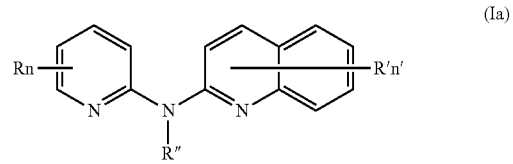

(Ia)

where:
R independently represents a hydrogen atom, a halogen atom, a $(C_1-C_3)$alkyl group, a —CN group, a hydroxyl group, a —COOR$_1$ group, a $(C_1-C_3)$fluoroalkyl group, a —NO$_2$ group, a —NR$_1$R$_2$ group, or a $(C_1-C_3)$alkoxy group;
R' is a hydrogen atom, a halogen atom, a $(C_1-C_3)$alkyl group, a —NO$_2$ group, a $(C_1-C_3)$alkoxy group, or a —NR$_1$R$_2$ group; and
R$_1$ and R$_2$ are a hydrogen atom or a $(C_1-C_3)$alkyl group.

10 Claims, No Drawings

(56) References Cited

U.S. PATENT DOCUMENTS

| | | |
|---|---|---|
| 2008/0161353 A1 | 7/2008 | Barnham et al. |
| 2011/0003843 A1 | 1/2011 | Lejeune et al. |

FOREIGN PATENT DOCUMENTS

| | | |
|---|---|---|
| FR | 2 627 493 A1 | 8/1989 |
| FR | 2 645 861 A1 | 10/1990 |
| FR | 2 849 474 A1 | 3/2005 |
| FR | 2 859 475 A1 | 3/2005 |
| WO | WO 00/59875 | 10/2000 |
| WO | WO 2004/007461 A1 | 1/2004 |
| WO | WO 2004/078731 A1 | 9/2004 |
| WO | WO 2005/023255 A2 | 3/2005 |
| WO | WO 2006/081444 A2 | 8/2006 |
| WO | WO 2008/003864 A1 | 1/2008 |
| WO | WO 2008/008234 A1 | 1/2008 |
| WO | WO 2008/101935 A2 | 8/2008 |
| WO | WO 2008/115870 A2 | 9/2008 |
| WO | WO 2008/143440 A1 | 11/2008 |
| WO | WO 2009/023844 A2 | 2/2009 |
| WO | WO 2009/087238 A2 | 7/2009 |
| WO | WO 2010/143168 A2 | 12/2010 |
| WO | WO 2010/143169 A2 | 12/2010 |

OTHER PUBLICATIONS

Brandt et al., "Uncoupling activity and physicochemical properties of derivatives of fluazinam," Biochimica et Biophysica Acta, Protein Structure and Molecular Enzymology, 1101(1): 41-7, 1992, abstract only CA 117:82915.

Perry et al., "AIDS dementia: a review of the literature," Alzheimer Dis. Assoc. Disord. 1(4): 221-235 (1987) (PubMed Abstract 3331119).

Pauwels, "Aspects of successful drug discovery and development," Antiviral Res. 71: 77-89 (2006).

Respess et al., "Evaluation of an Ultrasensitive p24 Antigen Assay as a Potential Alternative to Human Immunodeficiency Virus Type 1 RNA Viral Load Assay in Resource-Limited Settings," J. Clin. Microbiol. 43(1): 506-08 (2005).

Jun. 27, 2011 International Search Report issued in International Patent Application No. PCT/IB2010/052652.

Jun. 27, 2011 Written Opinion of the International Searching Authority issued in International Patent Application No. PCT/IB2010/052652.

Aug. 9, 2011 International Search Report issued in International Patent Application No. PCT/IB2010/052651.

Aug. 9, 2011 Written Opinion of the International Searching Authority issued in International Patent Application No. PCT/IB2010/052651.

Apr. 13, 2011 International Search Report issued in International Patent Application No. PCT/IB2010/052650.

Apr. 13, 2011 Written Opinion of the International Searching Authority issued in International Patent Application No. PCT/IB2010/052650.

Dec. 10, 2009 Partial European Search Report issued in European Patent Application No. 09162630.9.

Nov. 19, 2009 European Search Report issued in European Patent Application No. 09305540.

Vulliamy et al., "Mutations in the Telomerase Component NHP2 Cause the Premature Ageing Syndrome Dyskeratosis Congenita," PNAS, 2008, vol. 105, No. 23, pp. 8073-8078.

Brune et al., "Progeria: A New Kind of Laminopathy—Clinical and Molecular Update of the Hutchinson-Gilford Syndrome," 1$^{st}$ European Symposium, 2003.

Park et al., "Efficient Palladium-Catalyzed Amination of Aryl Chlorides Using Dicyclo-hexylamino[(2,6-dimethyl)morpholino]phenylphosphine as a PN$_2$ Ligand," Synthesis, 2009, No. 5, pp. 0815-0823.

Loones et al., "Examination of the Mechanism of the Intramolecular Amination of N-(3-bromopyridin- 2-yl) azaheteroarylamines and N-(2-chloropyridin-3-yl)azaheteroarylamines: a Pd-catalyzed Amination and/or a Base-Assisted Nucleophilic Aromatic Substitution?," Tetrahedron, 2007, vol. 63, pp. 3818-3825.

Dhanabal et al., "Heteroatom Directed Photoannulation: Synthesis of Indoloquinoline Alkaloids: Cryptolepine, Cryptotackieine, Cryptosanguinolentine, and their Methyl Derivatives," Tetrahedron, 2006, vol. 62, pp. 6258-6263.

Boganyi et al.,"Syntheses of New Quinoline-Containing Heterocyclic Scaffolds Using Inter- and Intramolecular Pd-Catalyzed Amination," Journal of Heterocyclic Chemistry, 2009, vol. 46, No. 1, pp. 33-38.

Fors et al., "An Efficient Process for Pd-Catalyzed C-N Cross-Coupling Reactions of Aryl Iodides: Insight Into Controlling Factors," Journal of the American Chemical Society, 2009, vol. 131, No. 16, 5766-5768.

Jonckers et al., "Selective Palladium-Catalyzed Aminations of Dicholoropyridines," Tetrahedron, 2001, vol. 57, pp. 7027-7034.

Kaczmarek et al., "Synthesis and Antineoplastic Properties of Some Benzoiso-.Alpha.-Carbolines," Archiv Der Pharmazie, Weinheim, Germany, 1998, vol. 321, No. 8, pp. 463-467.

Loones et al., "Synthesis of Pyrido[2', 1':2,3]imidazo[4,5-b]quinoline and pyrido[1',2':1,2]imidazo [4,5b]quinoline and their Benzo and Aza Analogs via Tandem Catalysis," Tetrahedron, 2007, vol. 63, pp. 8954-8961.

Solekhova et al., "Reductive Amination of Quinoline N-Oxide with Aminopyridines and their N-Tosyl Derivatives," Russian Journal of Organic Chemistry, 2002, vol. 38, No. 8, pp. 1192-1194.

Nguyen et al., "Synthesis and Biological Evaluation of Amino-Substituted Benzo [f]pyrido[4,3-b] and Pyrido [3,4-b]quinoxalines: a New Class of Antineoplastic Agents," Anti-Cancer Drug Design, 1995, vol. 10, No. 4, 277-97 (abstract only).

Baklanov et al., "Photocyclization of (o-haloaryl)hetarylamines," Zhurnal Organicheskoi Khimii, 1991, vol. 27, No. 3, pp. 638-649 (abstract only).

Ducrocq et al., "Synthesis of 10-substituted 5H-pyrido[3', 4':4,5]pyrrolo[2,3-]isoquinolines," Journal of the Chemical Society, Perkin Transactions 1: Organic and Bio-Organic Chemistry (1972-1999), 1979, vol. 1, pp. 142-145.

Prostakov et al., "Schiff Bases in Syntheses of Substituted Naphthylamines, Napthyridines, Azophenanthrenes, and Benzocarbazole," Khimiya Geterotsiklicheskikh Soedinenii, 1972, vol. 10, pp. 1400-1403 (abstract only).

Grout et al., "Polyazabenzo[a]pyrenes," Journal of the Chemical Society [Section] C: Organic, 1968, vol. 21, pp. 2689-2693.

Talik et al., "2-Chloro-3, 5-dinitropyridine. I. Exchange Reactions of the Chlorine Atom," Bulletin de L'Academie Polonaise des Sciences, Serie Des Sciences Chimiques, 1960, vol. 8, No. 5, pp. 219-222 (abstract only).

Deuerleine, "Dipryridyl-, diquinolyl-, and Pyridylquinolylamines," Journal fuer Praktische Chemie (Liepzig), 1923, vol. 106, pp. 53-65 (abstract only).

Kondratenko et al., "Bactericidal Activity of Some Derivatives of N-heteroaromatic Compounds," Mikrobiologichnii Zhurnal, 1934-1977, 1978, vol. 40, No. 3, pp. 368-370 (abstract only).

Gritsenko et al., "Synthesis in Phenothiazines. XXXIX. Dimethylpyridophenothiazines," Khimiya Geterotsiklicheskikh Soedinenii,1975, vol. 1, pp. 50-54 (abstract only).

Buchmann et al., "The Preparation and Reactivity of 4-hydroxy-7-chloroquinaldine," Journal fuer Praktische Chemie, 1962, vol. 17, pp. 135-146 (abstract only).

Khalifa, "Hutchinson-Gilford Progeria Syndrome: Report of a Libyan Family and Evidence of Autosomal Recessive Inheritance," Clinical Genetics, 1989, vol. 35, pp. 125-132.

De Sandre-Giovannoli et al., "Lamin A Truncation in Hutchinson-Gilford Progeria," Science, 2003, vol. 300, p. 2055.

Pendas et al., "Defective Prelamin A Processing and Muscular and Adipocyte Alterations in Zmpste24 Metalloproteinsase-deficient Mice," Nature Genetics, 2002, vol. 31, pp. 94-99.

De Sandre-Giovannoli et al., "Altered Splicing in Prelamin A-associated Premature Aging Phenotypes," Progress in Molecular and Subcellular Biology, 2006, pp. 199-232.

(56) References Cited

OTHER PUBLICATIONS

Fong et al., "A Protein Farnesyltransferase Inhibitor Ameliorates Disease in a Mouse Model of Progeria," Science, 2006, vol. 311, pp. 1621-1623.

Varela et al., "Combined Treatment with Statins and Aminobisphosphonates Extends Longevity in a Mouse Model of Human Premature Aging," Nature Medicine, 2008, vol. 14, No. 7, pp. 767-772.

Labourier et al., "Recognition of Exonic Splicing Enhancer Sequences by the Drosophila Splicing Repressor RSF1," Nucleic Acids Research, 1999, vol. 27, No. 11, pp. 2377-2386.

Dignam et al., "Eukaryotic Gene Transcription with Purified Components," Methods in Enzymology, 1983, vol. 101, pp. 582-598.

Tazi et al., "A Protein that Specifically Recognizes the 3' Splice Site of Mammalian Pre-mRNA Introns is Associated with a Small Nuclear Ribonucleoprotein," Cell, 1986, vol. 47, pp. 755-766.

Sanchez-Martin et al., "Symmetrical Bis-Quinolinium Compounds: New Human Choline Kinase Inhibitors with Antiproliferative Activity against the HT-29 Cell Line," Journal of Medicinal Chemistry, 2005, vol. 48, No. 9 pp. 3354-3363.

Cottet et al., "Recommendable Routes to Trifluoromethyl-Substituted Pyridine-and Quinolinecarboxylic Acids," Eur. J. Org. Chem., 2003, pp. 1559-1568.

Balkau et al., "Synthesis of Ellipticine Intermediates: 6-Amino-, 6-hydroxy-, and 6-Methoxy-5,8-Dimethylisoquinoline," Australian. J. Chem., 1969, vol. 22, pp. 2489-2492.

Sharp, "Split Genes and RNA Splicing," Cell, 1994, vol. 77, pp. 805-815.

Black, "Mechanisms of Alternative Pre-Messenger RNA Splicing," Annu. Rev. Biochem., 2003, vol. 72, pp. 291-336.

Manley et al., "SR Proteins and Splicing Control," Genes & Development,1996, vol. 10, pp. 1569-1579.

Graveley, "Sorting out the Complexity of SR Protein Functions," RNA, 2000, vol. 6, pp. 1197-1211.

Wang et al., "SC35 Plays a Role in T Cell Development and Alternative Splicing of CD45," Molecular Cell, 2001, vol. 7, pp. 331-342.

Ewing et al., "Analysis of Expressed Sequence Tags Indicates 35,000 Human Genes," Nature Genetics, 2000, vol. 25, pp. 232-234.

Johnson et al., "Genome-Wide Survey of Human Alternative Pre-mRNA Splicing with Exon Junction Microarrays," Science, vol. 302, pp. 2141-2144, 2003.

Cartegni et al., "Listening to Silence and Understanding Nonsense: Exonic Mutations that Affect Splicing," Nature Reviews- Genetics, Apr. 2002, vol. 3, pp. 285-298.

Tazi et al., "The Spliceosome: a Novel Multi-faceted Target for Therapy," Trends in Biochemical Sciences, 2005, vol. 30, No. 8, pp. 469-478.

Nissim-Rafinia et al., "Cellular and Viral Splicing Factors Can Modify the Splicing Pattern of CFTR Transcripts Carrying Splicing Mutations," Human Molecular Genetics, 2000, vol. 9, No. 12, pp. 1771-1778.

Hofmann et al., "Htra2-β1 Stimulates an Exonic Splicing Enhancer and can Restore Full-length SMN Expression to Sirvival Motor Neuron 2 (SMN2)," PNAS, 2000, vol. 97, No. 17, pp. 9618-9623.

Sazani et al., "Systemically Delivered Antisense Oligomers Upregulate Gene Expression in Mouse Tissues," Nature Biotechnology, 2002, vol. 20, pp. 1228-1233.

Sazani et al., "Modulation of Alternative Splicing by Antisense Oligonucleotides," Prog. Mol. Subcell. Biol., vol. 31, pp. 217-239, 2003.

Cartegini et al., "Correction of Disease-associated Exon Skipping by Synthetic Exon-specific Activators," Nature Structural Biology, 2003, vol. 10, No. 2, pp. 120-125.

Andreassi et al., "Aclarubicin Treatment Restores SMN Levels to Cells Derived from Type 1 Spinal Muscular Atrophy Patients," Human Molecular Genetics, 2001, vol. 10, No. 24, pp. 2841-2849.

Liu et al., "Partial Correction of Endogenous F508 CFTR in Human Cystic Fibrosis Airway Epithelia by Spliceosome-mediated RNA Trans-splicing," Nature Biotechnology, 2002, vol. 20, pp. 47-52.

Bakkour et al., "Small-Molecule Inhibition of HIV pre-mRNA Splicing as a Novel Antiretroviral Therapy to Overcome Drug Resistance," PLOS Pathogens, 2007, vol. 3, issue 10, pp. 1530-1539.

Connor et al., "VPR is Required for Efficient Replication of Human Immunodeficiency Virus type-1 in Mononuclear Phagocytes," Virology, (1995), vol. 206, pp. 935-944.

Wang et al., "Alternative isoform regulation in human tissue transcriptomes,"Nature, vol. 456, pp. 470-476, Nov. 2008.

Pan et al., "Deep surveying of alternative splicing complexity in the human transcriptome by high-throughput sequencing,"Nature Genetics, vol. 40, No. 12, pp. 1413-1415, Dec. 2008.

F. J. Leinweber, "Possible Physiological Roles of Carboxylic Ester Hydrolases," Drug Metabolism Reviews, vol. 18, No. 4, pp. 379-439, 1987.

Mar. 9, 2012 International Search Report issued in International Patent Application No. PCT/IB32011/055643.

Jun. 18, 2013 International Preliminary Report on Patentability issued in International Patent Application No. PCT/IB2011/055643.

U.S. Appl. No. 13/377,753 in the name of Tazi et al., filed Jun. 4, 2012.

U.S. Appl. No. 13/377,760 in the name of Tazi et al., filed Jul. 2, 2012.

U.S. Appl. No. 13/993,990 in the name of Tazi et al., filed Jul. 13, 2012.

Loriga et al., "Quinoxaline chemistry. Part 8. 2-[Anilinol-3-[carboxyl-6(7)-substituted quinoxalines as non classical antifolate agents. Synthesis and evaluation of in vitro anticancer, anti-HIV and antifungal activity," Farmaco 5:531 -37 (1997).

Loriga et al., "Quinoxaline chemistry. Part 7. 2-[aminobenzoatesl-and 2-[aminobenzoylglutamate]-quinoxalines as classical antifolate agents. Synthesis and evaluation of in vitro anticancer, anti-HIV and antifungal activity," Farmaco 52:157-66 (PubMed Abstract No. 9212450) (1997).

Nov. 21, 2013 Office Action issued in U.S. Appl. No. 13/377,760.
Dec. 23, 2013 Office Action issued in U.S. Appl. No. 13/377,753.
Oct. 27, 2014 Office Action issued in U.S. Appl. No. 13/993,990.
CAS Registry No. 215589-34-7 added on STN on Dec. 15, 1998.
CAS Registry No. 208661-32-9 added on STN on Jul. 19, 1998.
CAS Registry No. 204851-25-2 added on STN on Apr. 30, 1998.
CAS Registry No. 138386-77-3 added on STN on Jan. 17, 1992.
CAS Registry No. 70682-97-2 added on STN on Nov. 16, 1984.
CAS Registry No. 10562-04-6 added on STN on Nov. 16, 1984.
CAS Registry No. 5468-85-9 added on STN on Nov. 16, 1984.
CAS Registry No. 313266-85-2 added on STN on Jan. 9, 2001.
CAS Registry No. 294668-01-2 added on STN on Oct. 11, 2000.
CAS Registry No. 342653-87-6 added on STN on Jun. 20, 2001.
CAS Registry No. 449780-95-4 added on STN on Sep. 12, 2002.
CAS Registry No. 449780-94-3 added on STN on Sep. 12, 2002.
CAS Registry No. 324526-73-0 added on STN on Feb. 27, 2001.
Jan. 13, 2015 Russian Office Action issued in Russian Application No. 2011149572/04(074427).

COMPOUNDS USEFUL FOR TREATING CANCER

This is a continuation of application Ser. No. 13/377,745 filed Jul. 5, 2012, now abandoned, which is a National Stage Application of PCT/IB2010/052560 filed Jun. 14, 2010, and claims the benefit of U.S. Provisional Application Nos. 61/186,552 filed Jun. 12, 2009 and 61/186,544 filed Jun. 12, 2009 and European Application Nos. 09305540.8 filed Jun. 12, 2009 and 09162630.9 filed Jun. 12, 2009. The entire disclosures of the prior applications are hereby incorporated by reference herein in their entirety.

FIELD OF THE INVENTION

The present disclosure is generally directed to the manufacture and use of compounds to treat cancer.

BACKGROUND OF THE INVENTION

In most cancers, mortality is not due to the primary tumor but rather to the derived metastases. This malignant progression is clinically defined by the appearance of metastatic cells. Tumor metastases are typically defined by a primary loss of cell adhesion and an increase of cell motility, which allows for invasive cell to leave the initial tumor site and colonize various target tissues.

Metastases are considered as a recurrent feature of uncontrolled malignant progression of cancer. During this process, tumor cells complete their malignant transformation by increasing their migratory capacity. Cancer cells can then disseminate and establish new tumor foci in far away sites. This event is termed "metastatic cascade," which, as indicated immediately above, is marked by invasion of tissues around the tumor, venous or lymphatic intravasation, migration and establishment of new tumors in distant places of an organism that may escape from all innate defense mechanisms.

Because no efficient therapeutic options presently exist for the treatment or prevention of metastatic tumors, metastatic invasion a major cause of death worldwide. Due to the frequency of cancers diagnosed at the metastatic stage and the lack of viable therapeutic options at this stage of the disease, the development of molecules that specifically target metastatic invasion is crucial for a major breakthrough in cancer treatments.

The compounds and methods of use as described herein are consistent with numerous published reports during the last twenty years that demonstrate a link between changes in RNA alternative splicing and metastatic invasion, which has opened new avenues for therapeutic strategies.

SUMMARY OF THE INVENTION

As discussed in further detail below and as shown in the working examples, formula (I) and derivatives thereof are able to correct defects of alternative splicing, a mechanism closely associated with the invasive progression of metastatic. cancers. Thus, in certain aspects, the compounds described herein may be useful for preventing, inhibiting, or treating cancer.

In certain aspects, the compounds described herein further relate to a method of preventing, inhibiting or treating cancer. For example, the method can include administering an effective amount of a compound having formula (I) or any derivative thereof as described below or one of its pharmaceutically acceptable salts to a patient.

As described in greater detail below, the compounds described herein can be included in pharmaceutical compositions.

DETAILED DESCRIPTION OF THE INVENTION

According to a first aspect, the subject-matter described herein relates to a compound of formula (I)

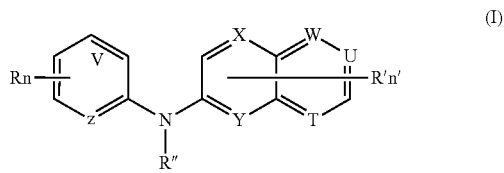

wherein:

means an aromatic ring wherein V is C or N and when V is N, V is in an ortho, meta or para position with respect to Z, i.e. forms respectively a pyridazine, a pyrimidine or a pyrazine group, R independently represents a hydrogen atom, a halogen atom or a group chosen among a —CN group, a hydroxyl group, a —COOR$_1$ group, a (C$_1$-C$_3$)fluoroalkyl group, a (C$_1$-C$_3$)fluoroalkoxy group, a —NO$_2$ group, a —NR$_1$R$_2$ group, a (C$_1$-C$_4$)alkoxy group, a phenoxy group and a (C$_1$-C$_3$)alkyl group, the alkyl being optionally mono-substituted by a hydroxyl group, R$_1$ and R$_2$ are independently a hydrogen atom or a (C$_1$-C$_3$) alkyl group, n is 1, 2 or 3, n' is 1 or 2, R' is a hydrogen atom or a group chosen among a (C$_1$-C$_3$) alkyl group, a halogen atom, a hydroxyl group, a —COOR$_1$ group, a —NO$_2$ group, a —NR$_1$R$_2$ group, a morpholinyl or a morpholino group, a N-methylpiperazinyl group, a (C$_1$-C$_3$)fluoroalkyl group, a (C$_1$-C$_4$) alkoxy group and a —CN group, R" is a hydrogen atom or a (C$_1$-C$_4$)alkyl group, Z is N or C, Y is N or C, X is N or C, W is N or C, T is N or C, U is N or C, and wherein at most four of the groups V, T, U, Z, Y, X and W are N, and at least one of the groups T, U, Y, X and W is N, or anyone of its pharmaceutically acceptable salt, for use as an agent for preventing, inhibiting or treating cancer.

According to one aspect, formula (I) as defined above includes a compound wherein Z is N, V is C, Y is N, X is C, T is C, U is C and W is C, which can be used as an agent for preventing, inhibiting or treating cancer.

According to another aspect, formula (I) as defined above includes a compound wherein Z is C, V is C, Y is N, X is C, T is C, U is C and W is C, which can be used as an agent for preventing, inhibiting or treating cancer.

According to another aspect, formula (I) as defined above includes a compound wherein Z is N, V is C, Y is C, X is N, T is C, U is C and W is C, which can be used as an agent for preventing, inhibiting or treating cancer.

According to another aspect, formula (I) as defined above includes a compound wherein Z is N, V is C, Y is C, X is C, T is C, U is C and W is N, which can be used as an agent for preventing, inhibiting or treating cancer.

According to another aspect, formula (I) as defined above includes a compound, wherein Z is N, V is N and is in the para position with respect to Z, Y is N, X is C, T is C, U is C and W is C, which can be used as an agent for preventing, inhibiting or treating cancer.

According to another aspect, formula (I) as defined above includes a compound, wherein Z is C, V is N and is in the para position with respect to Z, Y is C, X is N, T is C, U is C and W is C, which can be used as an agent for preventing, inhibiting or treating cancer.

According to another aspect, formula (I) as defined above includes a compound, wherein Z is C, V is N and is in the meta position with respect to Z and is in the para position with respect to the bond linked to NR'', Y is N, X is C, T is C, U is C and W is C, for use as an agent for preventing, inhibiting or treating cancer.

According to another aspect, formula (I) as defined above includes a compound, wherein Z is C, V is N and is in the meta position with respect to Z and is in the para position with respect to the bond linked to NR'', Y is C, X is N, T is C, U is C and W is C, for use as an agent for preventing, inhibiting or treating cancer.

According to another aspect, formula (I) as defined above includes a compound, wherein Z is C, V is C, Y is C, X is N, T is C, U is C and W is C, for use as an agent for preventing, inhibiting or treating cancer.

According to another aspect, formula (I) as defined above includes a compound, wherein Z is C, V is C, Y is N, X is N, T is C, U is C and W is C, for use as an agent for preventing, inhibiting or treating cancer.

According to another aspect, formula (I) as defined above includes a compound, wherein Z is N, V is N and is in the meta position with respect to Z and in the ortho position with respect to the bond linked to NR'', Y is N, X is C, T is C, U is C and W is C, for use as an agent for preventing, inhibiting or treating cancer.

According to another aspect, formula (I) as defined above includes a compound, wherein Z is N, V is N and is in the para position with respect to Z, Y is C, X is C, T is C, U is C and W is N, for use as an agent for preventing, inhibiting or treating cancer.

According to another aspect, formula (I) as defined above includes a compound, wherein Z is N, V is N and is in the para position with respect to Z, Y is C, X is N, T is C, U is C and W is C, for use as an agent for preventing, inhibiting or treating cancer.

According to another aspect, formula (I) as defined above includes a compound, wherein Z is N, V is C, Y is N, X is N, T is C, U is C and W is C, for use as an agent for preventing, inhibiting or treating cancer.

According to another aspect, formula (I) as defined above includes a compound, wherein Z is N, V is N and is in the meta position with respect to Z and is in the ortho position with respect to the bond linked to NR'', Y is N, X is N, T is C, U is C and W is C, for use as an agent for preventing, inhibiting or treating cancer.

According to another aspect, formula (I) as defined above includes a compound, wherein Z is C, V is C, Y is C, X is C, T is N, U is C and W is C, for use as an agent for preventing, inhibiting or treating cancer.

According to another aspect, formula (I) as defined above includes a compound, wherein Z is N, V is C, Y is C, X is C, T is N, U is C and W is C, for use as an agent for preventing, inhibiting or treating cancer.

According to another aspect, formula (I) as defined above includes a compound, wherein Z is N, V is C, Y is C, X is C, T is C, U is N and W is C, for use as an agent for preventing, inhibiting or treating cancer.

According to one preferred aspect, formula (I) as defined above, wherein Z is N, V is C, Y is N, X is C, T is C, U is C and W is C, for use as an agent for preventing, inhibiting or treating cancer.

According to another preferred aspect, formula (I) as defined above includes a compound, wherein Z is N, V is N and is in the para position with respect to Z, Y is N, X is C, T is C, U is C and W is C, for use as an agent for preventing, inhibiting or treating cancer.

According to another preferred aspect, formula (I) as defined above includes a compound, wherein Z is C, V is C, Y is C, X is C, T is N, U is C and W is C, for use as an agent for preventing, inhibiting or treating cancer.

According to another preferred aspect, formula (I) as defined above includes a compound, wherein Z is N, V is C, Y is C, X is C, T is C, U is N and W is C, for use as an agent for preventing, inhibiting or treating cancer.

The compounds described herein may exist in the form of free bases or of addition salts with pharmaceutically acceptable acids.

The compounds of formula (I) can include physiologically acceptable acid addition salts such as hydrobromide, tartrate, citrate, trifluoroacetate, ascorbate, hydrochloride, tartrate, triflate, maleate, mesylate, formate, acetate and fumarate.

The compounds of formula (I) and or salts thereof may form solvates (e.g. hydrates) and the compounds describe herein can include all such solvates.

In the context of the present disclosure, the term:
"halogen" is understood to mean chlorine, fluorine, bromine, or iodine, and in particular denotes chlorine, fluorine or bromine,
"$(C_1-C_3)$alkyl" as used herein respectively refers to $C_1-C_3$ normal, secondary or tertiary saturated hydrocarbon. Examples are, but are not limited to, methyl, ethyl, 1-propyl, 2-propyl,
"$(C_1-C_3)$alkoxy" as used herein respectively refers to O—$(C_1-C_3)$alkyl moiety, wherein alkyl is as defined above. Examples include, but are not limited to, methoxy, ethoxy, 1-propoxy, 2-propoxy,
"fluoroalkyl group" and "fluoroalkoxy group" refers respectively to alkyl group and alkoxy group as above-defined, the groups being substituted by at least one fluorine atom. Examples of perfluoroalkyl groups include, but are not limited to, trifluoromethyl or perfluoropropyl.
"patient" may extend to humans or mammals. For example, the term "patient" can include cats or dogs.

In one aspect, the compounds described herein include a compound of formula (Ia)

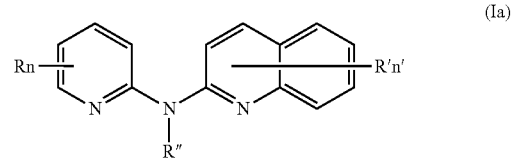

wherein:
R independently represent a hydrogen atom, a halogen atom or a group chosen among a $(C_1-C_3)$alkyl group, a —CN group, a hydroxyl group, a —COOR$_1$ group, a (C$_1$-C$_3$)fluoroalkyl group, a —NO$_2$ group, a —NR$_1$R$_2$ group and a (C$_1$-C$_3$)alkoxy group, R" is as defined above and is advantageously a hydrogen atom, n is as defined above and is advantageously 1, n' is as defined above and is advantageously 1, R' is a hydrogen atom, a halogen atom or a group chosen among a (C$_1$-C$_3$)alkyl group, a —NO$_2$ group, a (C$_1$-C$_3$) alkoxy group and a —NR$_1$R$_2$ group, R$_1$ and R$_2$ are a hydrogen atom or a (C$_1$-C$_3$)alkyl group, or one of its pharmaceutically acceptable salt, for use as an agent for preventing, inhibiting or treating cancer.

In one aspect, the compounds described herein include a compound of formula (Ib)

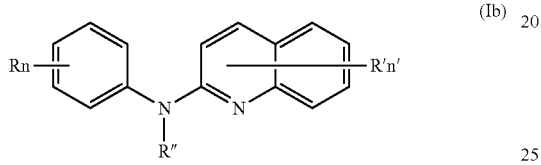

wherein:

R independently represent a hydrogen atom, a halogen atom or a group chosen among a (C$_1$-C$_3$)alkyl group, a —NR$_1$R$_2$ group, a (C$_1$-C$_3$)fluoroalkoxy group, a —NO$_2$ group, a phenoxy group and a (C$_1$-C$_4$)alkoxy group, R$_1$ and R$_2$ are independently a hydrogen atom or a (C$_1$-C$_3$) alkyl group, R" is as defined above and is advantageously a hydrogen atom, n is as defined above and is preferably 1 or 2, n' is as defined above and is preferably 1, R' is a hydrogen atom, a halogen atom or a group chosen among a (C$_1$-C$_3$)alkyl group and a (C$_1$-C$_4$)alkoxy group, or one of its pharmaceutically acceptable salt, for use as an agent for preventing, inhibiting or treating cancer.

In one aspect, the compounds described herein include a compound of formula (Ic)

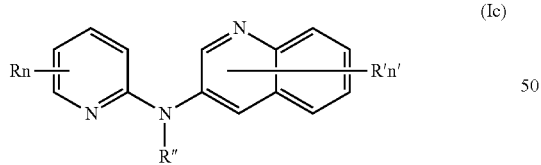

wherein:

R independently represent a hydrogen atom or a group chosen among a (C$_1$-C$_3$)alkyl group, a (C$_1$-C$_3$)fluoroalkyl group, a —NR$_1$R$_2$ group, a —COOR$_1$ group, a —NO$_2$ group and a (C$_1$-C$_3$)alkoxy group, R" is as defined above and is advantageously a hydrogen atom, n is as defined above and is advantageously 1, n' is as defined above and is advantageously 1, R' is a hydrogen atom, R$_1$ and R$_2$ are independently a hydrogen atom or a (C$_1$-C$_3$) alkyl group, or one of its pharmaceutically acceptable salt, for use as an agent for preventing, inhibiting or treating cancer.

In one aspect, the compounds described herein include a compound of formula (Id)

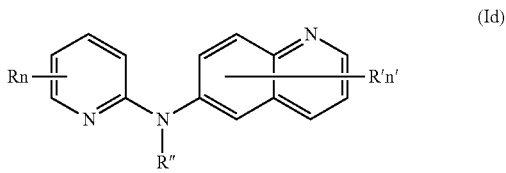

wherein:

R independently represents a hydrogen atom or a group chosen among a (C$_1$-C$_3$)alkyl group, a (C$_1$-C$_3$)fluoroalkyl group and a (C$_1$-C$_3$)alkoxy group, R" is as defined above and is advantageously a hydrogen atom, n is as defined above and is advantageously 1, n' is as defined above and is advantageously 1, R' is a hydrogen atom, or one of its pharmaceutically acceptable salt, for use as an agent for preventing, inhibiting or treating cancer.

In certain aspects, the compounds described herein include a compound of formula (Ie)

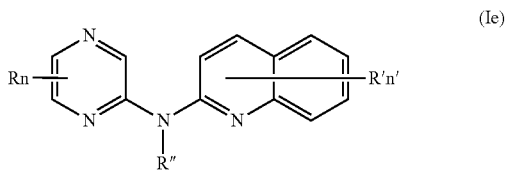

wherein:

R represents a hydrogen atom,

R" is as defined above and is advantageously a hydrogen atom, n is as defined above and is advantageously 1, n' is as defined above and is advantageously 1, R' is a hydrogen atom, a halogen atom or a group chosen among a (C$_1$-C$_3$)alkyl group and a (C$_1$-C$_3$)alkoxy group, or one of its pharmaceutically acceptable salt, for use as an agent for preventing, inhibiting or treating cancer.

In another aspect, the compounds described herein include a compound of formula (If)

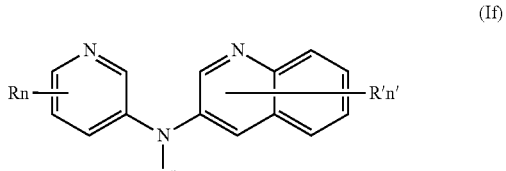

wherein:

R represents a hydrogen atom,

R" is as defined above and is advantageously a hydrogen atom, n is as defined above and is advantageously 1, n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Ig)

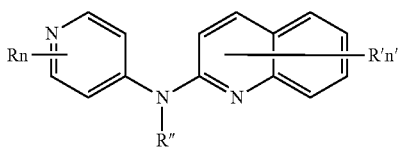

wherein:
R represents a hydrogen atom,
R" is as defined above and is advantageously a hydrogen atom,
n is as defined above and is advantageously 1,
n' is as defined above and is advantageously 1,
R' is a hydrogen atom or a halogen atom,
or one of its pharmaceutically acceptable salt,
for use as an agent for preventing, inhibiting or treating cancer.

In one aspect, the compounds described herein include a compound of formula (Ih)

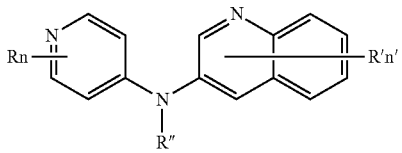

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Ii)

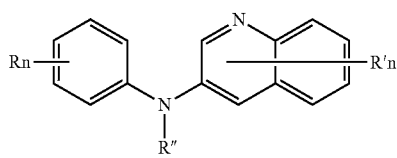

wherein:
R independently represents a hydrogen atom or a group chosen among a $(C_1\text{-}C_3)$fluoroalkoxy group and a $(C_1\text{-}C_3)$alkoxy group,
R" is as defined above and is advantageously a hydrogen atom,
n is as defined above and is advantageously 1,
n' is as defined above and is advantageously 1, R' is a hydrogen atom,
or one of its pharmaceutically acceptable salt,
for use as an agent for preventing, inhibiting or treating cancer.

In one aspect, the compounds described herein include a compound of formula (Ij)

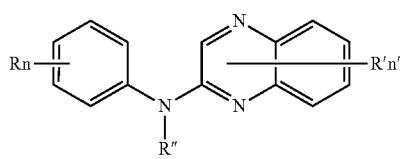

wherein:
R independently represents a hydrogen atom or a group chosen among a $(C_1\text{-}C_3)$fluoroalkoxy group and a $(C_1\text{-}C_3)$alkyl group,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Ik)

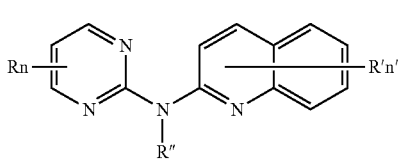

wherein:
R represents a hydrogen atom,
R" is as defined above and is advantageously a hydrogen atom,
n is as defined above and is advantageously 1,
n' is as defined above and is advantageously 1,
R' is a hydrogen atom, a halogen atom or a $(C_1\text{-}C_3)$alkyl group,
or one of its pharmaceutically acceptable salt,
for use as an agent for preventing, inhibiting or treating cancer.

In one aspect, the compounds described herein include a compound of formula (Il)

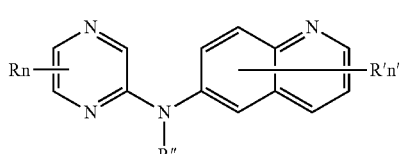

wherein:
R represents a hydrogen atom,
R" is as defined above and is advantageously a hydrogen atom,
n is as defined above and is advantageously 1,
n' is as defined above and is advantageously 1, R' is a hydrogen atom,
or one of its pharmaceutically acceptable salt,
for use as an agent for preventing, inhibiting or treating cancer.

In one aspect, the compounds described herein include a compound of formula (Im)

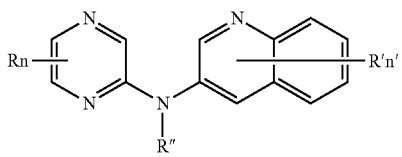

(Im)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Io)

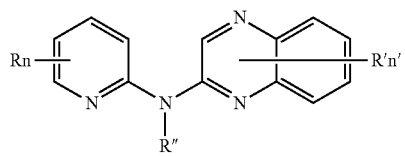

(Io)

wherein:
R independently represent a hydrogen atom or a halogen atom or a group chosen among, a —NO$_2$ group, a —CN group and a (C$_1$-C$_3$)alkyl group, said alkyl being optionally mono-substituted by a hydroxyl group,
R" is as defined above and is advantageously a hydrogen atom,
n is as defined above and is advantageously 1,
n' is as defined above and is advantageously 1,
R' is a hydrogen atom, a halogen atom or a (C$_1$-C$_3$)fluoroalkyl group,
or one of its pharmaceutically acceptable salt,
for use as an agent for preventing, inhibiting or treating cancer.

In one aspect, the compounds described herein include a compound of formula (Ip)

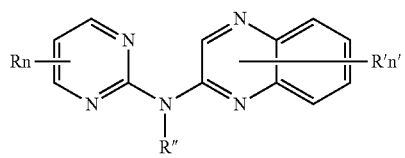

(Ip)

wherein:
R represents a hydrogen atom,
R" is as defined above and is advantageously a hydrogen atom,
n is as defined above and is advantageously 1,
n' is as defined above and is advantageously 1,
R' is a hydrogen atom,
or one of its pharmaceutically acceptable salt,
for use as an agent for preventing, inhibiting or treating cancer.

In one aspect, the compounds described herein include a compound of formula (Iq)

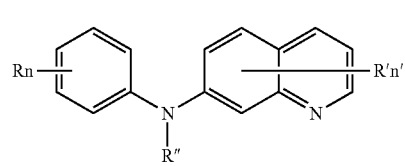

(Iq)

wherein:
R independently represents a hydrogen atom, a (C$_1$-C$_3$) alkoxy group or a (C$_1$-C$_3$)fluoroalkoxy group,
R" is as defined above and is advantageously a hydrogen atom,
n is as defined above and is advantageously 1,
n' is as defined above and is advantageously 1,
R' is a hydrogen atom or a group chosen among a —NR$_1$R$_2$ group, a N-methylpiperazinyl group, a (C$_1$-C$_3$)alkoxy group and a morpholino group,
R$_1$ and R$_2$ are independently a hydrogen atom or a (C$_1$-C$_3$) alkyl group,
or one of its pharmaceutically acceptable salt,
for use as an agent for preventing, inhibiting or treating cancer.

In one aspect, the compounds described herein include a compound of formula (Ir)

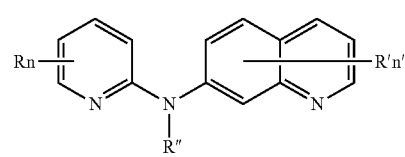

(Ir)

wherein:
R independently represents a hydrogen atom or a (C$_1$-C$_3$) alkyl group,
R" is as defined above and is advantageously a hydrogen atom,
n is as defined above and is advantageously 1,
n' is as defined above and is advantageously 1,
R' is a hydrogen atom or a group chosen among a —NR$_1$R$_2$ group, a morpholino group and a (C$_1$-C$_3$)alkoxy group,
R$_1$ and R$_2$ are independently a hydrogen atom or a (C$_1$-C$_3$) alkyl group,
or one of its pharmaceutically acceptable salt,
for use as an agent for preventing, inhibiting or treating cancer.

In one aspect, the compounds described herein include a compound of formula (Iee)

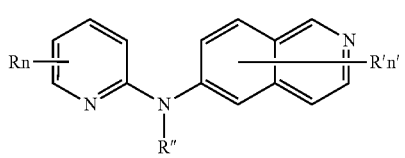

(Iee)

wherein:
R independently represents a hydrogen atom, a (C$_1$-C$_3$) alkyl group or a (C$_1$-C$_3$)fluoroalkyl group, R" is as defined above and is advantageously a hydrogen atom, n is as defined above and is advantageously 1, n' is as defined above and is advantageously 2, R' is a hydrogen atom or a $(C_1-C_3)$alkyl group, or one of its pharmaceutically acceptable salt, for use as an agent for preventing, inhibiting or treating cancer.

Among the previous defined families of compounds of formulae (Ia) to (Iee), some are more particularly preferred for their use as an agent for preventing, inhibiting or treating cancer. These preferred compounds particularly belong to formulae (Ia), (Ie), (Iq) and (Iee), as defined above or one of its pharmaceutically acceptable salts.

Accordingly, the portions below further relate to a compound chosen among compounds of formulae (Ia), (Ie), (Iq) and (Iee), and their pharmaceutically acceptable salts for use as an agent for preventing, inhibiting or treating cancer.

In certain aspects, the compounds described herein include a compound of formula (Ia)

wherein:

R independently represents a hydrogen atom, a halogen atom or a group chosen among a $(C_1-C_3)$alkyl group, a —CN group, a —COOR$_1$ group and a $(C_1-C_3)$fluoroalkyl group, R" is as defined above and more preferably is a hydrogen atom, R$_1$ is as defined above, n is as defined above, n' is as defined above, R' is a halogen atom, a $(C_1-C_4)$alkyl group, a $(C_1-C_4)$ alkoxy group or a —NO$_2$ group, or one of its pharmaceutically acceptable salt, for use as an agent for preventing, inhibiting or treating cancer.

In certain aspects, the compounds described herein include a compound of formula (Ie)

wherein:

R represents a hydrogen atom or a $(C_1-C_4)$alkyl group,

R" is as defined above and more preferably is a hydrogen atom, n is as defined above, n' is as defined above, R' is a halogen atom, or one of its pharmaceutically acceptable salt, for use as an agent for preventing, inhibiting or treating cancer.

In certain aspects, the compounds described herein include a compound of formula (Iq)

wherein:

R', R", n and n' are as defined in formula (I), and

R is a $(C_1-C_3)$fluoroalkoxy group, or one of its pharmaceutically acceptable salt, for use as an agent for preventing, inhibiting or treating cancer.

In certain aspects, the compounds described herein include a compound of formula (Iee)

wherein:

R is independently a hydrogen atom or a $(C_1-C_4)$alkyl group,

R, R", n and n' are as defined in formula (I), or one of its pharmaceutically acceptable salt, for use as an agent for preventing, inhibiting or treating cancer.

In certain aspects, the compounds described herein include a compound of formula (Ia) or (Ie) as defined above or one of its pharmaceutically acceptable salts, for use as an agent for preventing, inhibiting or treating cancer.

According to a preferred embodiment, the compounds described herein for use as an agent for preventing, inhibiting or treating cancer, is chosen from:

(1) (8-Chloro-quinolin-2-yl)-pyridin-2-yl-amine
(2) 2-(Quinolin-2-ylamino)-isonicotinic acid
(3) (4-Methyl-pyridin-2-yl)-quinolin-2-yl-amine
(4) Pyridin-2-yl-quinolin-2-yl-amine
(5) 2-(8-Chloro-quinolin-2-ylamino)-isonicotinic acid
(6) (8-Chloro-quinolin-2-yl)-(4-methyl-pyridin-2-yl)-amine
(7) 6-(Quinolin-2-ylamino)-nicotinonitrile
(8) Quinolin-2-yl-(4-trifluoromethoxy-phenyl)-amine
(9) Pyridin-2-yl-quinolin-3-yl-amine
(10) (3-Methoxy-pyridin-2-yl)-quinolin-3-yl-amine
(11) Quinolin-3-yl-(5-trifluoromethyl-pyridin-2-yl)-amine
(12) (5-Nitro-pyridin-2-yl)-quinolin-3-yl-amine
(13) (5-Methyl-pyridin-2-yl)-quinolin-3-yl-amine
(14) 2-(Quinolin-3-ylamino)-isonicotinic acid
(15) Quinolin-6-yl-(5-trifluoromethyl-pyridin-2-yl)-amine
(16) (6-Methyl-pyridin-2-yl)-quinolin-6-yl-amine
(17) N-(6-methylpyridin-2-yl)quinolin-2-amine
(18) 8-chloro-N-(6-methylpyridin-2-yl)quinolin-2-amine
(19) 4-methyl-N-(pyridin-2-yl)quinolin-2-amine
(20) 4-methyl-N-(4-methylpyridin-2-yl)quinolin-2-amine
(21) 3-methyl-N-(4-methylpyridin-2-yl)quinolin-2-amine
(22) 3-methyl-N-(pyridin-2-yl)quinolin-2-amine
(23) 6-((4-methylquinolin-2-yl)amino)nicotinonitrile
(24) 6-((3-methylquinolin-2-yl)amino)nicotinonitrile
(25) 6-chloro-N-(4-methylpyridin-2-yl)quinolin-2-amine
(26) 6-chloro-N-(6-methylpyridin-2-yl)quinolin-2-amine
(27) 4-methyl-N-(5-nitropyridin-2-yl)quinolin-2-amine
(28) N-(3-nitropyridin-2-yl)quinolin-2-amine
(29) 8-chloro-N-(3-nitropyridin-2-yl)quinolin-2-amine
(30) 2-((4-methylquinolin-2-yl)amino)nicotinonitrile
(31) N-(3-methylpyridin-2-yl)quinolin-2-amine
(32) N-(5-methylpyridin-2-yl)quinolin-2-amine
(33) 2-(quinolin-2-ylamino)isonicotinonitrile
(34) N-(5-(trifluoromethyl)pyridin-2-yl)quinolin-2-amine
(35) 8-chloro-N-(3-methylpyridin-2-yl)quinolin-2-amine
(36) 8-chloro-N-(5-methylpyridin-2-yl)quinolin-2-amine
(37) 8-chloro-N-(5-(trifluoromethyl)pyridin-2-yl)quinolin-2-amine
(38) N-(3-methoxypyridin-2-yl)quinolin-2-amine
(39) N-(5-nitropyridin-2-yl)quinolin-2-amine
(40) 6-((8-chloroquinolin-2-yl)amino)nicotinonitrile
(41) N-(5-fluoropyridin-2-yl)quinolin-2-amine
(42) N-(6-(trifluoromethyl)pyridin-2-yl)quinolin-2-amine
(43) 8-chloro-N-(5-fluoropyridin-2-yl)quinolin-2-amine
(44) 2-((8-chloroquinolin-2-yl)amino)nicotinic acid
(45) 4-methyl-N-(6-methylpyridin-2-yl)quinolin-2-amine
(46) 3-methyl-N-(6-methylpyridin-2-yl)quinolin-2-amine
(47) 5-cyano-2-(quinolin-2-ylamino)pyridin-1-ium chloride
(48) 2-((8-chloroquinolin-2-yl)amino)-4-methylpyridin-1-ium chloride
(49) 8-chloro-N-(4-ethylpyridin-2-yl)quinolin-2-amine
(50) 8-chloro-N-(6-ethylpyridin-2-yl)quinolin-2-amine
(51) 8-chloro-N-(4,6-dimethylpyridin-2-yl)quinolin-2-amine
(52) 6-((8-chloroquinolin-2-yl)amino)-2-methylnicotinonitrile
(53) 8-chloro-N-(4-chloropyridin-2-yl)quinolin-2-amine
(54) 8-methyl-N-(4-methylpyridin-2-yl)quinolin-2-amine
(55) N-(5-bromo-4-methylpyridin-2-yl)-8-chloroquinolin-2-amine
(56) 8-chloro-N-(3-ethyl-6-methylpyridin-2-yl)quinolin-2-amine

(57) 8-fluoro-N-(4-methylpyridin-2-yl)quinolin-2-amine
(58) 8-bromo-N-(4-methylpyridin-2-yl)quinolin-2-amine
(59) methyl 6-(quinolin-2-ylamino)nicotinate
(60) methyl 6-[(8-chloroquinolin-2-yl)amino]pyridine-3-carboxylate
(61) methyl 6-[(3-methylquinolin-2-yl)amino]pyridine-3-carboxylate
(62) methyl 2-[(8-chloroquinolin-2-yl)amino]pyridine-3-carboxylate
(63) 8-methoxy-N-(4-methylpyridin-2-yl)quinolin-2-amine
(64) N-(4-methylpyridin-2-yl)-5-nitroquinolin-2-amine
(65) 2-N-(4-methylpyridin-2-yl)quinoline-2,8-diamine
(66) N-(4-methylpyridin-2-yl)-5-aminoquinolin-2-amine
(67) methyl 6-[(4-methylquinolin-2-yl)amino]pyridine-3-carboxylate
(68) 8-chloro-N-[4-(trifluoromethyl)pyridin-2-yl]quinolin-2-amine
(69) 2-[(8-chloroquinolin-2-yl)amino]pyridin-3-ol
(70) 8-chloro-N-[6-(trifluoromethyl)pyridin-2-yl]quinolin-2-amine
(71) 6-chloro-N-(5-fluoropyridin-2-yl)quinolin-2-amine
(72) N-(6-ethylpyridin-2-yl)-3-methylquinolin-2-amine
(73) N-(5-fluoropyridin-2-yl)-3-methylquinolin-2-amine
(74) 3-methyl-N-[5-(trifluoromethyl)pyridin-2-yl]quinolin-2-amine
(75) 4-N-(8-chloroquinolin-2-yl)-1-N,1-N-dimethylbenzene-1,4-diamine
(76) N-(4-methoxyphenyl)quinolin-2-amine
(77) 8-chloro-N-(4-methoxyphenyl)quinolin-2-amine
(78) 4-methyl-N-[4-(trifluoromethoxy)phenyl]quinolin-2-amine
(79) N-(4-methoxyphenyl)-3-methylquinolin-2-amine
(80) 3-methyl-N-[4-(trifluoromethoxy)phenyl]quinolin-2-amine
(81) 1-N,1-N-dimethyl-4-N-(3-methylquinolin-2-yl)benzene-1,4-diamine
(82) N-[2-methyl-4-(trifluoromethoxy)phenyl]quinolin-2-amine
(83) N-[3-(trifluoromethoxy)phenyl]quinolin-2-amine
(84) N-[2-(trifluoromethoxy)phenyl]quinolin-2-amine
(85) N-(4-nitrophenyl)quinolin-2-amine
(86) N-(3-fluorophenyl)quinolin-2-amine
(87) 8-chloro-N-[3-(trifluoromethoxy)phenyl]quinolin-2-amine
(88) 8-chloro-N-(3-fluorophenyl)quinolin-2-amine
(89) 2-{[4-(trifluoromethoxy)phenyl]amino}quinolin-1-ium chloride
(90) 8-chloro-N-[4-(trifluoromethoxy)phenyl]quinolin-2-amine
(91) 3-methyl-N-[2-methyl-4-(trifluoromethoxy)phenyl]quinolin-2-amine
(92) 3-methyl-N-[3-(trifluoromethoxy)phenyl]quinolin-2-amine
(93) 3-methyl-N-[2-(trifluoromethoxy)phenyl]quinolin-2-amine
(94) 8-chloro-N-[2-methyl-4-(trifluoromethoxy)phenyl]quinolin-2-amine
(95) 3-methyl-2-{[4-(trifluoromethoxy)phenyl]amino}quinolin-1-ium chloride
(96) 6-chloro-N-(4-(trifluoromethoxy)phenyl)quinolin-2-amine
(97) 4-methyl-2-{[4-(trifluoromethoxy)phenyl]amino}quinolin-1-ium chloride
(98) 8-bromo-N-[4-(trifluoromethoxy)phenyl]quinolin-2-amine
(99) 8-fluoro-N-[4-(trifluoromethoxy)phenyl]quinolin-2-amine
(100) 8-methyl-N-[4-(trifluoromethoxy)phenyl]quinolin-2-amine
(101) N-(4-butoxyphenyl)-8-chloroquinolin-2-amine
(102) N-(4-phenoxyphenyl)quinolin-2-amine
(103) 8-methoxy-N-[4-(trifluoromethoxy)phenyl]quinolin-2-amine
(104) 8-chloro-N-[3-chloro-4-(trifluoromethoxy)phenyl]quinolin-2-amine
(105) N-(6-methylpyridin-2-yl)quinolin-3-amine
(106) N-(3-nitropyridin-2-yl)quinolin-3-amine
(107) N-(5-methylpyridin-2-yl)quinolin-6-amine
(108) N-(3-methoxypyridin-2-yl)quinolin-6-amine
(109) 6-chloro-N-(pyrazin-2-yl)quinolin-2-amine
(110) 8-bromo-N-(pyrazin-2-yl)quinolin-2-amine
(111) 8-methyl-N-(pyrazin-2-yl)quinolin-2-amine
(112) 8-chloro-N-(pyrazin-2-yl)quinolin-2-amine
(113) N-(pyrazin-2-yl)quinolin-2-amine
(114) 4-methyl-N-(pyrazin-2-yl)quinolin-2-amine
(115) 3-methyl-N-(pyrazin-2-yl)quinolin-2-amine
(116) 8-fluoro-N-(pyrazin-2-yl)quinolin-2-amine
(117) 8-methoxy-N-(pyrazin-2-yl)quinolin-2-amine
(118) N-(pyridin-3-yl)quinolin-3-amine
(119) 8-chloro-N-(pyridin-4-yl)quinolin-2-amine
(120) N-(pyridin-4-yl)quinolin-2-amine
(121) N-(pyridin-4-yl)quinolin-3-amine
(122) N-[4-(trifluoromethoxy)phenyl]quinolin-3-amine
(123) N-(4-methoxyphenyl)quinolin-3-amine
(124) N-[4-(trifluoromethoxy)phenyl]quinoxalin-2-amine
(125) N-[2-methyl-4-(trifluoromethoxy)phenyl]quinoxalin-2-amine
(126) N-[3-(trifluoromethoxy)phenyl]quinoxalin-2-amine
(127) N-[2-(trifluoromethoxy)phenyl]quinoxalin-2-amine
(128) N-(pyrimidin-2-yl)quinolin-2-amine
(129) 8-chloro-N-(pyrimidin-2-yl)quinolin-2-amine
(130) 4-methyl-N-(pyrimidin-2-yl)quinolin-2-amine
(131) N-(pyrazin-2-yl)quinolin-6-amine
(132) N-(pyrazin-2-yl)quinolin-3-amine
(133) 6-methyl-N-(naphthalen-2-yl)pyridin-2-amine
(134) N-(naphthalen-2-yl)pyridin-2-amine
(135) N-(pyridin-2-yl)quinoxalin-2-amine
(136) N-(4-methylpyridin-2-yl)quinoxalin-2-amine
(137) 6-(quinoxalin-2-ylamino)pyridine-3-carbonitrile
(138) N-(6-methylpyridin-2-yl)quinoxalin-2-amine
(139) N-(4-methylpyridin-2-yl)-3-(trifluoromethyl)quinoxalin-2-amine
(140) N-(3,5-dichloro-4-methylpyridin-2-yl)quinoxalin-2-amine
(141) N-(4-methyl-3-nitropyridin-2-yl)quinoxalin-2-amine
(142) N-(pyrimidin-2-yl)quinoxalin-2-amine
(143) 4-N,4-N-dimethyl-7-N-[4-(trifluoromethoxy)phenyl]quinoline-4,7-diamine
(144) 4-(morpholin-4-yl)-N-[4-(trifluoromethoxy)phenyl]quinolin-7-amine
(145) 4-methoxy-N-(pyridin-2-yl)quinolin-7-amine
(146) 4-methoxy-N-(4-methylpyridin-2-yl)quinolin-7-amine
(147) 4-N,4-N-dimethyl-7-N-(4-methylpyridin-2-yl)quinoline-4,7-diamine
(148) 5,8-dimethyl-N-(5-methylpyridin-2-yl)isoquinolin-6-amine
(149) 5,8-dimethyl-N-(5-trifluoromethylpyridin-2-yl)isoquinolin-6-amine
(150) N-(4-methylpyridin-2-yl)-8-nitroquinolin-2-amine
(151) 6-chloro-N-(6-ethylpyridin-2-yl)quinolin-2-amine
(152) 6-chloro-N-(5-methylpyridin-2-yl)quinolin-2-amine
(153) 6-chloro-N-[5-(trifluoromethyl)pyridin-2-yl]quinolin-2-amine (154) N2-(8-chloroquinolin-2-yl)-4-methylpyridine-2,3-diamine
(155) N-(4-butoxyphenyl)-3-methylquinolin-2-amine
(156) 4-N-(6-chloroquinolin-2-yl)-1-N,1-N-dimethylbenzene-1,4-diamine
(157) 8-chloro-N-(3-chloro-4-methoxyphenyl)quinolin-2-amine
(158) N1-(8-chloroquinolin-2-yl)-4-(trifluoromethoxy)benzene-1,2-diamine
(159) N-(3-aminopyridin-2-yl)quinolin-3-amine
(160) 6-chloro-N-(4-methylpyridin-2-yl)quinoxalin-2-amine
(161) N-(4-ethylpyridin-2-yl)quinoxalin-2-amine
(162) N-(5-bromo-4-methylpyridin-2-yl)quinoxalin-2-amine
(163) N-(4,6-dimethylpyridin-2-yl)quinoxalin-2-amine
(164) [2-(quinoxalin-2-ylamino)pyridin-4-yl]methanol
(165) N-(4-methyl-5-nitropyridin-2-yl)quinoxalin-2-amine
(166) N-(4-methoxyphenyl)-4-(4-methylpiperazin-1-yl)quinolin-7-amine
(167) 4-methoxy-N-[4-(trifluoromethoxy)phenyl]quinolin-7-amine
(168) N-(4-methylpyridin-2-yl)-4-(morpholin-4-yl)quinolin-7-amine
and their pharmaceutically acceptable salts.

Among the compounds described above, compounds (6), (18), (30), (35), (36), (37), (45), (48), (51), (52), (53), (55), (56), (58), (61), (63), (64), (109), (110), (112), (143), (144) and (148) are of particular interest.

As discussed above, the compounds described herein include compound (6), (18), (30), (35), (36), (37), (45), (48), (51), (52), (53), (55), (56), (58), (61), (63), (64), (109), (110), (112), (143), (144) and (148) or one of its pharmaceutically acceptable salts for use as an agent for preventing, inhibiting or treating cancer.

The compounds of formulae (I), (Ia), (Ib), (Ic), (Id), (Ie), (If), (Ig), (Ih), (Ii), (Ij), (Ik), (Il), (Im), (Io), (Ip), (Iq), (Ir) and (Iee) can comprise one or more asymmetric carbon atoms. They can thus exist in the form of enantiomers or of diastereoisomers. These enantiomers, diastereoisomers and their mixtures, including the racemic mixtures, are encompassed within the scope of the present invention.

The compound of formula (I) and the derivatives thereof can include their pharmaceutically acceptable salts, which include hydrobromide, tartrate, citrate, trifluoroacetate, ascorbate, hydrochloride, tartrate, triflate, maleate, mesylate, formate, acetate and fumarate.

In certain aspects, the compounds described herein includes compounds of formula (Ig)
wherein:
R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, and a ($C_1$-$C_3$)alkoxy group,
n is 1 or 2,
n' is 1 or 2,
R' is a hydrogen atom or a group chosen among a ($C_1$-$C_3$) alkyl group, a halogen atom, a hydroxyl group, a —COOR$_1$ group, a —NO$_2$ group, a —NR$_1$R$_2$ group, a ($C_1$-$C_3$)alkoxy group and a —CN group,
R" is a hydrogen atom or a ($C_1$-$C_4$)alkyl group,
R$_1$ and R$_2$ are independently a hydrogen atom or a ($C_1$-$C_3$) alkyl group,
with the proviso that R and R' are not simultaneously a hydrogen atom,
and when n and n' are 1 and R is a hydrogen atom then R' is not a —COOH group,
or anyone of its pharmaceutically acceptable salts.

In certain aspects, the compounds described herein includes compounds of formula (If)
wherein:
R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, and a ($C_1$-$C_3$)alkoxy group,
n is 1 or 2,
n' is 1 or 2,
R' is a hydrogen atom or a group chosen among a ($C_1$-$C_3$) alkyl group, a halogen atom, a hydroxyl group, a —COOR$_1$ group, a —NO$_2$ group, a —NR$_1$R$_2$ group, a ($C_1$-$C_3$)alkoxy group and a —CN group,
R" is a hydrogen atom or a ($C_1$-$C_4$)alkyl group,
R$_1$ and R$_2$ are independently a hydrogen atom or a ($C_1$-$C_3$) alkyl group,
or anyone of its pharmaceutically acceptable salt.

In certain aspects, the compounds described herein includes compounds of formula (Ih)
wherein:
R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, and a ($C_1$-$C_3$)alkoxy group,
n is 1 or 2,
n' is 1 or 2,
R' is a hydrogen atom or a group chosen among a ($C_1$-$C_3$) alkyl group, a halogen atom, a hydroxyl group, a —COOR$_1$ group, a —NO$_2$ group, a —NR$_1$R$_2$ group, a ($C_1$-$C_3$)alkoxy group and a —CN group,
R" is a hydrogen atom or a ($C_1$-$C_4$)alkyl group,
R$_1$ and R$_2$ are independently a hydrogen atom or a ($C_1$-$C_3$) alkyl group,
or anyone of its pharmaceutically acceptable salt.

In certain aspects, the compounds described herein includes compounds of formula (Il)
wherein:
R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —NO$_2$ group, a —NR$_1$R$_2$ group, and a ($C_1$-$C_3$)alkoxy group,
n is 1 or 2,
n' is 1 or 2,
R' is a hydrogen atom or a group chosen among a ($C_1$-$C_3$) alkyl group, a halogen atom, a hydroxyl group, a —COOR$_1$ group, a —NO$_2$ group, a —NR$_1$R$_2$ group, a ($C_1$-$C_3$)alkoxy group and a —CN group,
R" is a hydrogen atom or a ($C_1$-$C_4$)alkyl group,
R$_1$ and R$_2$ are independently a hydrogen atom or a ($C_1$-$C_3$) alkyl group,
with the proviso that R and R' are not simultaneously a hydrogen atom,
or anyone of its pharmaceutically acceptable salt.

In certain aspects, the compounds described herein includes compounds of formula (Im)
wherein:
R independently represent a hydrogen atom, a halogen atom or a group chosen among a ($C_1$-$C_3$)alkyl group, a —CN group, a hydroxyl group, a —COOR$_1$ group, a ($C_1$-$C_3$)fluoroalkyl group, a ($C_1$-$C_3$)fluoroalkoxy group, a —$NO_2$ group, a —$NR_1R_2$ group, and a ($C_1$-$C_3$)alkoxy group, n is 1 or 2, n' is 1 or 2, R' is a hydrogen atom or a group chosen among a ($C_1$-$C_3$) alkyl group, a halogen atom, a hydroxyl group, a —$COOR_1$ group, a —$NO_2$ group, a —$NR_1R_2$ group, a ($C_1$-$C_3$)alkoxy group and a —CN group, R" is a hydrogen atom or a ($C_1$-$C_4$)alkyl group, $R_1$ and $R_2$ are independently a hydrogen atom or a ($C_1$-$C_3$) alkyl group, with the proviso that when n and n' are 1 and R is a hydrogen atom, R' is not a chlorine atom, or anyone of its pharmaceutically acceptable salt.

For simplification, the following compounds and their corresponding definitions are called "new compounds".

In certain aspects, the compounds described herein includes compounds of formula (Ia), as such,

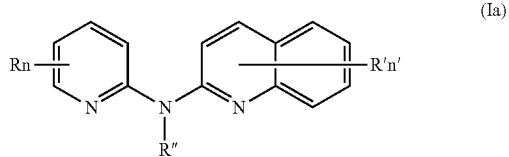
(Ia)

wherein:

R" and n are as defined in formula (Ia), n' is 1,

R independently represent a hydrogen atom, a halogen atom or a group chosen among a ($C_1$-$C_3$)alkyl group, a —CN group, a hydroxyl group, a —$COOR_1$ group, a ($C_1$-$C_3$)fluoroalkyl group, a —$NO_2$ group, a ($C_1$-$C_3$) fluoroalkoxy group and a ($C_1$-$C_3$)alkoxy group, R' is a hydrogen atom or a halogen atom or a group chosen among a ($C_1$-$C_3$)alkyl group, a —$COOR_1$ group, and a —CN group, $R_1$ is a hydrogen atom or a ($C_1$-$C_3$)alkyl group:

with the proviso that when R and R' are not simultaneously a hydrogen atom, when n is 1, R is not a methyl group in the ortho or para positions with respect to Z, Z being N, when R' is a hydrogen atom, R is not a bromine atom or a chlorine atom, when R is a hydrogen atom, R' is not a methyl or ethyl group, a —COOH group, a $COOC_2H_5$ group or a bromine atom, said bromine atom being in the ortho position with respect to the bond linked to NR", or one of its pharmaceutically acceptable salt.

Still according to this particular embodiment, the present invention more particularly focuses on compounds of formula (Ia), as such, wherein, R independently represents a hydrogen atom or a ($C_1$-$C_3$) alkyl group, R" is as defined in formula (Ia), R' is a hydrogen atom, a halogen atom, a ($C_1$-$C_3$)alkoxy group or a —$NO_2$ group, n' is 1, n is 1, with the proviso that when n is 1, R is not a methyl group in the ortho or para positions with respect to Z, Z being N, or one of its pharmaceutically acceptable salt.

In this aspect the compounds described herein can include compounds of formula (Ia'), as such,

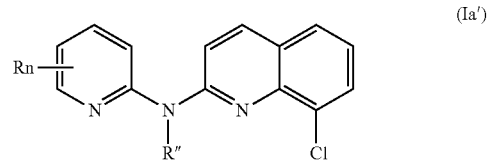
(Ia')

wherein,

R independently represents a hydrogen atom, a ($C_1$-$C_3$) alkyl group, a ($C_1$-$C_3$)fluoroalkyl group, a halogen atom or a hydroxyl group, R" is as defined in formula (Ia), n is 1 or 2, or one of its pharmaceutically acceptable salt.

In certain aspects, the compounds described herein includes compounds of formula (Ie)

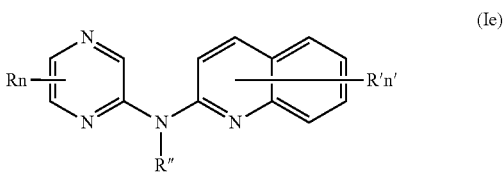
(Ie)

wherein:

R, R', R" n and n' are as defined in formula (I), with the proviso that when R is a hydrogen atom, R' is not a bromine atom, or one of its pharmaceutically acceptable salt.

The compounds described herein further relate to a compound of formula (Iq) as defined above, as such

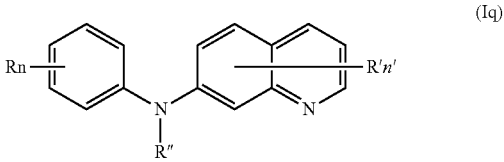
(Iq)

wherein:

R, R', R" and n' are as defined in formula (I), n is 1 or 2, with the proviso that R' and R are not simultaneously a hydrogen atom, when R' is a hydrogen atom, R is not a —$NO_2$ group or a —$NH_2$ group, when n is 2 and R' is a hydrogen atom, R is not a $COOC_2H_5$ group or a chlorine atom, or one of its pharmaceutically acceptable salt.

Still according to this particular embodiment, the compounds described herein include compounds of formula (Iq), as such, wherein R', R", n and n' are as defined in formula (I), and R is a ($C_1$-$C_3$)fluoroalkoxy group, or one of its pharmaceutically acceptable salt.

Still according to this particular embodiment, the compounds described herein include compounds of formula (Iq), as such, wherein R, R", n and n' are as defined in formula (I), and R' is a —$NR_1R_2$ group, $R_1$ and $R_2$ are independently a hydrogen atom or a ($C_1$-$C_3$) alkyl group, or one of its pharmaceutically acceptable salt.

Still according to this particular embodiment, the compounds described herein include compounds of formula (Iq), as such, wherein R, R", n and n' are as defined in formula (I), and R' is a morpholinyl group, a morpholino group or a N-methylpiperazinyl group, or one of its pharmaceutically acceptable salt.

In a further aspect, the compounds described herein includes a compound of formula (Iee) as defined above, as such

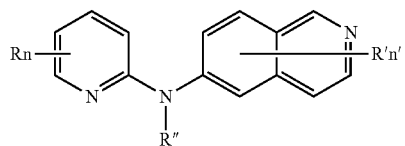

(Iee)

wherein:

R, R', R", n and n' are as defined in formula (I), or one of its pharmaceutically acceptable salt, with the exclusion of the following compound

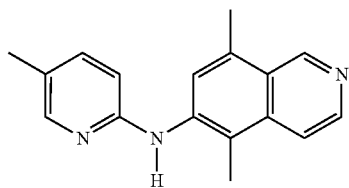

(148)

and with the exclusion of compounds wherein R is a —$NO_2$ group or a —$NH_2$ group when R' is a hydrogen or a methyl group.

Still according to this particular embodiment, the compounds described herein include compounds of formula (Iee), as such, wherein R', R", n and n' are as defined in formula (I), and R is a ($C_1$-$C_3$)fluoroalkyl group, or one of its pharmaceutically acceptable salt.

Among the compounds discussed above, compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts are of particular interest.

As discussed above, the compounds described herein include compounds (1), (2), (5)-(8), (10)-(16), (18), (21)-(44), (46)-(75), (77)-(84), (86)-(119), (121), (124)-(130), (132), (135)-(141), (143)-(147), (149)-(168) and their pharmaceutically acceptable salts, as such.

More preferably, compounds (143), (144), (149), (166), (167) and their pharmaceutically acceptable salts are of particular interest.

For example, the compounds described herein can include compounds (143), (144), (149), (166), (167) and their pharmaceutically acceptable salts, where the pharmaceutically acceptable salts include, but are not limited to, hydrobromide, tartrate, citrate, trifluoroacetate, ascorbate, hydrochloride, tartrate, triflate, maleate, mesylate, formate, acetate and fumarate.

In certain aspects, the compounds described herein include compounds (143) and (144) and their pharmaceutically acceptable salts, which include, but are not limited to, hydrobromide, tartrate, citrate, trifluoroacetate, ascorbate, hydrochloride, tartrate, triflate, maleate, mesylate, formate, acetate and fumarate.

The compounds described herein, e.g. compounds of formulae (Ia), (Ie), (Iq) and (Iee) and the specific compounds as listed above, are not only useful as agent for inhibiting, preventing or treating cancer but can also be useful for inhibiting, preventing or treating premature aging or progeria and for inhibiting, preventing or treating AIDS.

According to an aspect of the invention, the compounds may be useful to inhibit, prevent and/or treat diseases with premature aging and that are likely related to aberrant splicing of the nuclear lamin A gene. For example, such diseases may include Hutchinson Guilford Progeria Syndrome (HGPS), progeria, premature aging associated with HIV infection, muscular dystrophy, Charcot-Marie-Tooth disorder, Werner syndrome, but the diseases may also include atherosclerosis, insulin resistant type II diabetes, cataracts, osteoporosis and aging of the skin such as restrictive dermopathy.

The compounds described herein can be prepared by conventional methods of organic synthesis practiced by those skilled in the art. The general reaction sequences outlined below represent a general method useful for preparing the compounds of the present invention and are not meant to be limiting in scope or utility.

The compounds of general formula (I) can be prepared according to scheme 1 below.

Scheme 1

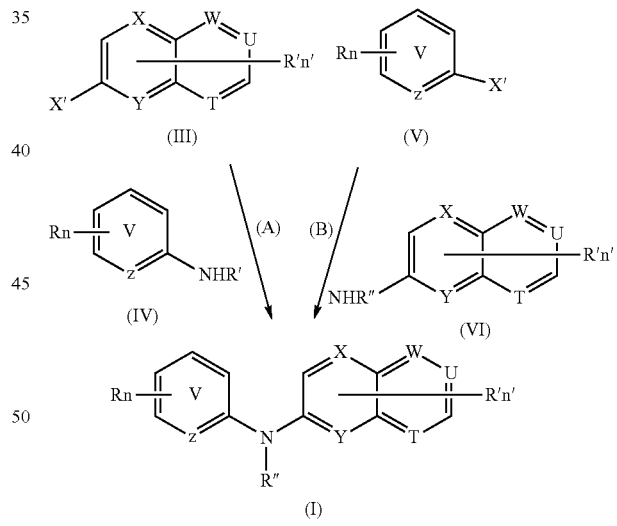

As appears in the scheme, two routes are available for recovering a compound of formula (I) according to the present invention.

The synthesis is based on a coupling reaction alternatively starting from a halogeno-bicycle of formula (III), wherein X, Y, W, T, U, n', R' and R" are as defined above and X' is a chlorine atom or a bromine atom or from a chloro-monocycle of formula (V), wherein Z, V, n and R are as defined above and X' is a chlorine atom or a bromine atom.

According to route (A), the compound of formula (III) is placed in a protic solvent such as tert-butanol. The compound of formula (IV) is then added in a molar ratio ranging from 1 to 1.5 with respect to the compound of formula (III) in presence of an inorganic base, such as $Cs_2CO_3$ or $K_2CO_3$ in a molar ratio ranging from 1 and 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (III), and in the presence of a catalyst, such as $Pd(OAc)_2$ or $Pd_2dba_3$ in an amount ranging from 2 mol % to 10 mol % relative to the total amount of compound of formula (III). The reaction mixture can then be heated at a temperature ranging from 80 to 120° C., for example at 90° C. and stirred for a time ranging form 15 to 25 hours, for example during 20 hours under inert gas and for example argon. The reaction mixture can be concentrated under reduced pressure.

According to route (B) the compound of formula (V) is placed in a protic solvent such as tert-butanol. The compound of formula (VI) is then added in a molar ratio ranging from 1 to 1.5 with respect to the compound of formula (V) in presence of an inorganic base, such as $Cs_2CO_3$ or $K_2CO_3$ in a molar ratio ranging from 1 to 2, in the presence of a diphosphine, such as Xantphos (4,5-Bis(diphenylphosphino)-9,9-dimethylxanthene) or X-Phos (2-Dicyclohexylphosphino-2',4',6'-triisopropylbiphenyl) in an amount ranging from 2 mol % to 10 mol % relative to the total amount of compound of formula (V), and in the presence of a catalyst, such as $Pd(OAc)_2$ or $Pd_2dba_3$ in an amount ranging from 2 mol % to 10 mol % relative to the total amount of compound of formula (V). The reaction mixture can then be heated at a temperature ranging from 80 to 120° C., for example at 90° C. and stirred for a time ranging form 15 to 25 hours, for example during 20 hours under inert gas and for example argon. The reaction mixture can be concentrated under reduced pressure.

The starting compounds of formula (III), (IV), (V) and (VI) are commercially available or can be prepared according to methods known to the person skilled in the art. The chemical structures and spectroscopic data of some compounds of formula (I) are illustrated respectively in the following Table I and Table II.

TABLE I

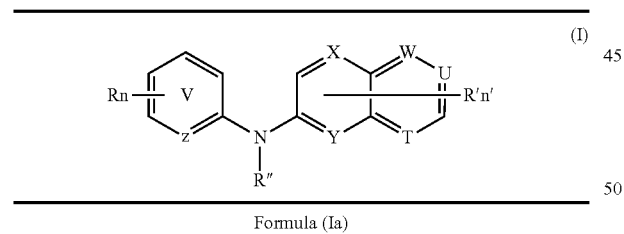

Formula (Ia)

| | |
|---|---|
| 1 | 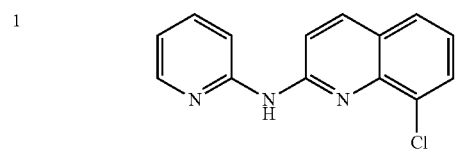 |
| 2 | 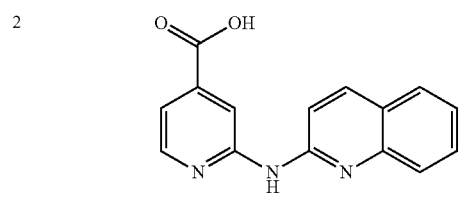 |
| 3 | 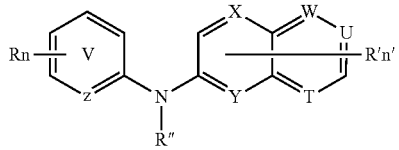 |
| 4 | 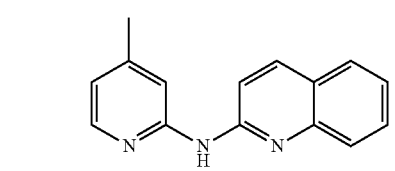 [SMILES: Cc1ccnc(Nc2ccc3ccccc3n2)c1] |
| 5 | 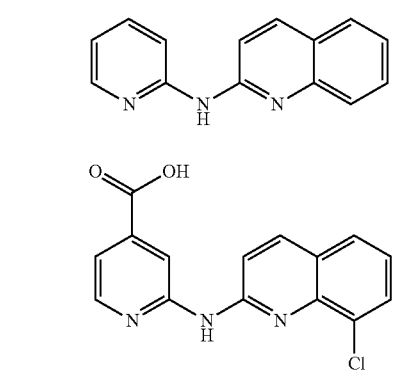 |
| 6 | 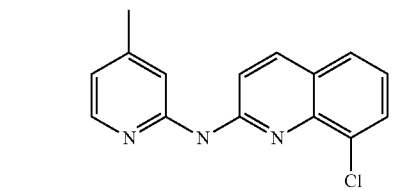 [SMILES: Cc1ccnc(Nc2ccc3cccc(Cl)c3n2)c1] |
| 7 | 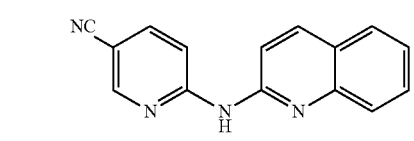 |
| 17 | 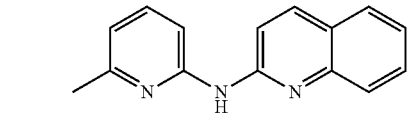 [SMILES: Cc1cccc(Nc2ccc3ccccc3n2)n1] |
| 18 | 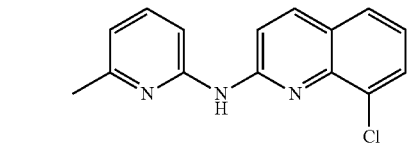 [SMILES: Cc1cccc(Nc2ccc3cccc(Cl)c3n2)n1] |
| 19 | 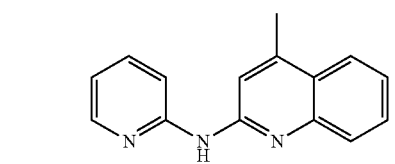 [SMILES: Cc1cc(Nc2ccccn2)nc2ccccc12] |

TABLE I-continued
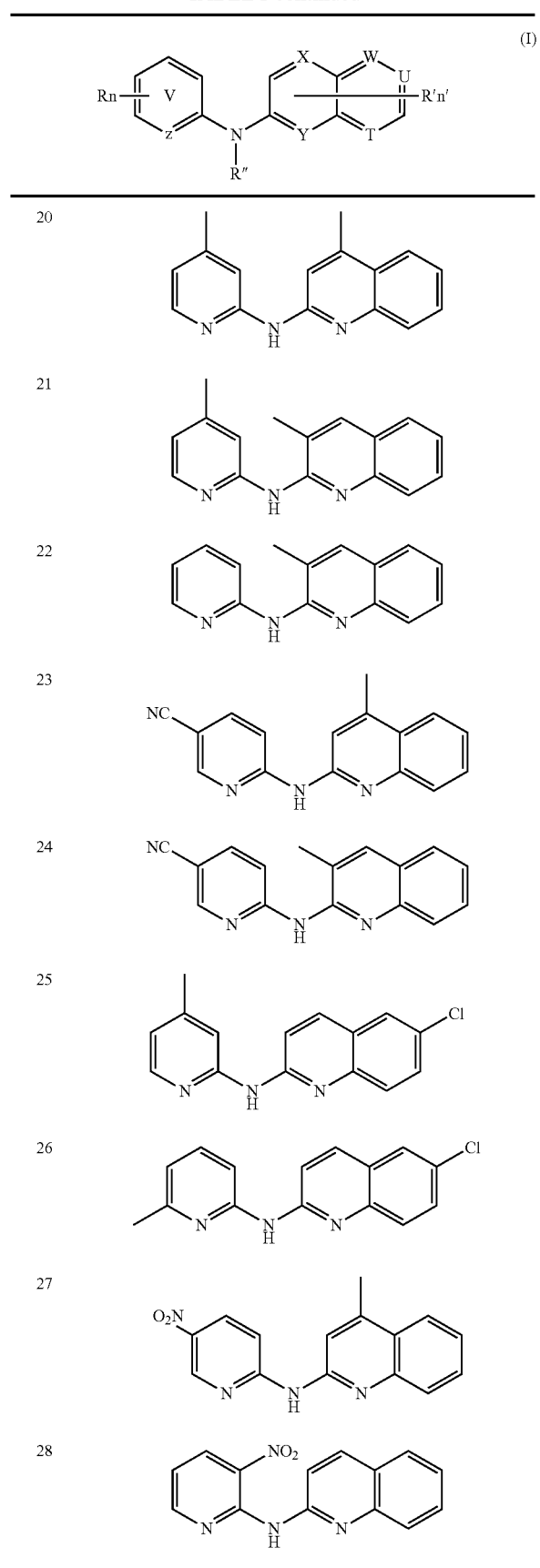
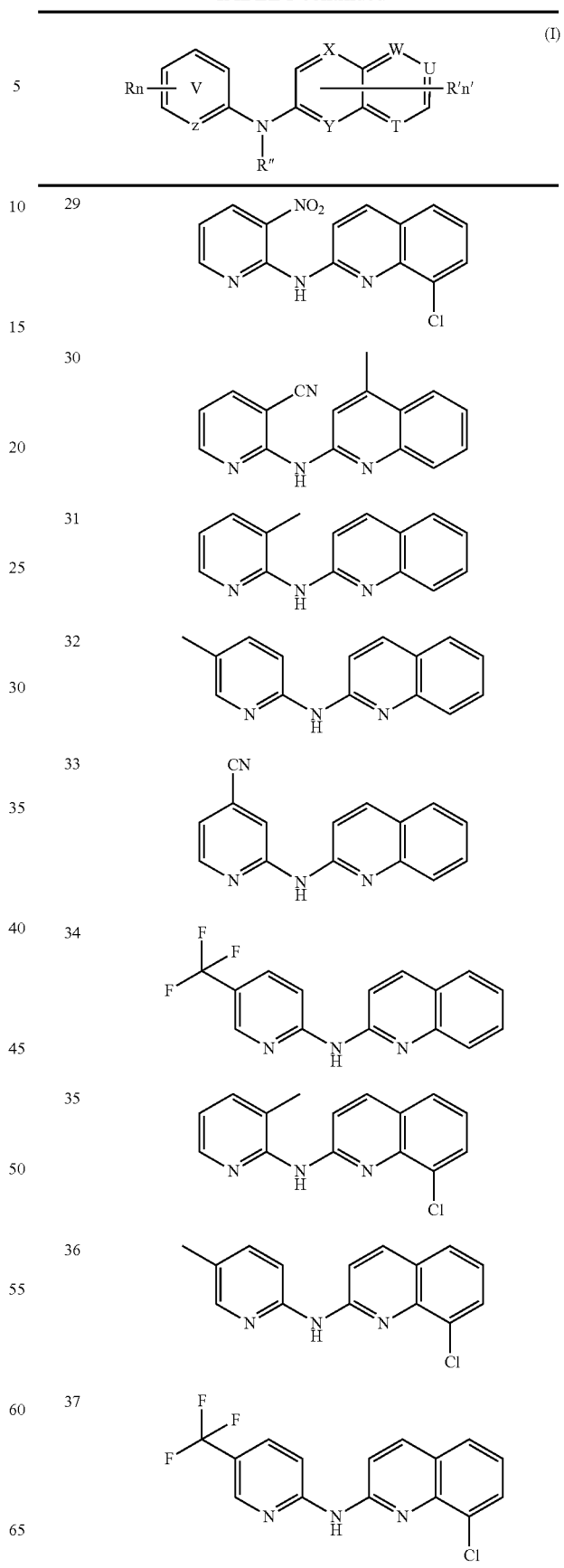

TABLE I-continued
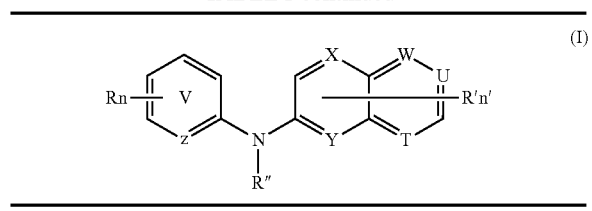
| 38 | 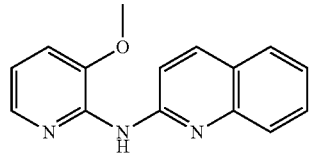 [SMILES: COc1cccnc1Nc1ccc2ccccc2n1] |
| 39 | 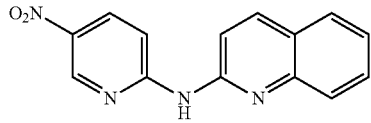 [SMILES: O=[N+]([O-])c1ccc(Nc2ccc3ccccc3n2)nc1] |
| 40 | 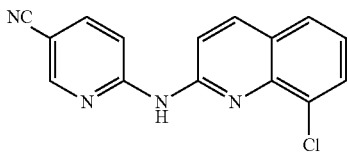 |
| 41 | 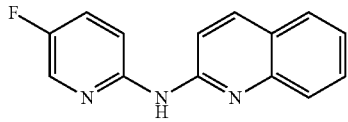 [SMILES: Fc1ccc(Nc2ccc3ccccc3n2)nc1] |
| 42 |  |
| 43 | 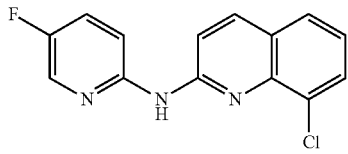 [SMILES: Fc1ccc(Nc2ccc3cccc(Cl)c3n2)nc1] |
| 44 | 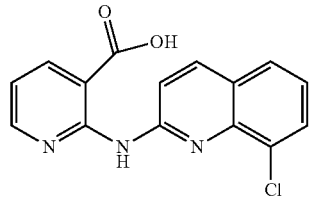 [SMILES: O=C(O)c1cccnc1Nc1ccc2cccc(Cl)c2n1] |
| 45 | 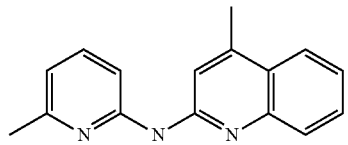 [SMILES: Cc1cccc(Nc2cc(C)c3ccccc3n2)n1] |
| 46 | 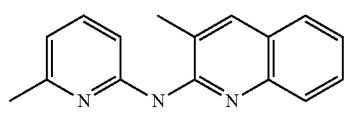 [SMILES: Cc1cccc(Nc2nc3ccccc3cc2C)n1] |
TABLE I-continued
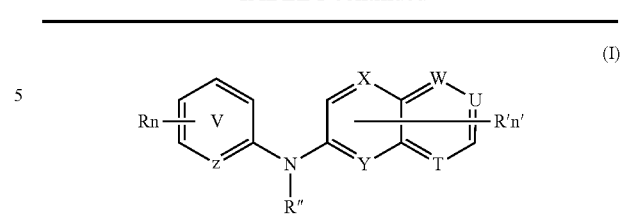
| 47 | 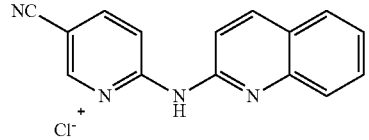 [SMILES: N#Cc1ccc(Nc2ccc3ccccc3n2)nc1 ; Cl] |
| 48 | 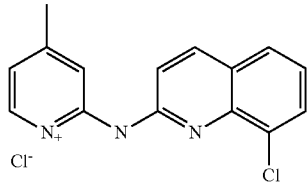 [SMILES: Cc1cc[nH+]c(Nc2ccc3cccc(Cl)c3n2)c1 ; [Cl-]] |
| 49 | 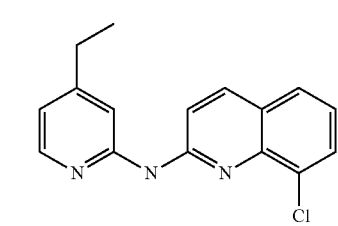 [SMILES: CCc1ccnc(Nc2ccc3cccc(Cl)c3n2)c1] |
| 50 | 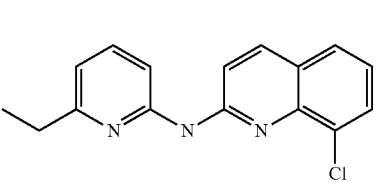 [SMILES: CCc1cccc(Nc2ccc3cccc(Cl)c3n2)n1] |
| 51 | 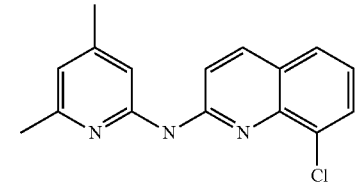 [SMILES: Cc1cc(C)nc(Nc2ccc3cccc(Cl)c3n2)c1] |
| 52 | 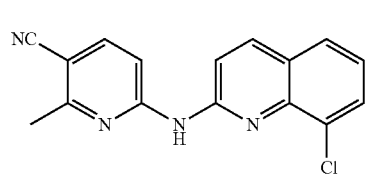 [SMILES: Cc1nc(Nc2ccc3cccc(Cl)c3n2)ccc1C#N] |
| 53 | 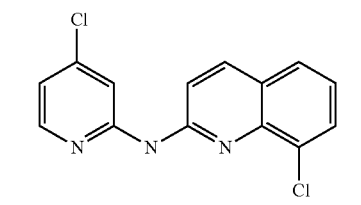 [SMILES: Clc1ccnc(Nc2ccc3cccc(Cl)c3n2)c1] |

TABLE I-continued
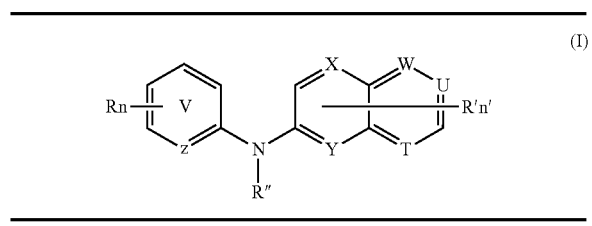
| 54 | 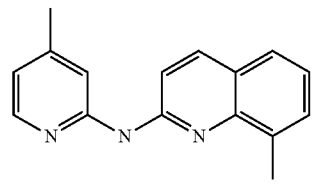 [SMILES: Cc1ccnc(Nc2ccc3cccc(C)c3n2)c1] |
| 55 | 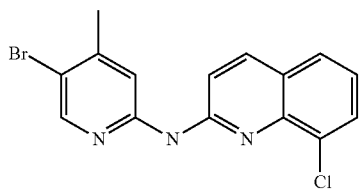 [SMILES: Cc1cc(Nc2ccc3cccc(Cl)c3n2)ncc1Br] |
| 56 | 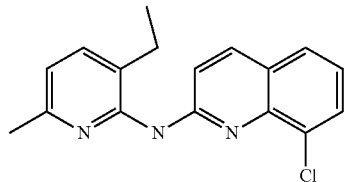 [SMILES: CCc1ccc(C)nc1Nc1ccc2cccc(Cl)c2n1] |
| 57 | 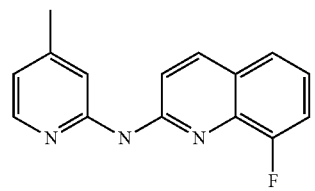 [SMILES: Cc1ccnc(Nc2ccc3cccc(F)c3n2)c1] |
| 58 | 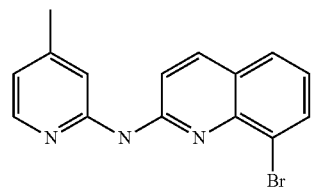 |
| 59 | 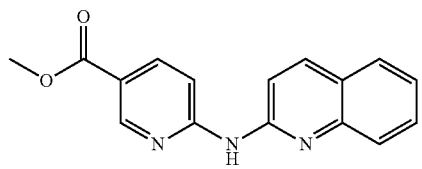 [SMILES: COC(=O)c1ccc(Nc2ccc3ccccc3n2)nc1] |
| 60 | 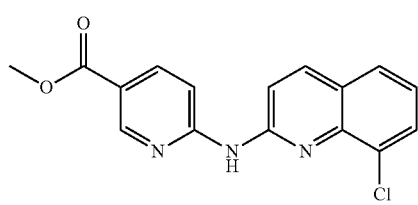 [SMILES: COC(=O)c1ccc(Nc2ccc3cccc(Cl)c3n2)nc1] |
TABLE I-continued
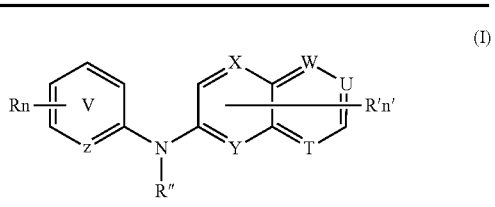
| 61 | 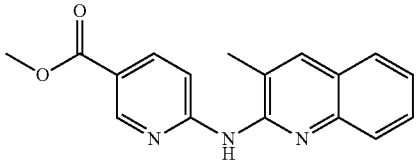 [SMILES: COC(=O)c1ccc(Nc2nc3ccccc3cc2C)nc1] |
| 62 | 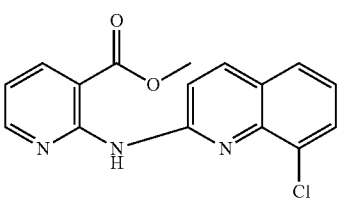 [SMILES: COC(=O)c1cccnc1Nc1ccc2cccc(Cl)c2n1] |
| 63 | 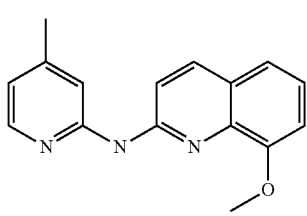 [SMILES: COc1cccc2ccc(Nc3cc(C)ccn3)nc12] |
| 64 | 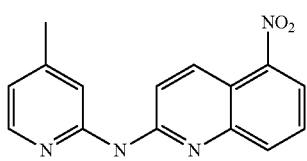 |
| 65 | 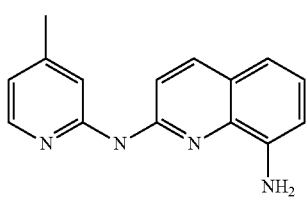 |
| 66 | 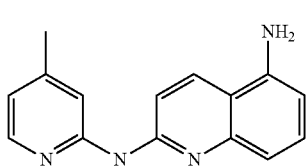 [SMILES: Cc1ccnc(Nc2ccc3c([N+](=O)[O-])cccc3n2)c1] |
| 67 | 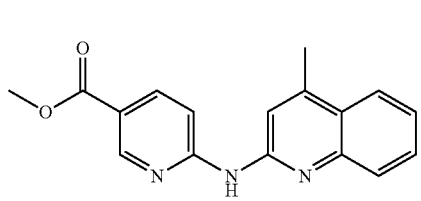 [SMILES: COC(=O)c1ccc(Nc2cc(C)c3ccccc3n2)nc1] |

TABLE I-continued
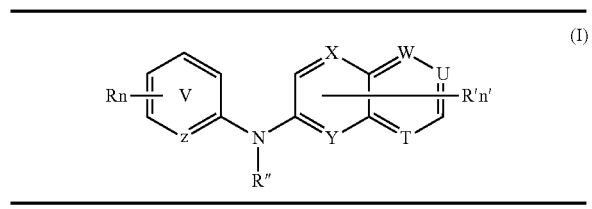
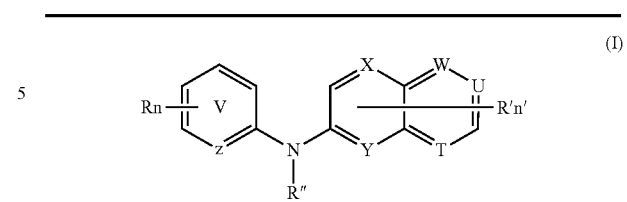

TABLE I-continued

| # | Structure |
|---|---|
| 79 | 4-methoxyphenyl-NH-(3-methylquinolin-2-yl) |
| 80 | 4-(trifluoromethoxy)phenyl-NH-(3-methylquinolin-2-yl) |
| 81 | 4-(dimethylamino)phenyl-NH-(3-methylquinolin-2-yl) |
| 82 | 4-(trifluoromethoxy)-2-methylphenyl-NH-quinolin-2-yl |
| 83 | 3-(trifluoromethoxy)phenyl-NH-quinolin-2-yl |
| 84 | 2-(trifluoromethoxy)phenyl-NH-quinolin-2-yl |
| 85 | 4-nitrophenyl-NH-quinolin-2-yl |
| 86 | 3-fluorophenyl-NH-quinolin-2-yl |
| 87 | 3-(trifluoromethoxy)phenyl-NH-(8-chloroquinolin-2-yl) |
| 88 | 3-fluorophenyl-NH-(8-chloroquinolin-2-yl) |
| 89 | 4-(trifluoromethoxy)phenyl-NH-quinolinium chloride |
| 90 | 4-(trifluoromethoxy)phenyl-NH-(8-chloroquinolin-2-yl) |
| 91 | 4-(trifluoromethoxy)-2-methylphenyl-NH-(3-methylquinolin-2-yl) |
| 92 | 3-(trifluoromethoxy)phenyl-NH-(3-methylquinolin-2-yl) |
| 93 | 2-(trifluoromethoxy)phenyl-NH-(3-methylquinolin-2-yl) |
| 94 | 4-(trifluoromethoxy)-2-methylphenyl-NH-(8-chloroquinolin-2-yl) |
| 95 | 4-(trifluoromethoxy)phenyl-NH-(3-methylquinolinium) chloride |

TABLE I-continued
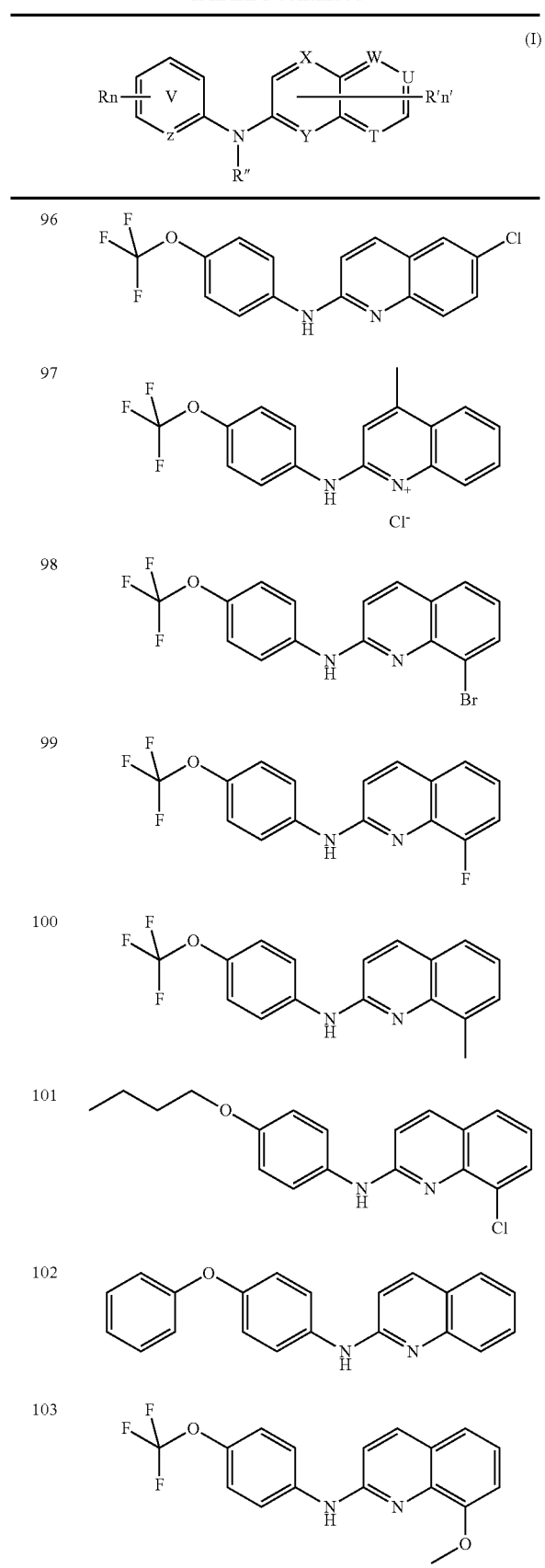
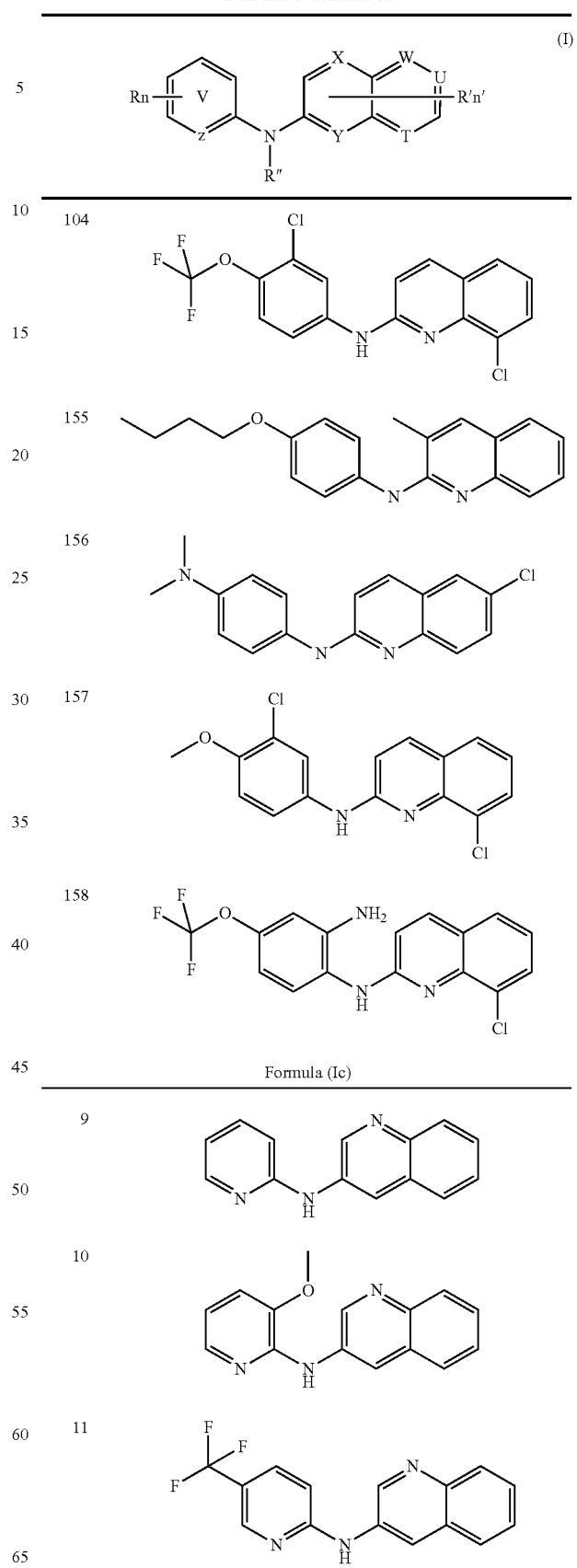

TABLE I-continued
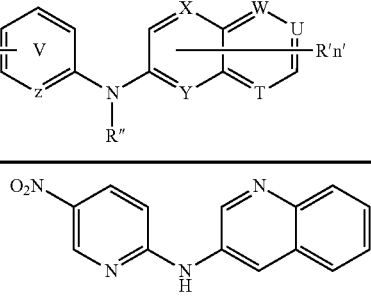
| 12 | 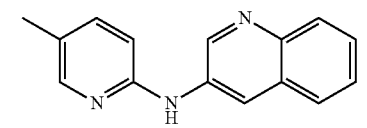 [SMILES: Cc1ccc(Nc2cnc3ccccc3c2)nc1] |
| 13 | 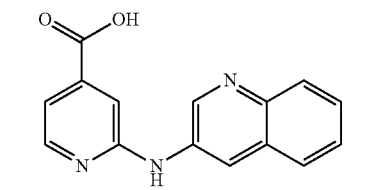 [SMILES: O=C(O)c1ccnc(Nc2cnc3ccccc3c2)c1] |
| 14 | 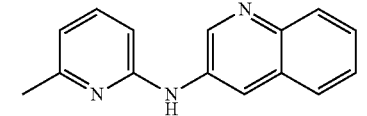 [SMILES: Cc1cccc(Nc2cnc3ccccc3c2)n1] |
| 105 | 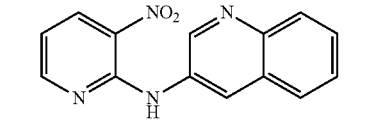 [SMILES: O=[N+]([O-])c1cccnc1Nc1cnc2ccccc2c1] |
| 106 | 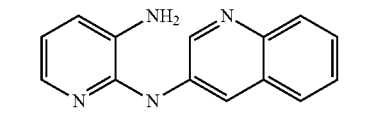 [SMILES: Nc1cccnc1Nc1cnc2ccccc2c1] |
| 159 | 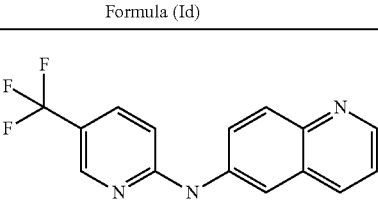 |
Formula (Id)
| 15 | 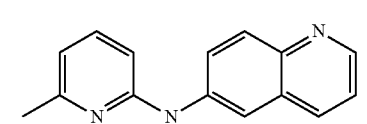 |
| 16 | 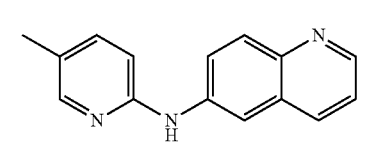 [SMILES: Cc1ccc(Nc2ccc3ncccc3c2)nc1] |
| 107 | 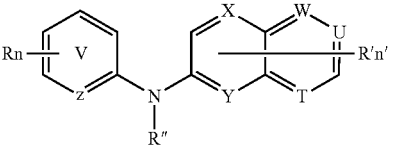 |
TABLE I-continued
| 108 | 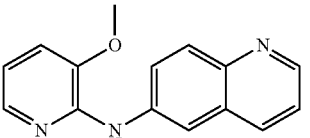 |
Formula (Ie)
| 109 | 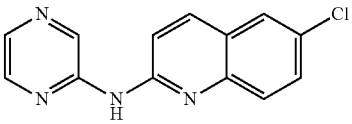 [SMILES: Clc1ccc2nc(Nc3cnccn3)ccc2c1] |
| 110 | 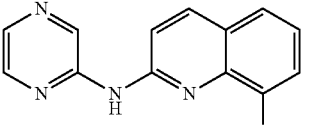 |
| 111 | 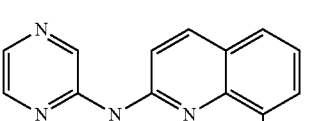 |
| 112 | 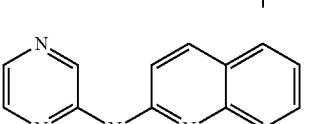 |
| 113 | 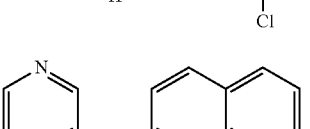 |
| 114 | 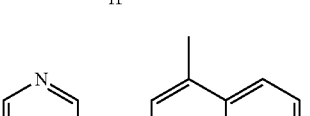 |
| 115 | 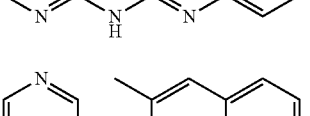 |
| 116 | 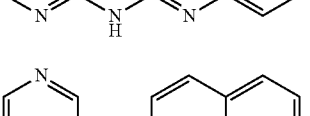 |

TABLE I-continued

| # | Structure |
|---|---|
| 117 | Formula (If) |
| 118 | Formula (Ig) |
| 119 | |
| 120 | Formula (Ih) |
| 121 | Formula (Ii) |
| 122 | |
| 123 | Formula (Ij) |
| 124 | |
| 125 | |
| 126 | |
| 127 | Formula (Ik) |
| 128 | |
| 129 | |
| 130 | Formula (Il) |
| 131 | Formula (Im) |
| 132 | |

TABLE I-continued

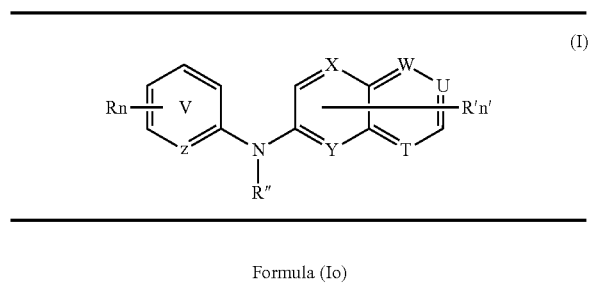

Formula (Io)

| 135 | (pyridin-2-yl)-quinoxalin-2-amine |
| 136 | 4-methylpyridin-2-yl quinoxalin-2-amine |
| 137 | 5-cyanopyridin-2-yl quinoxalin-2-amine |
| 138 | 6-methylpyridin-2-yl quinoxalin-2-amine |
| 139 | 4-methylpyridin-2-yl 3-(trifluoromethyl)quinoxalin-2-amine |
| 140 | 3,5-dichloro-4-methylpyridin-2-yl quinoxalin-2-amine |
| 141 | 4-methyl-3-nitropyridin-2-yl quinoxalin-2-amine |
| 160 | 4-methylpyridin-2-yl 6-chloroquinoxalin-2-amine |
| 161 | 4-ethylpyridin-2-yl quinoxalin-2-amine |
| 162 | 5-bromo-4-methylpyridin-2-yl quinoxalin-2-amine |
| 163 | 4,6-dimethylpyridin-2-yl quinoxalin-2-amine |
| 164 | 4-(hydroxymethyl)pyridin-2-yl quinoxalin-2-amine |
| 165 | 4-methyl-5-nitropyridin-2-yl quinoxalin-2-amine |

Formula (Ip)

| 142 | pyrimidin-2-yl quinoxalin-2-amine |

Formula (Iq)

| 143 | N,N-dimethyl-7-(4-(trifluoromethoxy)phenylamino)quinolin-4-amine |

TABLE I-continued
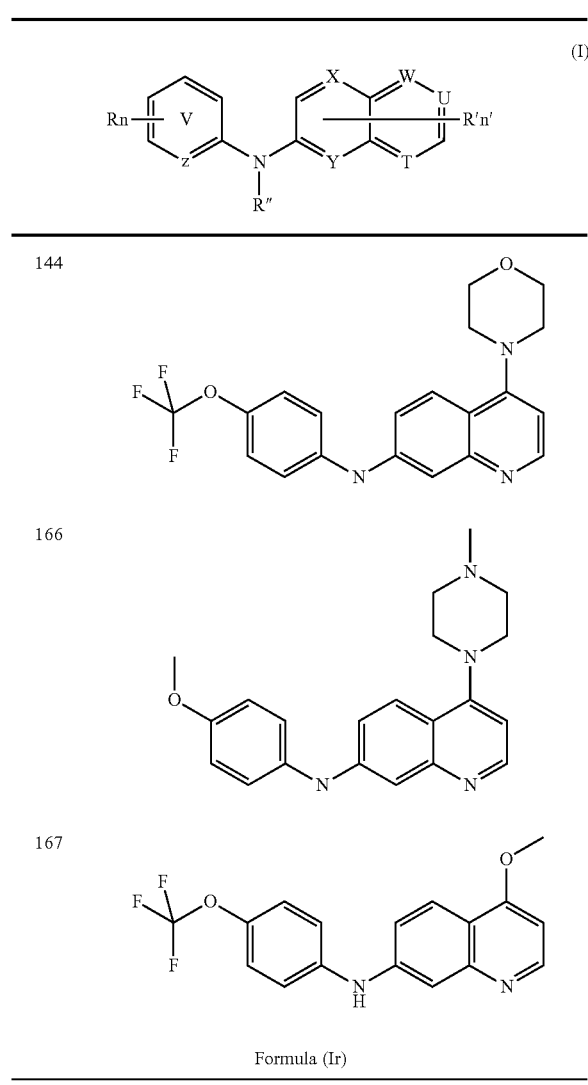
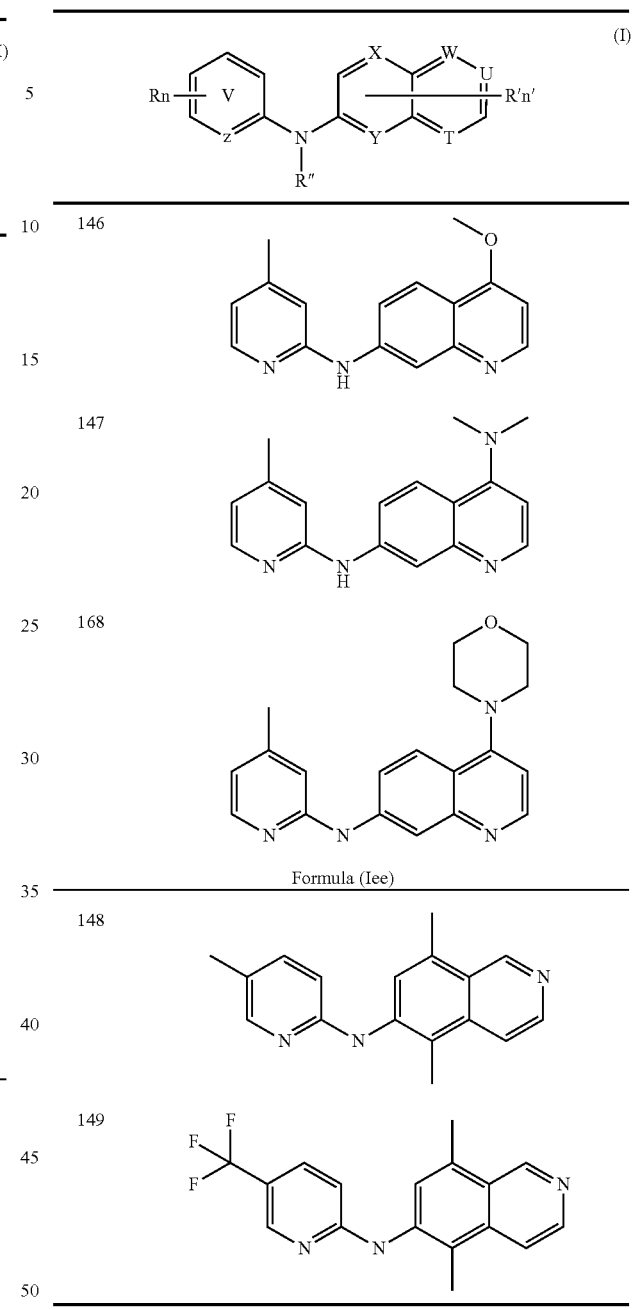
TABLE II
| Ex | Characterizations |
|---|---|
| 1 | MS (ESI) [M + H]⁺ = 256 |
| 2 | ¹H NMR (300 MHz, D₂O) δ 8.31 (d, J = 5.1, 1H), 8.21 (d, J = 9.3, 1H), 7.60 (d, J = 7.5, 3H), 7.34 (dd, J = 6.2, 15.6, 2H), 7.18 (s, 1H), 6.99 (d, J = 9.1, 1H) MS (ESI) [M + H]⁺ = 266 |
| 5 | MS (ESI) [M + H]⁺ = 300 |
| 6 | ¹H NMR (300 MHz, DMSO) δ 10.23 (s, 1H), 8.96 (s, 1H), 8.18 (d, J = 8.8, 2H), 7.78 (dd, J = 7.7, 13.7, 2H), 7.46 (d, J = 8.9, 1H), 7.31 (t, J = 7.8, 1H), 6.86 (d, J = 4.3, 1H), 2.37 (s, 3H). ¹³C NMR (75 MHz, DMSO) δ 153.63, 153.61, 148.37, 147.32, 142.65, 137.52, 129.68, 129.47, 126.82, 125.06, 123.26, 118.36, 115.10, 113.31, 21.24. MS (ESI) [M + H]⁺ = 270 |
| 7 | ¹H NMR (300 MHz, DMSO) δ 10.71 (s, 1H), 8.71 (d, J = 1.4, 1H), 8.62 (d, J = 8.9, 1H), 8.24 (d, J = 8.9, 1H), 8.17 (dd, J = 1.9, 8.9, 1H), 7.89-7.74 (m, 2H), 7.66 |

TABLE II-continued

| Ex | Characterizations |
|---|---|
| | (dd, J = 7.9, 14.2, 2H), 7.42 (t, J = 7.3, 1H).<br>$^{13}$C NMR (75 MHz, DMSO) δ 156.09, 152.40, 152.11, 146.24, 141.07, 137.83, 129.87, 127.67, 126.78, 124.50, 124.21, 118.04, 114.49, 111.67, 100.12.<br>MS (ESI) [M + H]$^+$ = 247 |
| 8 | $^1$H NMR (300 MHz, CDCl$_3$) δ 7.92 (d, J = 8.9, 1H), 7.79 (d, J = 8.4, 1H), 7.65 (t, J = 7.7, 3H), 7.59 (dd, J = 7.1, 8.3, 1H), 7.31 (t, J = 7.0, 1H), 7.20 (d, J = 8.5, 2H), 6.88 (d, J = 8.9, 1H), 6.80 (s, 1H)<br>$^{13}$C NMR (75 MHz, CDCl$_3$) δ 153.88, 147.62, 144.35, 139.26, 138.11, 130.13, 127.65, 127.12, 124.43, 123.70, 122.20, 120.95, 112.25.<br>MS (ESI) [M + H]$^+$ = 305 |
| 10 | $^1$H NMR (300 MHz, CDCl$_3$) δ 9.10 (d, J = 2.5, 1H), 8.83 (d, J = 2.6, 1H), 8.02 (d, J = 7.9, 1H), 7.94 (dd, J = 1.3, 5.0, 1H), 7.85-7.79 (m, 1H), 7.52 (pd, J = 1.5, 6.9, 2H), 7.33 (s, 1H), 7.04 (dd, J = 1.2, 7.9, 1H), 6.81 (dd, J = 5.1, 7.9, 1H), 3.95 (s, 3H) |
| 11 | MS (ESI) [M + H]$^+$ = 290 |
| 12 | $^1$H NMR (300 MHz, CDCl$_3$) δ 9.18 (d, J = 2.7, 1H), 8.86 (d, J = 2.5, 1H), 8.56 (d, J = 2.3, 1H), 8.33 (dd, J = 2.7, 9.2, 1H), 8.08 (d, J = 8.5, 1H), 7.83 (d, J = 8.5, 1H), 7.71-7.63 (m, 2H), 7.57 (t, J = 7.4, 2H), 6.82 (d, J = 9.1, 1H) |
| 13 | $^1$H NMR (300 MHz, CDCl$_3$) δ 8.83 (d, J = 2.6, 1H), 8.37 (d, J = 2.3, 1H), 8.00 (d, J = 8.2, 1H), 7.71 (d, J = 7.7, 1H), 7.59-7.51 (m, 1H), 7.46 (dd, J = 7.3, 15.1, 2H), 6.71 (d, J = 8.3, 1H), 6.67 (d, J = 7.4, 1H), 2.49 (s, 3H)<br>$^{13}$C NMR (75 MHz, CDCl$_3$) δ 157.13, 154.59, 145.81, 144.43, 138.78, 134.54, 129.22, 128.86, 127.41, 127.27, 121.48, 115.41, 106.50, 24.18.<br>MS (ESI) [M + H]$^+$ = 236 |
| 14 | MS (ESI) [M + H]$^+$ = 266 |
| 15 | MS (ESI) [M + H]$^+$ = 290 |
| 16 | $^1$H NMR (300 MHz, CDCl$_3$) δ 8.77 (dd, J = 1.5, 4.2, 1H), 8.04 (dd, J = 4.7, 8.7, 2H), 7.92 (d, J = 2.4, 1H), 7.59 (dd, J = 2.5, 9.1, 1H), 7.47 (t, J = 7.8, 1H), 7.35 (dd, J = 4.2, 8.3, 1H), 6.87 (s, 1H), 6.81 (d, J = 8.2, 1H), 6.70 (d, J = 7.4, 1H), 2.50 (s, 3H)<br>MS (ESI) [M + H]$^+$ = 236 |
| 18 | $^1$H NMR (300 MHz, CDCl$_3$) δ 8.53 (d, J = 59.9, 2H), 7.76 (d, J = 8.6, 1H), 7.58 (t, J = 8.3, 2H), 7.42 (d, J = 7.8, 1H), 7.09 (t, J = 7.7, 1H), 6.95 (d, J = 8.7, 1H), 6.71 (d, J = 7.3, 1H), 2.38 (s, 3H) |
| 21 | $^1$H NMR (300 MHz, CDCl$_3$) δ 8.78 (s, 1H), 8.13 (d, J = 5.1, 1H), 7.89 (d, J = 8.3, 1H), 7.79 (s, 1H), 7.63 (d, J = 8.0, 1H), 7.56 (d, J = 7.3, 1H), 7.38 (s, 1H), 7.33 (t, J = 7.5, 1H), 6.79 (d, J = 4.9, 1H), 2.44 (s, 6H) |
| 22 | $^1$H NMR (300 MHz, CDCl$_3$) δ 8.95 (d, J = 8.4, 1H), 8.28 (d, J = 5.7, 1H), 7.87 (d, J = 8.3, 1H), 7.78 (s, 1H), 7.76-7.70 (m, 1H), 7.62 (d, J = 8.0, 1H), 7.60-7.52 (m, 1H), 7.42 (s, 1H), 7.32 (t, J = 7.4, 1H), 6.95 (dd, J = 5.1, 6.5, 1H), 2.45 (s, 3H) |
| 23 | $^1$H NMR (300 MHz, CDCl$_3$) δ 8.64 (d, J = 8.4, 1H), 8.55 (d, J = 2.1, 1H), 8.03 (s, 1H), 7.90 (d, J = 8.5, 4H), 7.66 (t, J = 7.6, 1H), 7.44 (t, J = 7.6, 1H), 7.06 (s, 1H), 2.67 (s, 4H) |
| 24 | $^1$H NMR (300 MHz, CDCl$_3$) δ 9.09 (d, J = 8.9, 1H), 8.53 (d, J = 1.7, 1H), 7.94 (dd, J = 2.2, 8.9, 1H), 7.92-7.84 (m, 2H), 7.67 (d, J = 8.6, 2H), 7.65-7.58 (m, 1H), 7.40 (t, J = 7.4, 1H), 2.49 (s, 3H) |
| 25 | $^1$H NMR (300 MHz, CDCl$_3$) δ 8.16 (d, J = 5.2, 1H), 8.10 (s, 1H), 7.90 (d, J = 8.8, 1H), 7.79 (d, J = 9.0, 1H), 7.66 (d, J = 2.2, 1H), 7.55 (dd, J = 2.3, 8.9, 1H), 7.39 (d, J = 9.0, 1H), 6.79 (d, J = 5.2, 1H), 2.42 (s, 3H)<br>MS (ESI) [M + H]$^+$ = 270 |
| 26 | $^1$H NMR (300 MHz, CDCl$_3$) δ 8.06 (d, J = 8.3, 1H), 7.70 (d, J = 9.0, 1H), 7.64 (d, J = 8.9, 1H), 7.49 (t, J = 7.9, 2H), 7.40 (dd, J = 2.3, 8.9, 1H), 7.18 (d, J = 8.9, 1H), 6.68 (d, J = 7.4, 1H), 2.38 (s, 3H)<br>MS (ESI) [M + H]$^+$ = 270 |
| 27 | $^1$H NMR (300 MHz, CDCl$_3$) δ 9.17 (d, J = 2.5, 1H), 8.71 (s, 1H), 8.49 (dd, J = 2.6, 9.0, 1H), 7.99 (s, 1H), 7.93 (d, J = 8.9, 2H), 7.74-7.64 (m, 1H), 7.48 (dd, J = 4.2, 11.4, 1H), 7.09 (s, 1H), 2.71 (s, 3H) |
| 28 | $^1$H NMR (300 MHz, CDCl$_3$) δ 8.64-8.51 (m, 3H), 8.18 (d, J = 9.0, 1H), 7.93 (d, J = 8.4, 1H), 7.79 (d, J = 8.1, 1H), 7.73-7.64 (m, 1H), 7.51-7.41 (m, 1H), 7.00 (dd, J = 4.6, 8.2, 1H), 6.75 (dd, J = 4.6, 8.3, 0H) |
| 29 | $^1$H NMR (300 MHz, CDCl$_3$) δ 10.77 (s, 1H), 8.60 (s, 3H), 8.19 (d, J = 8.2, 1H), 7.76 (dd, J = 6.6, 25.5, 2H), 7.38 (d, J = 7.2, 1H), 7.04 (d, J = 4.4, 1H) |
| 30 | $^1$H NMR (300 MHz, CDCl$_3$) δ 8.46 (dd, J = 1.9, 5.0, 1H), 7.87 (dd, J = 2.0, 7.6, 1H), 7.82 (d, J = 7.3, 1H), 7.60 (t, J = 7.3, 2H), 7.43-7.33 (m, 1H), 6.90 (dd, J = 5.0, 7.6, 1H), 2.64 (s, 3H) |
| 31 | $^1$H NMR (300 MHz, CDCl$_3$) δ 8.44 (d, J = 9.1, 1H), 8.17 (d, J = 4.8, 1H), 8.03 (d, J = 9.1, 1H), 7.78 (d, J = 8.4, 1H), 7.68 (d, J = 8.0, 1H), 7.62-7.54 (m, 1H), 7.39 (d, J = 7.3, 1H), 7.32 (t, J = 7.5, 1H), 6.82 (dd, J = 5.0, 7.3, 1H), 2.31 (s, 3H)<br>MS (ESI) [M + H]$^+$ = 236 |
| 32 | $^1$H NMR (300 MHz, CDCl$_3$) δ 8.23 (d, J = 8.5, 1H), 8.10 (s, 1H), 7.91 (d, J = 8.9, 1H), 7.82 (d, J = 8.4, 1H), 7.62 (d, J = 8.3, 1H), 7.56 (d, J = 7.3, 1H), 7.50 (dd, J = 1.8, 8.5, 1H), 7.37-7.24 (m, 2H), 2.26 (s, 3H)<br>MS (ESI) [M + H]$^+$ = 236 |
| 33 | $^1$H NMR (300 MHz, CDCl$_3$) δ 8.87 (s, 1H), 8.32 (d, J = 5.0, 1H), 7.95 (d, J = 8.8, 1H), 7.84 (d, J = 8.3, 1H), 7.60 (dd, J = 7.4, 14.1, 2H), 7.32 (t, J = 7.5, 1H), 7.04 (dd, J = 5.0, 9.0, 2H)<br>MS (ESI) [M + H]$^+$ = 247 |

TABLE II-continued

| Ex | Characterizations |
|---|---|
| 34 | $^1$H NMR (300 MHz, CDCl$_3$) δ 8.52 (s, 1H), 8.45 (d, J = 8.6, 1H), 8.01 (d, J = 8.8, 1H), 7.87 (dd, J = 2.5, 8.5, 2H), 7.72-7.56 (m, 2H), 7.39 (d, J = 9.0, 2H)<br>MS (ESI) [M + H]$^+$ = 290 |
| 35 | $^1$H NMR (300 MHz, CDCl$_3$) δ 8.32 (d, J = 9.1, 1H), 8.07 (d, J = 4.8, 1H), 7.93 (d, J = 9.1, 1H), 7.59 (t, J = 7.9, 1H), 7.52 (d, J = 8.0, 1H), 7.36 (d, J = 7.2, 1H), 7.14 (t, J = 7.8, 1H), 6.77 (dd, J = 5.0, 7.3, 1H), 2.29 (s, 3H)<br>MS (ESI) [M + H]$^+$ = 270 |
| 36 | $^1$H NMR (300 MHz, CDCl$_3$) δ 8.70 (d, J = 7.2, 1H), 8.01 (s, 1H), 7.82 (d, J = 8.9, 1H), 7.62 (d, J = 7.6, 1H), 7.53 (dd, J = 1.8, 8.6, 1H), 7.46 (d, J = 7.9, 1H), 7.12 (t, J = 7.8, 1H), 7.05 (d, J = 8.8, 1H), 2.21 (s, 3H)<br>MS (ESI) [M + H]$^+$ = 270 |
| 37 | $^1$H NMR (300 MHz, CDCl$_3$) δ 9.08 (d, J = 8.5, 1H), 8.55 (s, 1H), 8.36 (s, 1H), 8.02 (d, J = 8.1, 2H), 7.77 (d, J = 7.2, 1H), 7.62 (d, J = 7.6, 1H), 7.35-7.24 (m, 1H), 7.12 (d, J = 8.8, 1H)<br>MS (ESI) [M + H]$^+$ = 324 |
| 38 | $^1$H NMR (300 MHz, CDCl$_3$) δ 8.69 (d, J = 9.1, 1H), 7.97 (d, J = 9.1, 1H), 7.80-7.74 (m, 1H), 7.70 (d, J = 8.4, 1H), 7.59 (d, J = 8.0, 1H), 7.54-7.45 (m, 1H), 7.22 (t, J = 7.5, 1H), 6.87 (d, J = 7.9, 1H), 6.68 (dd, J = 5.0, 7.9, 1H), 3.73 (s, 3H)<br>MS (ESI) [M + H]$^+$ = 252 |
| 39 | $^1$H NMR (300 MHz, CDCl$_3$) δ 8.57 (d, J = 29.4, 1H), 7.80 (d, J = 8.8, 1H), 7.66 (t, J = 6.7, 2H), 7.46 (d, J = 7.9, 1H), 7.14 (t, J = 7.8, 1H), 7.06 (d, J = 8.8, 1H), 6.79 (d, J = 7.3, 1H), 2.73 (dd, J = 7.6, 15.2, 2H), 1.28 (t, J = 7.7, 3H) |
| 40 | $^1$H NMR (300 MHz, DMSO) δ 9.75 (s, 1H), 9.12 (d, J = 2.3, 1H), 8.50 (d, J = 2.2, 1H), 8.48 (s, 1H), 8.13 (s, 1H), 7.83 (s, 1H), 7.80 (s, 1H), 7.64 (t, J = 7.7, 1H), 7.45 (t, J = 7.8, 1H) |
| 41 | $^1$H NMR (300 MHz, CDCl$_3$) δ 8.52 (dd, J = 2.8, 8.6, 1H), 8.35 (s, 1H), 8.15 (d, J = 2.3, 1H), 7.94 (d, J = 8.8, 1H), 7.84 (d, J = 8.2, 1H), 7.65 (d, J = 7.8, 1H), 7.59 (d, J = 7.2, 1H), 7.50-7.40 (m, 1H), 7.33 (t, J = 7.4, 1H), 7.11 (d, J = 8.9, 1H)<br>MS (ESI) [M + H]$^+$ = 240 |
| 42 | $^1$H NMR (300 MHz, CDCl$_3$) δ 8.55 (d, J = 6.8, 1H), 8.01 (d, J = 8.9, 2H), 7.82 (dd, J = 9.1, 17.3, 2H), 7.69 (d, J = 8.0, 1H), 7.63 (t, J = 7.6, 1H), 7.37 (t, J = 7.5, 1H), 7.32-7.18 (m, 2H)<br>MS (ESI) [M + H]$^+$ = 290 |
| 43 | $^1$H NMR (300 MHz, DMSO) δ 10.41 (s, 1H), 9.08 (dd, J = 4.1, 9.3, 1H), 8.31 (d, J = 2.9, 1H), 8.20 (d, J = 8.9, 1H), 7.88-7.70 (m, 3H), 7.44 (d, J = 8.9, 1H), 7.32 (t, J = 7.8, 1H)<br>$^{13}$C NMR (75 MHz, DMSO) δ 156.30, 153.32, 153.04, 150.17, 142.55, 137.73, 135.06, 134.74, 129.58, 129.49, 126.86, 125.29, 125.14, 125.04, 123.36, 114.91, 113.36.<br>MS (ESI) [M + H]$^+$ = 274 |
| 44 | $^1$H NMR (300 MHz, CDCl$_3$) δ 11.09 (s, 1H), 8.78 (d, J = 9.0, 1H), 8.42 (dd, J = 1.9, 4.7, 1H), 8.28 (dd, J = 1.9, 7.8, 1H), 8.11 (d, J = 9.1, 1H), 7.73 (d, J = 7.5, 1H), 7.65 (d, J = 8.1, 1H), 7.27 (d, J = 6.4, 9.2, 1H), 6.88 (dd, J = 4.8, 7.8, 1H)<br>MS (ESI) [M + H]$^+$ = 300 |
| 46 | $^1$H NMR (300 MHz, CDCl$_3$) δ 8.59 (d, J = 8.3, 1H), 7.73 (d, J = 8.3, 1H), 7.57 (s, 1H), 7.51 (t, J = 7.9, 1H), 7.43 (t, J = 9.2, 2H), 7.17 (d, J = 7.4, 1H), 6.67 (d, J = 7.4, 1H), 2.36 (s, 3H), 2.28 (s, 3H) |
| 47 | $^1$H NMR (300 MHz, MeOD) δ 8.99 (s, 1H), 8.76 (d, J = 9.2, 1H), 8.32 (d, J = 8.7, 1H), 8.22 (d, J = 8.6, 1H), 8.11 (d, J = 7.8, 1H), 8.01 (t, J = 7.1, 1H), 7.76 (t, J = 7.4, 1H), 7.55-7.43 (m, 2H)<br>MS (ESI) [M + H]$^+$ = 247 |
| 48 | $^1$H NMR (300 MHz, MeOD) δ 8.48 (d, J = 9.1, 1H), 8.40 (d, J = 6.7, 1H), 7.94 (d, J = 8.4, 1H), 7.90 (d, J = 7.8, 1H), 7.54 (t, J = 8.0, 1H), 7.38 (d, J = 8.6, 1H), 7.30 (s, 2H), 2.58 (s, 3H)<br>MS (ESI) [M + H]$^+$ = 270 |
| 49 | $^1$H NMR (300 MHz, CDCl$_3$) δ 9.34 (s, 1H), 8.95 (s, 1H), 8.21 (d, J = 5.1, 1H), 7.87 (d, J = 8.9, 1H), 7.71 (d, J = 7.5, 1H), 7.52 (d, J = 7.9, 1H), 7.19 (t, J = 7.8, 1H), 7.05 (d, J = 8.9, 1H), 6.84 (d, J = 5.1, 1H), 2.76 (q, J = 7.6, 2H), 1.37 (t, J = 7.6, 3H) |
| 50 | $^1$H NMR (300 MHz, CDCl$_3$) δ 8.57 (d, J = 29.4, 1H), 7.80 (d, J = 8.8, 1H), 7.66 (t, J = 6.7, 2H), 7.46 (d, J = 7.9, 1H), 7.14 (t, J = 7.8, 1H), 7.06 (d, J = 8.8, 1H), 6.79 (d, J = 7.3, 1H), 2.73 (dd, J = 7.6, 15.2, 2H), 1.28 (t, J = 7.7, 3H) |
| 51 | $^1$H NMR (300 MHz, CDCl$_3$) δ 8.64 (s, 1H), 8.06 (s, 1H), 7.89 (d, J = 8.7, 1H), 7.71 (d, J = 7.4, 1H), 7.54 (d, J = 7.8, 1H), 7.20 (t, J = 7.7, 1H), 7.02 (d, J = 8.8, 1H), 6.67 (s, 1H), 2.43 (s, 3H), 2.39 (s, 3H)<br>$^{13}$C NMR (75 MHz, CDCl$_3$) δ 156.15, 153.17, 152.82, 150.16, 143.70, 137.92, 131.34, 129.89, 126.49, 125.47, 123.43, 118.62, 114.47, 111.02, 24.13, 21.70.<br>MS (ESI) [M + H]$^+$ = 284 |
| 52 | $^1$H NMR (300 MHz, CDCl$_3$) δ 8.89 (d, J = 8.8, 1H), 8.05 (d, J = 8.8, 1H), 8.01 (s, 1H), 7.93 (d, J = 8.8, 1H), 7.79 (d, J = 7.5, 1H), 7.64 (d, J = 8.0, 1H), 7.32 (t, J = 7.8, 1H), 7.13 (d, J = 8.8, 1H), 2.67 (s, 3H) |
| 53 | $^1$H NMR (300 MHz, CDCl$_3$) δ 9.27 (s, 1H), 8.33 (d, J = 5.7, 1H), 8.13 (d, J = 5.2, 1H), 8.00 (d, J = 8.8, 1H), 7.76 (d, J = 7.4, 1H), 7.60 (d, J = 8.0, 1H), 7.29 (d, J = 7.9, 1H), 7.07 (d, J = 8.9, 1H), 6.97 (d, J = 4.8, 1H) |
| 54 | MS (ESI) [M + H]$^+$ = 250 |
| 55 | $^1$H NMR (300 MHz, CDCl$_3$) δ 8.19 (s, 1H), 7.90 (d, J = 9.0, 1H), 7.63 (d, J = 7.5, 1H), 7.52 (d, J = 7.9, 1H), 7.33 (d, J = 7.4, 1H), 7.14 (t, J = 7.8, 1H), 6.69 (d, J = 7.5, 1H), 2.70 (dd, J = 7.3, 14.8, 2H), 2.47 (s, 3H), 1.26 (t, J = 7.7, 3H) |

TABLE II-continued

| Ex | Characterizations |
|---|---|
| 56 | $^1$H NMR (300 MHz, CDCl$_3$) δ 8.20 (s, 1H), 7.90 (d, J = 9.0, 1H), 7.63 (d, J = 7.5, 1H), 7.52 (d, J = 7.9, 1H), 7.33 (d, J = 7.4, 1H), 7.14 (t, J = 7.8, 1H), 6.69 (d, J = 7.5, 1H), 2.70 (dd, J = 7.3, 14.8, 2H), 2.47 (s, 3H), 1.25 (dd, J = 7.5, 15.5, 3H) |
| 57 | MS (ESI) [M + H]$^+$ = 253 |
| 58 | MS (ESI) [M + H]$^+$ = 314-316 |
| 59 | $^1$H NMR (300 MHz, CDCl$_3$) δ 8.91 (d, J = 1.7, 1H), 8.46 (d, J = 8.8, 1H), 8.28 (dd, J = 2.0, 8.8, 1H), 8.23 (s, 1H), 8.03 (d, J = 8.8, 1H), 7.88 (d, J = 8.3, 1H), 7.70 (d, J = 8.0, 1H), 7.67-7.58 (m, 1H), 7.38 (t, J = 7.4, 1H), 7.32 (d, J = 8.8, 2H), 3.91 (s, 3H) |
| 60 | $^1$H NMR (300 MHz, CDCl$_3$) δ 8.94 (d, J = 8.9, 1H), 8.91 (d, J = 1.8, 1H), 8.37 (dd, J = 2.2, 8.8, 1H), 8.04 (d, J = 8.9, 2H), 7.77 (d, J = 7.5, 1H), 7.62 (d, J = 7.2, 1H), 7.30 (t, J = 7.8, 2H), 7.19 (d, J = 8.8, 2H), 3.92 (s, 3H) |
| 61 | $^1$H NMR (300 MHz, CDCl$_3$) δ 8.96 (d, J = 8.8, 1H), 8.85 (d, J = 1.3, 1H), 8.28 (d, J = 9.9, 1H), 7.84 (d, J = 8.0, 1H), 7.77 (s, 1H), 7.65 (s, 1H), 7.59 (d, J = 8.4, 2H), 7.53 (d, J = 8.4, 1H), 7.31 (t, J = 7.4, 1H), 3.88 (s, 4H), 2.42 (s, 4H)<br>MS (ESI) [M + H]$^+$ = 294 |
| 62 | $^1$H NMR (300 MHz, CDCl$_3$) δ 11.02 (s, 1H), 8.75 (d, J = 9.2, 1H), 8.44 (d, J = 3.7, 1H), 8.31 (d, J = 7.9, 1H), 8.10 (d, J = 9.0, 1H), 7.72 (d, J = 7.5, 1H), 7.64 (d, J = 8.2, 1H), 7.27 (d, J = 8.1, 1H), 6.88 (dd, J = 4.7, 7.8, 1H), 3.97 (s, 3H)<br>MS (ESI) [M + H]$^+$ = 314 |
| 63 | MS (ESI) [M + H]$^+$ = 266 |
| 64 | $^1$H NMR (300 MHz, DMSO) δ 10.38 (s, 1H), 8.56 (s, 1H), 8.28 (d, J = 9.1, 1H), 8.20-8.03 (m, 3H), 7.50 (d, J = 8.7, 1H), 7.45 (d, J = 8.0, 1H), 6.88 (d, J = 4.4, 1H), 2.37 (s, 3H) |
| 65 | MS (ESI) [M + H]$^+$ = 314-316 |
| 66 | MS (ESI) [M + H]$^+$ = 250 |
| 67 | $^1$H NMR (300 MHz, DMSO) δ 10.51 (s, 1H), 8.83 (d, J = 2.3, 1H), 8.62 (d, J = 9.3, 1H), 8.24 (dd, J = 2.7, 9.1, 1H), 7.96 (d, J = 8.9, 1H), 7.81 (d, J = 7.8, 1H), 7.67 (t, J = 7.6, 1H), 7.45 (d, J = 11.2, 2H), 3.86 (s, 3H), 2.62 (s, 3H)<br>MS (ESI) [M + H]$^+$ = 294 |
| 68 | $^1$H NMR (300 MHz, CDCl$_3$) δ 9.57 (s, 1H), 8.44 (d, J = 4.8, 1H), 8.05 (d, J = 8.8, 1H), 7.86 (s, 1H), 7.80 (d, J = 7.5, 1H), 7.64 (d, J = 8.0, 1H), 7.31 (t, J = 7.8, 1H), 7.19 (d, J = 4.3, 1H), 7.04 (d, J = 8.8, 1H) |
| 69 | $^1$H NMR (300 MHz, CDCl$_3$) δ 9.12 (s, 1H), 7.94 (d, J = 8.6, 1H), 7.71 (d, J = 7.5, 1H), 7.57 (d, J = 7.8, 1H), 7.40 (s, 1H), 7.25 (d, J = 10.2, 2H), 7.17 (s, 1H), 7.05 (s, 1H) |
| 70 | $^1$H NMR (300 MHz, CDCl$_3$) δ 9.07 (d, J = 8.5, 1H), 7.97 (d, J = 8.8, 1H), 7.90 (t, J = 8.0, 1H), 7.84 (s, 1H), 7.75 (dd, J = 1.1, 7.5, 1H), 7.62-7.55 (m, 1H), 7.31 (d, J = 7.6, 1H), 7.27 (t, J = 7.8, 1H), 7.08 (d, J = 8.8, 1H)<br>MS (ESI) [M + H]$^+$ = 274 |
| 71 | MS (ESI) [M + H]$^+$ = 274 |
| 72 | $^1$H NMR (300 MHz, CDCl$_3$) δ 8.67 (d, J = 7.9, 1H), 7.83 (d, J = 8.3, 1H), 7.71 (s, 1H), 7.69-7.61 (m, 1H), 7.57 (d, J = 7.9, 2H), 7.52 (d, J = 7.1, 1H), 7.28 (t, J = 7.4, 1H), 2.74 (q, J = 7.6, 2H), 2.42 (s, 3H), 1.31 (t, J = 7.6, 3H)<br>MS (ESI) [M + H]$^+$ = 264 |
| 73 | $^1$H NMR (300 MHz, CDCl$_3$) δ 8.91 (dd, J = 3.8, 9.0, 1H), 8.11 (d, J = 2.9, 1H), 7.81 (d, J = 8.3, 1H), 7.71 (s, 1H), 7.56 (dd, J = 7.4, 14.1, 2H), 7.51-7.42 (m, 1H), 7.29 (d, J = 7.2, 1H), 2.38 (s, 3H)<br>MS (ESI) [M + H]$^+$ = 254 |
| 74 | $^1$H NMR (300 MHz, CDCl$_3$) δ 8.96 (d, J = 8.3, 1H), 8.49 (s, 1H), 7.89 (dd, J = 1.9, 9.0, 1H), 7.82 (d, J = 8.2, 1H), 7.72 (s, 1H), 7.57 (t, J = 8.7, 3H), 7.33 (t, J = 7.4, 1H), 2.37 (s, 3H)<br>MS (ESI) [M + H]$^+$ = 304 |
| 75 | $^1$H NMR (300 MHz, CDCl$_3$) δ 7.83 (d, J = 9.0, 1H), 7.69 (dd, J = 1.3, 7.6, 1H), 7.53 (dd, J = 1.2, 8.0, 1H), 7.42 (d, J = 8.9, 2H), 7.15 (t, J = 7.8, 1H), 6.89 (d, J = 8.9, 2H), 6.79 (d, J = 8.9, 2H), 2.97 (s, 6H) |
| 77 | $^1$H NMR (300 MHz, CDCl$_3$) δ 7.83 (d, J = 8.8, 1H), 7.70 (d, J = 7.6, 1H), 7.59 (d, J = 8.6, 2H), 7.52 (d, J = 7.3, 1H), 7.16 (t, J = 7.7, 1H), 6.94 (d, J = 8.4, 3H), 6.86 (d, J = 8.8, 1H), 3.82 (s, 3H)<br>$^{13}$C NMR (75 MHz, CDCl$_3$) δ 156.40, 155.54, 144.29, 138.09, 132.96, 130.44, 129.99, 126.61, 125.22, 123.29, 122.66, 114.73, 112.16, 55.74.<br>MS (ESI) [M + H]$^+$ = 285 |
| 78 | $^1$H NMR (300 MHz, CDCl$_3$) δ 7.80 (t, J = 7.6, 2H), 7.64 (d, J = 8.9, 2H), 7.61-7.55 (m, 1H), 7.33 (t, J = 7.6, 1H), 7.19 (d, J = 8.7, 2H), 2.59 (s, 3H) |
| 79 | $^1$H NMR (300 MHz, CDCl$_3$) δ 7.78 (d, J = 8.4, 1H), 7.76-7.71 (m, 2H), 7.69 (s, 1H), 7.57 (dd, J = 1.1, 8.0, 1H), 7.51 (ddd, J = 1.5, 7.0, 8.4, 1H), 7.29-7.21 (m, 1H), 6.96-6.90 (m, 2H), 3.82 (s, 3H), 2.35 (s, 3H) |
| 80 | $^1$H NMR (300 MHz, CDCl$_3$) δ 7.92 (d, J = 8.9 Hz, 2H), 7.84 (d, J = 8.3 Hz, 1H), 7.78 (s, 1H), 7.62 (d, J = 8.0 Hz, 1H), 7.57 (t, J = 7.7 Hz, 1H), 7.32 (t, J = 7.4 Hz, 1H), 7.24 (d, J = 8.7 Hz, 2H), 6.53 (s, 1H), 2.42 (s, 3H)<br>$^{13}$C NMR (75 MHz, CDCl$_3$) δ 152.46, 146.25, 143.86, 139.33, 136.83, 128.93, 126.96, 126.71, 124.75, 123.56, 121.88, 120.44, 119.95, 17.77.<br>MS (ESI) [M + H]$^+$ = 319 |
| 81 | $^1$H NMR (300 MHz, CDCl$_3$) δ 7.75 (d, J = 8.3, 1H), 7.66 (d, J = 8.5, 3H), 7.55 (d, J = 7.8, 1H), 7.48 (t, J = 7.6, 1H), 7.20 (d, J = 7.2, 1H), 6.80 (d, J = 8.8, 2H), 6.32 (s, 1H), 2.93 (s, 7H), 2.35 (s, 3H) |

TABLE II-continued

| Ex | Characterizations |
|---|---|
| 82 | $^1$H NMR (300 MHz, CDCl$_3$) δ 7.92 (d, J = 8.9, 1H), 7.82-7.70 (m, 2H), 7.66 (d, J = 7.8, 1H), 7.59 (t, J = 7.6, 1H), 7.30 (dd, J = 6.0, 13.5, 1H), 7.14 (s, 1H), 7.11 (s, 1H), 6.84 (d, J = 8.9, 1H), 2.32 (s, 3H)<br>MS (ESI) [M + H]$^+$ = 319 |
| 83 | $^1$H NMR (300 MHz, CDCl$_3$) δ 7.93-7.86 (m, 1H), 7.85 (s, 1H), 7.82 (d, J = 8.4, 1H), 7.59 (dd, J = 8.2, 15.5, 2H), 7.44-7.38 (m, 1H), 7.29 (dd, J = 8.3, 16.8, 2H), 6.91 (d, J = 9.0, 1H), 6.87 (d, J = 8.3, 1H)<br>MS (ESI) [M + H]$^+$ = 305 |
| 84 | $^1$H NMR (300 MHz, CDCl$_3$) δ 8.67 (d, J = 8.1, 1H), 7.92 (d, J = 8.9, 1H), 7.85 (d, J = 8.4, 1H), 7.63 (d, J = 7.6, 1H), 7.58 (d, J = 7.3, 1H), 7.30 (dd, J = 6.8, 14.8, 3H), 7.02 (t, J = 7.8, 1H), 6.89 (d, J = 8.9, 1H)<br>MS (ESI) [M + H]$^+$ = 305 |
| 86 | $^1$H NMR (300 MHz, CDCl$_3$) δ 7.93 (d, J = 8.9, 1H), 7.83 (d, J = 8.3, 1H), 7.70 (d, J = 12.0, 1H), 7.61 (dd, J = 7.9, 18.1, 2H), 7.32 (d, J = 7.9, 1H), 7.31-7.25 (m, 1H), 7.21 (t, J = 6.5, 1H), 6.92 (d, J = 8.9, 1H), 6.79-6.68 (m, 1H)<br>MS (ESI) [M + H]$^+$ = 239 |
| 87 | $^1$H NMR (300 MHz, CDCl$_3$) δ 8.27 (s, 1H), 7.76 (d, J = 8.9, 1H), 7.67 (d, J = 7.5, 1H), 7.51 (d, J = 8.2, 1H), 7.45 (d, J = 7.9, 1H), 7.28 (d, J = 8.2, 1H), 7.14 (t, J = 7.8, 1H), 6.86 (d, J = 10.1, 1H), 6.76 (d, J = 8.9, 1H)<br>MS (ESI) [M + H]$^+$ = 339 |
| 88 | $^1$H NMR (300 MHz, CDCl$_3$) δ 8.11 (dt, J = 2.1, 12.1, 1H), 7.76 (d, J = 8.9, 1H), 7.66 (dd, J = 1.2, 7.6, 1H), 7.45 (dd, J = 1.1, 8.0, 1H), 7.22 (dd, J = 1.4, 7.2, 2H), 7.18 (d, J = 7.6, 1H), 7.12 (d, J = 7.8, 1H), 6.75 (d, J = 8.9, 1H), 6.69 (d, J = 7.9, 1H)<br>MS (ESI) [M + H]$^+$ = 273 |
| 89 | $^1$H NMR (300 MHz, DMSO) δ 11.38 (s, 1H), 8.41 (d, J = 9.1, 1H), 7.93 (d, J = 7.8, 1H), 7.80 (dt, J = 8.1, 20.9, 4H), 7.50 (d, J = 7.8, 3H), 7.36 (d, J = 9.3, 1H) |
| 90 | $^1$H NMR (300 MHz, CDCl$_3$) δ 7.84 (d, J = 9.1, 2H), 7.79 (d, J = 8.9, 1H), 7.67 (dd, J = 1.2, 7.6, 1H), 7.48 (dd, J = 1.1, 8.0, 1H), 7.18 (s, 3H), 6.89 (s, 1H), 6.75 (d, J = 8.9, 1H)<br>$^{13}$C NMR (75 MHz, CDCl$_3$) δ 153.88, 144.30, 143.91, 139.00, 138.25, 131.13, 130.13, 126.55, 125.42, 123.45, 122.50, 122.17, 120.49, 119.10, 113.24.<br>MS (ESI) [M + H]$^+$ = 339 |
| 91 | $^1$H NMR (300 MHz, CDCl$_3$) δ 8.74 (s, 1H), 8.54 (s, 1H), 8.46 (d, J = 8.8, 1H), 7.91 (dd, J = 5.5, 14.5, 2H), 7.79 (d, J = 8.9, 1H), 7.67 (d, J = 2.1, 1H), 7.56 (dd, J = 2.3, 8.9, 1H), 7.35 (d, J = 8.9, 1H) |
| 92 | $^1$H NMR (300 MHz, CDCl$_3$) δ 8.67 (d, J = 7.9, 1H), 7.83 (d, J = 8.3, 1H), 7.71 (s, 1H), 7.69-7.61 (m, 1H), 7.55 (dd, J = 7.5, 14.4, 2H), 7.29 (d, J = 7.8, 1H), 6.80 (d, J = 7.4, 1H) |
| 93 | $^1$H NMR (300 MHz, CDCl$_3$) δ 9.21 (dd, J = 1.5, 8.4, 1H), 7.85 (d, J = 8.4, 1H), 7.73 (s, 1H), 7.58 (d, J = 7.8, 1H), 7.53 (dd, J = 1.3, 8.3, 1H), 7.40-7.35 (m, 1H), 7.32 (dd, J = 1.1, 4.6, 1H), 7.31-7.24 (m, 2H), 7.04 (s, 1H), 7.02-6.94 (m, 1H), 2.38 (s, 3H) |
| 94 | $^1$H NMR (300 MHz, CDCl$_3$) δ 8.16 (d, J = 8.7, 1H), 7.83 (d, J = 8.9, 1H), 7.63 (d, J = 7.6, 1H), 7.48 (d, J = 8.0, 1H), 7.13 (t, J = 7.8, 1H), 7.08 (s, 1H), 7.04 (s, 2H), 6.81 (d, J = 8.9, 2H), 2.27 (s, 3H)<br>MS (ESI) [M + H]$^+$ = 353 |
| 95 | $^1$H NMR (300 MHz, MeOD) δ 8.42 (s, 1H), 7.94 (d, J = 7.9, 1H), 7.83 (d, J = 8.1, 1H), 7.78 (d, J = 7.1, 1H), 7.72 (d, J = 8.7, 2H), 7.58 (d, J = 8.2, 3H), 2.60 (s, 3H)<br>MS (ESI) [M + H]$^+$ = 319 |
| 96 | $^1$H NMR (300 MHz, CDCl$_3$) δ 7.79 (d, J = 8.9, 1H), 7.70 (d, J = 8.9, 1H), 7.64 (d, J = 8.9, 2H), 7.59 (d, J = 2.1, 1H), 7.50 (dd, J = 2.3, 8.9, 1H), 7.19 (d, J = 8.6, 2H), 6.85 (d, J = 8.9, 1H)<br>MS (ESI) [M + H]$^+$ = 281 |
| 97 | $^1$H NMR (300 MHz, MeOD) δ 8.11 (d, J = 8.4, 1H), 7.81 (s, 2H), 7.62 (d, J = 8.7, 3H), 7.51 (d, J = 8.3, 2H), 7.12 (s, 1H), 2.77 (s, 3H)<br>MS (ESI) [M + H]$^+$ = 319 |
| 98 | MS (ESI) [M + H]$^+$ = 383-385 |
| 99 | MS (ESI) [M + H]$^+$ = 320 |
| 100 | MS (ESI) [M + H]$^+$ = 316 |
| 101 | $^1$H NMR (300 MHz, CDCl$_3$) δ 7.82 (d, J = 8.9, 1H), 7.70-7.63 (m, 1H), 7.51 (dd, J = 5.3, 7.6, 3H), 7.14 (t, J = 7.8, 1H), 6.91 (d, J = 8.8, 3H), 6.85 (d, J = 9.0, 2H), 3.96 (t, J = 6.5, 2H), 1.84-1.68 (m, 3H), 1.49 (dd, J = 7.4, 15.0, 3H), 0.97 (t, J = 7.4, 3H)<br>MS (ESI) [M + H]$^+$ = 327 |
| 102 | $^1$H NMR (300 MHz, CDCl$_3$) δ 7.89 (d, J = 8.9, 1H), 7.76 (d, J = 8.5, 1H), 7.63 (d, J = 8.1, 1H), 7.59 (s, 1H), 7.54 (d, J = 8.8, 2H), 7.38-7.24 (m, 3H), 7.09 (d, J = 7.4, 1H), 7.02 (dd, J = 2.4, 8.8, 4H), 6.90 (d, J = 8.9, 1H)<br>MS (ESI) [M + H]$^+$ = 313 |
| 103 | MS (ESI) [M + H]$^+$ = 334 |
| 104 | $^1$H NMR (300 MHz, CDCl$_3$) δ 8.49 (d, J = 2.5, 1H), 7.89 (d, J = 8.8, 1H), 7.72 (d, J = 7.6, 1H), 7.63 (dd, J = 2.5, 8.9, 1H), 7.53 (d, J = 8.0, 1H), 7.23 (dd, J = 6.2, 14.0, 2H), 7.04 (s, 1H), 6.81 (d, J = 8.8, 1H)<br>MS (ESI) [M + H]$^+$ = 373 |

TABLE II-continued

| Ex | Characterizations |
|---|---|
| 105 | $^1$H NMR (300 MHz, CDCl$_3$) δ 8.85 (d, J = 2.6, 1H), 8.45 (d, J = 2.3, 1H), 8.01 (d, J = 8.1, 1H), 7.71 (d, J = 7.8, 1H), 7.58 (s, 1H), 7.53 (d, J = 7.6, 1H), 7.51-7.45 (m, 2H), 7.45-7.36 (m, 1H), 6.72-6.62 (m, 2H), 2.48 (s, 3H)<br>13C NMR (75 MHz, CDCl$_3$) δ 157.18, 154.80, 145.42, 143.80, 138.17, 135.04, 128.88, 128.76, 127.17, 127.04, 120.69, 115.22, 106.73, 24.38 |
| 106 | $^1$H NMR (300 MHz, DMSO) δ 10.24 (s, 1H), 9.06 (d, J = 2.3, 1H), 8.65 (d, J = 1.8, 1H), 8.60 (d, J = 8.3, 1H), 8.56 (d, J = 4.5, 1H), 7.97 (dd, J = 8.2, 14.4, 2H), 7.69 (t, J = 6.9, 1H), 7.59 (t, J = 7.4, 1H), 7.08 (dd, J = 4.6, 8.3, 1H)<br>MS (ESI) [M + H]$^+$ = 267 |
| 107 | $^1$H NMR (300 MHz, CDCl$_3$) δ 8.77 (dd, J = 1.5, 4.3, 1H), 8.06 (dd, J = 10.8, 18.4, 3H), 7.93 (d, J = 2.4, 1H), 7.57 (dd, J = 2.4, 9.0, 1H), 7.39 (ddd, J = 3.1, 8.3, 12.5, 3H), 6.93 (d, J = 8.4, 1H), 6.89 (s, 1H), 2.29 (s, 3H) |
| 108 | $^1$H NMR (300 MHz, CDCl$_3$) δ 8.72 (dd, J = 1.6, 4.2, 1H), 8.61 (d, J = 2.4, 1H), 8.11 (d, J = 8.3, 1H), 8.00 (d, J = 9.0, 1H), 7.91 (dd, J = 1.2, 5.0, 1H), 7.69 (dd, J = 2.4, 9.1, 1H), 7.35-7.26 (m, 2H), 7.01 (dd, J = 1.2, 7.9, 1H), 6.77 (dd, J = 5.1, 7.8, 1H), 3.93 (s, 3H) |
| 109 | $^1$H NMR (300 MHz, CDCl$_3$) δ 9.68 (s, 1H), 8.21 (s, 2H), 7.94 (d, J = 8.9, 1H), 7.79 (d, J = 9.2, 1H), 7.67 (d, J = 2.3, 1H), 7.56 (dd, J = 2.3, 8.9, 1H), 7.34 (d, J = 8.9, 1H)<br>MS (ESI) [M + H]$^+$ = 257 |
| 110 | 1H NMR (300 MHz, CDCl$_3$) δ 10.32 (s, 1H), 8.33-8.21 (m, 2H), 8.05 (d, J = 8.9, 1H), 8.00 (dd, J = 1.2, 7.6, 1H), 7.69 (dd, J = 1.1, 7.8, 1H), 7.61 (s, 1H), 7.30-7.22 (m, 3H), 7.16 (d, J = 8.8, 1H).<br>MS (ESI) [M + H]$^+$ = 301-303 |
| 111 | $^1$H NMR (300 MHz, CDCl$_3$) δ 7.82 (d, J = 8.9, 1H), 7.70-7.63 (m, 1H), 7.51 (dd, J = 5.3, 7.6, 3H), 7.14 (t, J = 7.8, 1H), 6.91 (d, J = 8.8, 3H), 6.85 (d, J = 9.0, 2H), 3.96 (t, J = 6.5, 2H), 1.84-1.68 (m, 3H), 1.49 (dd, J = 7.4, 15.0, 3H), 0.97 (t, J = 7.4, 3H) |
| 112 | $^1$H NMR (300 MHz, CDCl$_3$) δ 7.89 (d, J = 8.9, 1H), 7.76 (d, J = 8.5, 1H), 7.63 (d, J = 8.1, 1H), 7.59 (s, 1H), 7.54 (d, J = 8.8, 2H), 7.38-7.24 (m, 3H), 7.09 (d, J = 7.4, 1H), 7.02 (dd, J = 2.4, 8.8, 4H), 6.90 (d, J = 8.9, 1H)<br>$^{13}$C NMR (75 MHz, DMSO) δ 152.94, 150.19, 142.48, 142.18, 138.20, 137.55, 135.74, 129.71, 126.99, 125.35, 123.84, 114.75.<br>MS (ESI) [M + H]$^+$ = 255 |
| 113 | $^1$H NMR (300 MHz, CDCl$_3$) δ 9.74 (s, 1H), 8.20 (s, 2H), 8.03 (d, J = 8.6, 1H), 7.87 (d, J = 7.6, 1H), 7.80 (s, 1H), 7.70 (d, J = 8.0, 1H), 7.63 (t, J = 7.7, 1H), 7.37 (t, J = 7.4, 1H), 7.30 (d, J = 8.7, 1H) |
| 114 | $^1$H NMR (300 MHz, CDCl$_3$) δ 9.67 (s, 1H), 8.34-8.12 (m, 2H), 7.84 (d, J = 8.0, 2H), 7.70-7.54 (m, 1H), 7.38 (t, J = 7.6, 1H), 7.17 (s, 1H), 2.61 (s, 3H)<br>MS (ESI) [M + H]$^+$ = 237 |
| 115 | $^1$H NMR (300 MHz, CDCl$_3$) δ 10.15 (s, 1H), 8.24-8.12 (m, 2H), 7.79 (s, 1H), 7.71 (s, 1H), 7.55 (t, J = 8.3, 2H), 7.30 (d, J = 7.9, 1H), 2.38 (s, 3H)<br>MS (ESI) [M + H]$^+$ = 237 |
| 116 | MS (ESI) [M + H]$^+$ = 240 |
| 117 | MS (ESI) [M + H]$^+$ = 253 |
| 118 | MS (ESI) [M + H]$^+$ = 222 |
| 119 | MS (ESI) [M + H]$^+$ = 256 |
| 121 | MS (ESI) [M + H]$^+$ = 222 |
| 124 | $^1$H NMR (300 MHz, CDCl$_3$) δ 8.42 (s, 1H), 7.95 (dd, J = 1.3, 8.2, 1H), 7.87-7.78 (m, 3H), 7.70-7.61 (m, 1H), 7.55-7.47 (m, 1H), 7.26 (dd, J = 2.4, 6.5, 3H), 6.90 (s, 1H)<br>MS (ESI) [M + H]$^+$ = 306 |
| 125 | $^1$H NMR (300 MHz, CDCl$_3$) δ 8.42 (s, 1H), 8.03 (d, J = 9.5, 1H), 7.92 (d, J = 8.2, 1H), 7.73 (d, J = 8.2, 1H), 7.61 (t, J = 7.3, 1H), 7.46 (t, J = 7.2, 1H), 7.13 (s, 2H), 6.84 (s, 1H), 2.35 (s, 3H) |
| 126 | $^1$H NMR (300 MHz, CDCl$_3$) δ 8.40 (s, 1H), 8.03 (s, 1H), 7.94 (d, J = 8.2, 1H), 7.84 (d, J = 8.2, 1H), 7.65 (t, J = 7.4, 1H), 7.53 (d, J = 7.1, 1H), 7.48 (d, J = 7.2, 1H), 7.35 (t, J = 8.2, 1H), 7.22 (s, 1H), 6.94 (d, J = 8.1, 1H) |
| 127 | $^1$H NMR (300 MHz, CDCl$_3$) δ 8.85 (dd, J = 1.0, 8.3, 1H), 8.47 (s, 1H), 7.96 (d, J = 8.2, 1H), 7.85 (d, J = 8.3, 1H), 7.72-7.61 (m, 1H), 7.57-7.47 (m, 1H), 7.42-7.36 (m, 1H), 7.33 (d, J = 10.0, 1H), 7.14 (s, 1H), 7.13-7.04 (m, 1H) |
| 128 | $^1$H NMR (300 MHz, CDCl$_3$) δ 9.17 (s, 1H), 8.68 (d, J = 9.1, 1H), 8.64 (d, J = 4.8, 2H), 8.15 (d, J = 9.1, 1H), 7.87 (d, J = 8.4, 1H), 7.76 (d, J = 8.1, 1H), 7.64 (t, J = 7.7, 1H), 7.39 (t, J = 7.5, 1H), 6.87 (t, J = 4.8, 1H)<br>$^{13}$C NMR (75 MHz, CDCl3) δ 158.34, 138.07, 129.85, 127.63, 127.31, 124.34, 114.20, 113.90. |
| 129 | $^1$H NMR (300 MHz, CDCl$_3$) δ 9.14 (s, 1H), 8.73 (d, J = 21.2, 3H), 8.17 (s, 1H), 7.73 (d, J = 20.3, 2H), 7.28 (d, J = 9.6, 2H), 6.91 (s, 1H) |
| 130 | $^1$H NMR (300 MHz, CDCl$_3$) δ 9.05 (s, 1H), 8.64 (d, J = 4.8, 2H), 8.52 (s, 1H), 7.89 (dd, J = 8.5, 14.6, 2H), 7.63 (t, J = 7.5, 1H), 7.41 (t, J = 7.4, 1H), 6.86 (t, J = 4.8, 1H), 2.74 (s, 3H)<br>MS (ESI) [M + H]$^+$ = 237 |
| 132 | $^1$H NMR (300 MHz, CDCl$_3$) δ 8.86 (d, J = 2.6, 1H), 8.70 (d, J = 2.5, 1H), 8.32 (d, J = 1.1, 1H), 8.25-8.21 (m, 1H), 8.10 (d, J = 2.7, 1H), 8.06 (d, J = 8.3, 1H), 7.82 (dd, J = 1.2, 7.9, 1H), 7.66-7.51 (m, 3H), 6.89 (s, 1H) |

TABLE II-continued

| Ex | Characterizations |
|---|---|
| 135 | $^1$H NMR (300 MHz, CDCl$_3$) δ 9.09 (s, 1H), 8.71 (s, 1H), 8.54 (d, J = 8.4, 1H), 8.37 (dd, J = 1.0, 4.9, 1H), 7.96 (d, J = 8.2, 1H), 7.85 (d, J = 8.3, 1H), 7.82-7.74 (m, 1H), 7.66 (t, J = 7.6, 1H), 7.52 (dd, J = 7.0, 8.1, 1H), 7.02 (dd, J = 5.0, 7.2, 1H)<br>MS (ESI) [M + H]$^+$ = 223 |
| 136 | $^1$H NMR (300 MHz, CDCl$_3$) δ 9.02 (s, 1H), 8.70 (s, 1H), 8.30 (s, 1H), 8.20 (d, J = 5.1, 1H), 7.94 (d, J = 8.1, 1H), 7.84 (d, J = 8.2, 1H), 7.64 (t, J = 7.6, 1H), 7.49 (t, J = 8.1, 1H), 6.83 (d, J = 5.0, 1H), 2.43 (s, 3H).<br>$^{13}$C NMR (75 MHz, CDCl$_3$) δ 153.28, 150.20, 148.55, 147.40, 140.93, 139.83, 138.35, 130.44, 129.16, 127.18, 126.28, 119.70, 113.75, 21.87.<br>MS (ESI) [M + H]$^+$ = 237 |
| 137 | $^1$H NMR (300 MHz, DMSO) δ 11.10 (s, 1H), 9.03 (s, 1H), 8.82-8.75 (m, 1H), 8.56 (d, J = 8.9, 1H), 8.24 (dd, J = 2.3, 8.9, 1H), 7.96 (dd, J = 1.2, 8.2, 1H), 7.87 (dd, J = 1.0, 8.3, 1H), 7.79-7.71 (m, 1H), 7.61 (ddd, J = 1.4, 7.0, 8.3, 1H)<br>MS (ESI) [M + H]$^+$ = 248 |
| 138 | $^1$H NMR (300 MHz, CDCl$_3$) δ 8.72 (s, 1H), 8.53 (s, 1H), 8.20 (d, J = 8.3, 1H), 7.93 (d, J = 8.2, 1H), 7.81 (d, J = 8.3, 1H), 7.62 (td, J = 3.4, 8.1, 2H), 7.53-7.43 (m, 1H), 6.83 (d, J = 7.4, 1H), 2.48 (s, 3H)<br>$^{13}$C NMR (75 MHz, CDCl$_3$) δ 156.86, 152.27, 148.40, 140.92, 139.70, 139.00, 138.35, 130.42, 129.13, 127.14, 126.27, 117.76, 110.01, 24.15.<br>MS (ESI) [M + H]$^+$ = 237 |
| 139 | $^1$H NMR (300 MHz, CDCl$_3$) δ 8.53 (s, 1H), 8.20 (d, J = 4.8, 1H), 8.04 (d, J = 8.3, 1H), 7.92 (d, J = 8.4, 1H), 7.87 (s, 1H), 7.79 (t, J = 7.6, 1H), 7.60 (t, J = 7.6, 1H), 6.88 (d, J = 4.7, 1H), 2.46 (s, 3H) |
| 140 | $^1$H NMR (300 MHz, CDCl$_3$) δ 9.93 (s, 1H), 8.19 (s, 1H), 8.05 (d, J = 8.1, 1H), 7.99 (s, 1H), 7.82 (d, J = 8.2, 1H), 7.69 (t, J = 7.6, 1H), 7.59 (t, J = 8.2, 1H), 2.53 (s, 4H) |
| 141 | $^1$H NMR (300 MHz, CDCl$_3$) δ 9.72 (s, 1H), 9.35 (s, 1H), 8.30 (d, J = 5.0, 1H), 8.05 (d, J = 7.7, 1H), 7.87 (d, J = 7.0, 1H), 7.66 (dd, J = 7.4, 16.9, 3H), 6.92 (d, J = 4.9, 1H), 2.58 (s, 3H) |
| 143 | $^1$H NMR (300 MHz, DMSO) δ 8.85 (s, 1H), 8.42 (d, J = 5.3, 1H), 7.96 (d, J = 9.1, 1H), 7.44 (s, 1H), 7.30 (s, 4H), 7.28-7.21 (m, 2H), 6.66 (d, J = 5.3, 1H), 2.99 (s, 6H)<br>$^{13}$C NMR (75 MHz, DMSO) δ 156.82, 150.25, 149.69, 143.79, 141.71, 125.95, 122.33, 118.88, 117.37, 115.95, 109.39, 104.92, 43.57<br>MS (ESI) [M + H]+ = 348 |
| 144 | MS (ESI) [M + H]$^+$ = 390 |
| 145 | MS (ESI) [M + H]$^+$ = 252 |
| 146 | $^1$H NMR (300 MHz, DMSO) δ 9.34 (s, 1H), 8.59 (d, J = 5.2, 1H), 8.53 (s, 1H), 8.13 (d, J = 5.1, 1H), 7.98 (d, J = 9.0, 1H), 7.66 (d, J = 9.1, 1H), 6.80 (d, J = 5.2, 1H), 6.76 (s, 1H), 6.69 (d, J = 4.9, 1H), 4.00 (s, 3H), 2.26 (s, 3H)<br>$^{13}$C NMR (75 MHz, DMSO) δ 161.31, 155.67, 151.63, 150.25, 147.77, 147.01, 142.97, 121.56, 119.16, 116.61, 114.75, 112.60, 111.41, 98.91, 55.78, 20.66.<br>MS (ESI) [M + H]$^+$ = 266 |
| 147 | MS (ESI) [M + H]$^+$ = 279 |
| 149 | MS (ESI) [M + H]$^+$ = 318 |
| 150 | MS (ESI) [M + H]$^+$ = 280 |
| 151 | $^1$H NMR (300 MHz, CDCl$_3$) δ 8.35 (s, 1H), 8.04 (d, J = 8.3, 1H), 7.82 (d, J = 8.9, 1H), 7.74 (d, J = 8.9, 1H), 7.60 (t, J = 7.8, 2H), 7.50 (dd, J = 2.3, 8.9, 1H), 7.36 (d, J = 8.9, 1H), 6.79 (d, J = 7.4, 1H), 2.75 (q, J = 7.6, 2H), 1.30 (t, J = 7.6, 3H).<br>MS (ESI) [M + H]$^+$ = 284 |
| 152 | $^1$H NMR (300 MHz, CDCl$_3$) δ 8.30 (d, J = 8.5, 1H), 8.08 (s, 1H), 7.90 (d, J = 9.0, 1H), 7.77 (d, J = 8.9, 1H), 7.65 (d, J = 2.2, 1H), 7.55 (td, J = 2.0, 8.8, 2H), 7.39 (d, J = 9.0, 1H), 2.31 (s, 3H).<br>MS (ESI) [M + H]$^+$ = 270 |
| 153 | $^1$H NMR (300 MHz, CDCl$_3$) δ 8.75 (s, 1H), 8.54 (s, 1H), 8.46 (d, J = 8.8, 1H), 7.91 (dd, J = 5.5, 14.5, 2H), 7.79 (d, J = 8.9, 1H), 7.67 (d, J = 2.1, 1H), 7.56 (dd, J = 2.3, 8.9, 1H), 7.35 (d, J = 8.9, 1H).<br>MS (ESI) [M + H]$^+$ = 324 |
| 154 | $^1$H NMR (300 MHz, DMSO) δ 9.08 (s, 1H), 8.12 (d, J = 8.4, 1H), 7.73 (d, J = 8.2, 2H), 7.66 (d, J = 10.0, 1H), 7.53 (s, 1H), 7.25 (s, 1H), 6.82 (s, 1H), 5.10 (s, 2H), 2.16 (s, 4H).<br>MS (ESI) [M + H]$^+$ = 285 |
| 155 | $^1$H NMR (300 MHz, CDCl$_3$) δ 7.68 (d, J = 8.3, 1H), 7.61 (s, 1H), 7.56 (d, J = 11.5, 2H), 7.44 (d, J = 8.3, 1H), 7.38 (d, J = 7.8, 1H), 7.13 (t, J = 7.4, 1H), 6.80 (d, J = 8.7, 2H), 3.85 (t, J = 6.5, 2H), 2.18 (s, 3H), 1.73-1.58 (m, 2H), 1.48-1.31 (m, 2H), 0.88 (t, J = 7.3, 3H)<br>MS (ESI) [M + H]$^+$ = 307 |
| 156 | $^1$H NMR (300 MHz, CDCl$_3$) δ 7.75 (d, J = 9.1, 1H), 7.62 (d, J = 8.9, 1H), 7.58 (d, J = 2.2, 1H), 7.48 (dd, J = 2.4, 8.9, 1H), 7.30 (d, J = 8.9, 2H), 6.86 (d, J = 9.0, 1H), 6.77 (d, J = 8.9, 2H), 6.71 (s, 1H), 2.97 (s, 6H)<br>MS (ESI) [M + H]$^+$ = 298 |
| 157 | $^1$H NMR (300 MHz, CDCl$_3$) δ 7.98 (d, J = 2.6, 1H), 7.89 (d, J = 8.9, 1H), 7.72 (d, J = 7.5, 1H), 7.62 (dd, J = 2.6, 8.8, 1H), 7.55 (d, J = 7.8, 1H), 7.20 (t, J = 7.8, 1H), 6.95 (d, J = 8.9, 1H), 6.84 (d, J = 8.9, 1H), 6.79 (s, 1H), 3.91 (s, 3H)<br>MS (ESI) [M + H]$^+$ = 319 |

TABLE II-continued

| Ex | Characterizations |
|---|---|
| 158 | $^1$H NMR (300 MHz, CDCl$_3$) δ 7.89 (d, J = 9.0, 1H), 7.70 (dd, J = 1.2, 7.5, 1H), 7.56 (dd, J = 1.1, 8.0, 1H), 7.30 (d, J = 8.6, 1H), 7.20 (t, J = 7.8, 1H), 6.71 (t, J = 5.9, 2H), 6.64 (d, J = 9.5, 1H).<br>MS (ESI) [M + H]$^+$ = 354 |
| 159 | $^1$H NMR (300 MHz, CDCl$_3$) δ 8.80 (d, J = 2.6, 1H), 8.37 (d, J = 2.6, 1H), 8.01 (d, J = 8.1, 1H), 7.91 (dd, J = 1.6, 4.9, 1H), 7.78-7.70 (m, 1H), 7.58-7.43 (m, 2H), 7.09 (dd, J = 1.6, 7.6, 1H), 6.84 (dd, J = 4.9, 7.6, 1H), 6.69 (s, 1H), 3.82-3.07 (m, 2H). |
| 160 | $^1$H NMR (300 MHz, CDCl$_3$) δ 9.68-8.90 (m, 1H), 8.77 (s, 1H), 8.35 (s, 1H), 8.14 (d, J = 5.0, 1H), 7.96 (s, 1H), 7.79 (d, J = 8.8, 1H), 7.61 (d, J = 8.5, 1H), 6.88 (d, J = 4.8, 1H), 2.46 (s, 3H) |
| 161 | $^1$H NMR (300 MHz, CDCl$_3$) δ 9.98 (s, 1H), 8.70 (s, 1H), 8.45 (s, 1H), 8.27 (d, J = 5.2, 1H), 7.94 (d, J = 8.1, 1H), 7.84 (d, J = 8.2, 1H), 7.63 (t, J = 7.5, 1H), 7.48 (t, J = 7.5, 1H), 6.87 (d, J = 5.0, 1H), 2.74 (q, J = 7.6, 2H), 1.34 (t, J = 7.6, 3H).<br>MS (ESI) [M + H]$^+$ = 251 |
| 162 | $^1$H NMR (300 MHz, CDCl$_3$) δ 8.73 (s, 1H), 8.70-8.60 (m, 1H), 8.48 (s, 1H), 8.31 (s, 1H), 7.98 (d, J = 8.1, 1H), 7.86 (d, J = 7.9, 1H), 7.68 (t, J = 8.2, 1H), 7.54 (t, J = 8.1, 1H), 2.49 (s, 3H)<br>MS (ESI) [M + H]$^+$ = 315 |
| 163 | $^1$H NMR (300 MHz, CDCl$_3$) δ 8.75 (s, 1H), 8.68 (s, 1H), 8.01 (s, 1H), 7.95 (d, J = 8.2, 1H), 7.84 (d, J = 8.3, 1H), 7.64 (t, J = 8.2, 1H), 7.49 (t, J = 7.0, 1H), 6.69 (s, 1H), 2.45 (s, 3H), 2.38 (s, 3H)<br>MS (ESI) [M + H]$^+$ = 251 |
| 164 | $^1$H NMR (300 MHz, DMSO) δ 10.46 (s, 1H), 9.00 (s, 1H), 8.41 (s, 1H), 8.24 (d, J = 3.0, 1H), 7.90 (d, J = 8.2, 1H), 7.79 (d, J = 8.3, 1H), 7.69 (t, J = 7.0, 1H), 7.52 (t, J = 7.4, 1H), 6.98 (d, J = 4.8, 1H), 5.45 (q, J = 5.6, 1H), 4.58 (d, J = 5.7, 2H).<br>MS (ESI) [M + H]$^+$ = 253 |
| 165 | $^1$H NMR (300 MHz, CDCl$_3$) δ 9.07 (s, 1H), 8.79 (s, 1H), 8.51 (s, 1H), 8.18 (s, 1H), 8.09-8.01 (m, 1H), 7.94 (d, J = 8.4, 1H), 7.81-7.71 (m, 1H), 7.69-7.59 (m, 1H), 2.80 (s, 3H)<br>MS (ESI) [M + H]$^+$ = 282 |
| 166 | $^1$H NMR (300 MHz, CDCl$_3$) δ 8.49 (d, J = 5.0, 1H), 7.77 (d, J = 9.0, 1H), 7.32 (d, J = 2.0, 1H), 7.12 (d, J = 9.0, 2H), 6.99 (dd, J = 2.0, J = 9.0, 1H), 6.82 (d, J = 9.0, 2H), 6.57 (d, J = 5.0, 1H), 5.78 (s, 1H), 3.74 (s, 3H), 3.17 (s, 4H), 2.62 (s, 4H), 2.34 (s, 3H) |
| 167 | MS (ESI) [M + H]$^+$ = 335 |
| 168 | MS (ESI) [M + H]$^+$ = 321 |

The following examples illustrate in detail the preparation of compounds (51), (64), (110), (143) and (148) as described above. The structures of the products obtained have been confirmed at least by NMR spectra.

EXAMPLES

According to route (A), the compound of formula (III) is placed in a protic solvent such as tert-butanol. The compound of formula (IV) is then added in a 1.1 molar ratio with respect to the compound of formula (III) in presence of an inorganic base, such as Cs$_2$CO$_3$ or K$_2$CO$_3$, in a 2.8 molar ratio, in the presence of a diphosphine, such as Xantphos (4,5-Bis(diphenylphosphino)-9,9-dimethylxanthene), or X-Phos 2-Dicyclohexylphosphino-2',4',6'-triisopropylbiphenyl in a 2 mol % amount relative to the total amount of compound of formula (III), and in the presence of a catalyst, such as Pd(OAc)$_2$ or Pd$_2$dba$_3$ in a 2 mol % amount relative to the total amount of compound of formula (III). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compounds (51), (64), (110), and (143).

According to route (B), the compound of formula (V) is placed in a protic solvent such as tert-butanol. The compound of formula (VI) is then added in a 1.1 molar ratio with respect to the compound of formula (V) in presence of Cs$_2$CO$_3$ in a 2.8 molar ratio, in the presence of Xantphos (4,5-Bis(diphenylphosphino)-9,9-dimethylxanthene) in a 2 mol % amount relative to the total amount of compound of formula (V), and in the presence of a Pd(OAc)$_2$, in a 2 mol % amount relative to the total amount of compound of formula (V). The reaction mixture is then heated at 90° C., and stirred during 20 hours, under argon. The reaction mixture is concentrated under reduced pressure and the resulting residue is diluted with ethyl acetate. The organic phase is then washed twice with water, dried on magnesium sulphate, filtered and concentrated under reduced pressure. The residue could then be purified by column chromatography on silica gel to yield pure compound (148).

Example 1

Compound (51) of Table I

According to route (A), a mixture of 2,8-dichloroquinoline (98.5 mg) and 2-amino-4,6-dimethylpyridine (67.1 mg), Pd(OAc)$_2$ (2.2 mg), XantPhos (5.8 mg) and Cs$_2$CO$_3$ (456 mg) in 2 mL of t-BuOH gave compound (51) (99.7 mg).

Example 2

Compound (64) of Table I

According to route (A), a mixture of 2-chloro-5-nitroquinoline (100.0 mg) and 2-amino-4-methylpyridine (57.6 mg), Pd$_2$dba$_3$ (20 mg), XantPhos (30 mg) and K$_2$CO$_3$ (270 mg) in 3 mL of t-BuOH gave compound (64) (14.0 mg).

The preparation of 2-chloro-5-nitroquinoline is described in Patent application WO2009/23844.

Example 3

Compound (110) of Table I

According to route (A), a mixture of 8-bromo-2-chloroquinoline (500 mg) and aminopyrazine (216 mg), $Pd_2dba_3$ (95 mg), XantPhos (120 mg) and $K_2CO_3$ (1.15 g) in 12 mL of t-BuOH gave compound (110) (245 mg).

The preparation of 8-bromo-2-chloroquinoline is described in Cottet, F. et al. Eur. J. Org. Chem. 2003, 8, 1559.

Example 4

Compound (143) of Table I

According to route (A), a mixture of 7-chloro-4-(N,N-dimethylamino)quinoline (500 mg), 4-trifluoromethoxyaniline (0.257 mL), $Pd_2dba_3$ (110 mg), XPhos (115 mg) and $K_2CO_3$ (1 g) in 10 mL of t-BuOH gave compound (143) (410 mg).

The preparation of 7-chloro-4-(N,N-dimethylamino)quinoline is described in Sanchez-Martin, R. et al. J. Med. Chem. 2005, 48, 3354.

Example 5

Compound (148) of Table I

According to route (B), a mixture of 5,8-dimethylisoquinolin-6-amine (59 mg) and 2-bromo-5-methylpyridine (86 mg), $Pd(OAc)_2$ (2.2 mg), XantPhos (5.8 mg) and $Cs_2CO_3$ (456 mg) in 2 mL of t-BuOH gave compound (148) (48 mg).

The preparation of 5,8-dimethylisoquinolin-6-amine is described in Australian Journal of Chemistry 1969, 22, 2489.

1H NMR (300 MHz, $CDCl_3$) δ 9.32 (s, 1H), 8.52 (d, J=6.0, 1H), 8.07 (s, 1H), 7.72 (d, J=6.0, 1H), 7.51 (s, 1H), 7.36 (dd, J=2.1, 8.4, 1H), 6.69 (d, J=8.3, 2H), 2.72 (s, 3H), 2.48 (s, 3H), 2.26 (s, 3H)

MS (ESI) [M+H]+=264

Example 6

Pharmacological Data

Standard Operating Procedure:

Effect of drug compounds on invasion of MDA-MB231-D3H2LN cells into collagen

Background:

A key step in the generation of tumor metastasis is tumor cell invasion of the extracellular matrix, a major component of which is collagen. Therefore, the invasion of tumor cells into collagen in vitro may be indicative of tumor metastasis in vivo. E. g., MDA-MB231-luc-D3H2LN mouse breast cancer cells display both higher invasion into collagen in vitro and a higher metastatic potential in vivo as compared to MDA-MB231 cells (from which they were derived). Using these MDA-MB231-luc-D3H2LN cells as a model, the aim of the experiment described here is to identify drug compounds that inhibit the invasion of tumor cells into collagen in vitro, therefore potentially inhibiting also the generation of tumor metastasis in vivo.

Assay Principle:

Step 1: Preparation of cells at the bottom of a collagen gel: Cells were suspended in a liquid collagen solution (4° C.), distributed into BSA-coated wells, and then collected at the bottom of the wells by centrifugation. The collagen was then solidified by incubation at 37° C. The BSA coating improves the adhesion of the collagen gel.

Step 2: Pre-treatment with the compounds to be tested: Concentrated drug solutions were then added on top of the collagen, and cells are pre-incubated for 24 h with the drugs at low serum conditions (0.025% FBS).

Step 3: Stimulation of invasion: Medium with 5% FBS was then added in order to stimulate invasion of the cells into the collagen gel.

Step 4: Fixation and staining: Following another 24 h incubation, cells were fixed and nuclei were stained.

Step 5: Analysis: Finally, plates were analyzed using an automated microscope. Fluorescent beads that have been included into the BSA coating serve to detect the bottom of the wells. Pictures of the stained nuclei were taken at the same level (0 μm) as well as 25 μm and 50 μm above.

Note:

In order to detect possible toxic effects, all compounds were tested in parallel in a viability assay. The viability assay was performed in parallel on serum-starved cells (as in the invasion assay) vs. cells under normal culture conditions (10% FBS).

Materials:

General Equipment:

Freezer (−20° C.), refrigerator (4° C.), ice machine, water bath (37° C.), incubator (37° C./5% $CO_2$), cell culture hood, vortex, vacuum pump, microscope, Malassez cell, Pipet aid, micropipettes (for pipetting 1-1000 μl), multichannel pipettes (for pipetting 20-200 μl), standard cell culture centrifuge, refrigerated centrifuge for 96 well plates.

General Consumables:

Sterile 96 well cell culture plates (for the viability assay), sterile tubes (1.5/15/50 ml), sterile pipettes (5/10/25 ml), sterile micropipette tips (for pipetting 1-1000 μl), sterile Pasteur pipettes, sterile reagent reservoirs.

General Products:

Sterile PBS, sterile Milli-Q water, DMSO, decomplemented FBS (frozen aliquots), 0.1 N NaOH, 1 M Hepes, MEM without serum (not older than 1 month), 2.5×MEM without serum (not older than 1 month), MEM with 10% FBS (not older than one month), 0.25% trypsin/1 mM EDTA solution, 37% formaldehyde solution.

Specific Equipment:

plate reader: Tecan Infinite F200 automated microscope: Cellomics ArrayScan VTI HCS Reader

Specific Consumables:

sterile black 96 well plates (for the invasion assay): Perkin Elmer ViewPlate-96 F TC, ref. 6005225 sterile 96 deep well polypropylene plates (for drug preparation): Starlab, ref. S1896-5110

Specific Products:

rat tail collagen, type 1: BD Biosciences, ref. 354236 (note: each new lot has to be validated)

red fluorescent beads (1 μm diameter): Invitrogen, ref. F13083

Y-27632 (5 mM aqueous solution): Calbiochem, ref. 688001 (in solution) or 688000 (dry powder)

BSA without fatty acids (sterile-filtered 4% aqueous solution): Sigma, ref. A8806 (dry powder)

Hoechst 33342 nuclear stain (10 mg/ml): Invitrogen, ref. H3570

MTS reagent: Promega CellTiter CellTiter 96® AQueous One Solution Reagent, ref. G3581 drug compounds to be tested: generally 25 or 50 mM in 100% DMSO (aliquots stored at −20° C., then at 4° C. for max. 3 months)

MDA-MB23'-luc-D3H2LN cells:

Limits for the cell cultures to be used in the assays:

total passage number: max. 30 last passage: between 2 and 4 days before, between 1:3 and 1:20 cell density: between 50 and 90% (optimally 70%) (between 1 and 2×106 cells per 100 mm dish)

Experimental Procedures:

General Considerations:

Controls and plate maps: Invasion assay: Negative control: No drug (just DMSO at equivalent concentration). Positive control: 10 µM Y-27632. To avoid edge effects, only the 60 central wells B2-G11 were used; lines A and H as well as columns 1 and 12 remain free. Each drug was tested at least in triplicate. The positive and negative controls were tested in double triplicates at different positions on each plate. Typical plate map (−=negative control, +=positive control, 1-16=16 different drug compounds):

|   | 1 | 2 | 3 | 4 | 5 | 6 | 7 | 8 | 9 | 10 | 11 | 12 |
|---|---|---|---|---|---|---|---|---|---|----|----|----|
| A |   |   |   |   |   |   |   |   |   |    |    |    |
| B |   | − | 1 | 2 | 3 | 4 | 5 | 6 | 7 | 8  | +  |    |
| C |   | − | 1 | 2 | 3 | 4 | 5 | 6 | 7 | 8  | +  |    |
| D |   | − | 1 | 2 | 3 | 4 | 5 | 6 | 7 | 8  | +  |    |
| E |   | + | 9 | 10| 11| 12| 13| 14| 15| 16 | −  |    |
| F |   | + | 9 | 10| 11| 12| 13| 14| 15| 16 | −  |    |
| G |   | + | 9 | 10| 11| 12| 13| 14| 15| 16 | −  |    |
| H |   |   |   |   |   |   |   |   |   |    |    |    |

Viability Assays:

No additional controls. The MTS viability assay was based on colorimetric detection of a product generated by the mitochondrial activity of the cells. Each drug was tested at least in duplicate. To detect potential direct interactions with the assay substrate, each drug was also tested in absence of cells (background signals). Typical plate map (controls and drug compounds as in the invasion assay, lines A-B and E-F: with cells, lines C-D and G-H: without cells; each 1 plate with 10% vs. 0.025% FBS):

|   | 1 | 2 | 3 | 4 | 5 | 6 | 7 | 8 | 9 | 10 | 11 | 12 |
|---|---|---|---|---|---|---|---|---|---|----|----|----|
| A |   | − | 1 | 2 | 3 | 4 | 5 | 6 | 7 | 8  | +  |    |
| B |   | − | 1 | 2 | 3 | 4 | 5 | 6 | 7 | 8  | +  |    |
| C |   | − | 1 | 2 | 3 | 4 | 5 | 6 | 7 | 8  | +  |    |
| D |   | − | 1 | 2 | 3 | 4 | 5 | 6 | 7 | 8  | +  |    |
| E |   | + | 9 | 10| 11| 12| 13| 14| 15| 16 | −  |    |
| F |   | + | 9 | 10| 11| 12| 13| 14| 15| 16 | −  |    |
| G |   | + | 9 | 10| 11| 12| 13| 14| 15| 16 | −  |    |
| H |   | + | 9 | 10| 11| 12| 13| 44| 15| 16 | −  |    |

The volumes or other quantities indicated in the following are required for testing 16 drug compounds per 96 wells-plate at 5 µM each (+controls) in an invasion assay and each one viability assay on serum-starved cells vs. cells under normal culture conditions according to the plate maps above. According to the number of tested compounds, the volumes and other quantities should be adapted for testing more or less compounds or different concentrations.

Day 1: Preparation and Treatment of the Cells (all Steps are Performed Under a Cell Culture Hood):

Preparation of 100× concentrated drug solutions in 10% DMSO:

prepare 10% DMSO in sterile PBS: 1.8 ml sterile PBS+0.2 ml DMSO prepare 100 µl/well 10% DMSO in PBS in 16 wells of a sterile 96 well polypropylene plate add each 1 or 2 µl of the 50 or 25 mM compound stock solutions, respectively mix by pipetting up and down Preparation of 4× concentrated drug and control solutions in 0.4% DMSO in MEM+0.1% FBS:

Prepare MEM+0.1% FBS: 12 ml MEM without serum+12 µl FBS (freshly thawed aliquot)

prepare 480 µl/well MEM+0.1% FBS in 20 wells of a sterile 96 deep well polypropylene plate negative controls (no drug): add each 20 µl 10% DMSO in sterile PBS positive controls (Y-27632): add each 14 µl sterile PBS+2 µl DMSO+4 µl 5 mM Y-27632 (freshly thawed aliquot)

drug compounds: add each 20 µl of the 100× concentrated drug solutions in 10% DMSO mix by pipetting up and down store at RT until use Coating of the Plates for the Invasion Assay:

mix 9.5 ml MEM without serum+0.5 ml 4% BSA without fatty acids+1 µl vortexed fluorescent beads (i.e. dilute 1:10000), vortex, distribute 100 µl/well into the plate for the invasion assay centrifuge 30' with 1800×g at 4° C. (e.g. 3000 rpm in a Jouan GR412 centrifuge)

remove supernatants by aspiration

Preparation of a 10×106 cells/ml Cell Suspension (During the Centrifugation of the Plates):

remove medium, wash cells with ~10 ml/dish PBS, add 1 ml/dish 0.25% trypsin/1 mM EDTA incubate 30-60 s at 37° C.

add 5-10 ml/dish pre-warmed MEM+10% FBS homogenize by pipetting up and down using a 10 ml pipette, pool all count cells using a Malassez cell centrifuge 2×106 (or more) cells for 5' with 150×g at RT (850 rpm in a std. cell culture centrifuge)

remove supernatant, resuspend cell pellet in 0.2 ml (or more, respectively) MEM without serum, yielding 10×106 cells/ml Preparation of the Invasion Assay (on Ice; Start During the Centrifugation of the Cells):

mix on ice in a pre-chilled tube: example for a 3.4 mg/ml collagen stock solution; volumes of collagen and water to be adapted according to the stock concentration of each collagen lot:

2.8 ml 2.5×MEM

441 µl water

140 µl M Hepes

49 µl 1 N NaOH 3.5 ml 3.4 mg/ml collagen stock solution (yielding 1.7 mg/ml collagen in 7 ml)

homogenize by pipetting gently up and down (keep on ice)

add 70 µl of the 10×106 cells/ml cell suspension, homogenize by pipetting gently up and down (yields 0.1×106 cells/ml in 1.7 mg/ml collagen in 7 ml 1×MEM+20 µM Hepes) (keep on ice)

distribute 100 µl/well (i.e. 10000 cells/well) into the coated wells of the plate for the invasion assay (all on ice)

centrifuge 5' with 200×g at 4° C. (e.g. 1000 rpm in a Jouan GR412 centrifuge)

add 200 µl/well PBS to all free wells incubate 30' at 37° C./5% $CO_2$ (solidification of the collagen)

Preparation of the Viability Assay on Serum-Starved Cells:

add 50 µl of the 10×106 cells/ml cell suspension to 5 ml MEM without serum (yields 0.1×106 cells/ml)

distribute 100 μl/well of this suspension (i.e. 10000 cells/well) or MEM without serum without cells, respectively, into a standard 96 well tissue culture plate, according to the plate map above add 200 μl/well PBS to all free wells incubate 30' at 37° C./5% $CO_2$ Preparation of the Viability Assay on Cells Under Normal Culture Conditions:

add 30 μl of the 10×106 cells/ml cell suspension to 5 ml MEM+10% FBS (yields 0.06×106 cells/ml)

distribute 100 μl/well of this suspension (i.e. 6000 cells/well) or MEM+10% FBS without cells, respectively, into a standard 96 well tissue culture plate, according to the plate map above add 200 μl/well PBS to all free wells incubate 30' at 37° C./5% $CO_2$ Treatment with the Drugs:

add each 33 μl/well of the 4× concentrated drug solutions in MEM+0.1% FBS to the corresponding wells in all three plates, according to the plate maps above incubate 24 h at 37° C./5% $CO_2$ Day 2: Addition of FBS to Stimulate the Invasion:

Microscopic Observation after 24 h of Treatment:

examine the cells of the viability assays

Addition of FBS (Under a Cell Culture Hood):

prepare MEM+5% FBS: 7.2 ml MEM without serum+0.8 ml FBS (freshly thawed aliquot or rest of the aliquot thawed the day before if kept at 4° C.)

add 33 μl/well to all wells of invasion and viability assays incubate 24 h at 37° C./5% $CO_2$ Day 3: Stop:

Microscopic Observation after 48 h of Treatment:

examine the cells of the viability assays

Viability Assays: MTS Assay:

add each 33 μl/well of the MTS reagent, incubate 2.5 h at 37° C. 15% $CO_2$ shake and read absorbance at 490 nm (proportional to the viability)

calculate the background-corrected signals by subtracting the means of the background signals in absence of cells from the corresponding signals in presence of cells normalize the background-corrected signals with respect to the mean signal of the negative controls (no drug) (viabilities are thus expressed in "% of control")

Invasion Assays:

fixation and staining (formaldehyde must be manipulated under a fume cupboard):

freshly prepare 1 μg/ml Hoechst 33342 in 18.5% formaldehyde: 5 ml PBS (not necessarily sterile)+5 ml 37% formaldehyde+1 μl 10 mg/ml Hoechst 33342 (note: for one plate, a smaller volume would be sufficient, but the minimal pipetted volume should not be below 1 μl)

add 50 μl/well to all wells of the invasion assay (yields 4.3% formaldehyde final)

seal with black film (provided with the plates)

incubate at least 7 h at RT

Day 3: 17 (Min 7 h/Max. 2 Weeks after Fixation and Staining): Analysis of the Invasion Assay:

Lecture using the Cellomics ArrayScan VTI HCS Reader:

BioApplication: SpotDetector.V3

Plate type: Perkin Elmer 96 well

Parameters of the Assay Protocol:

objective: 10×(NA 0.45)

apotome: yes (resulting optical slice: 11.7 μM)

fields per well: 8 autofocus in each field autofocus channel: 1 channel 1 (autofocus on, and photo of the fluorescent beads at the bottom of the wells): filter: XF93—TRITC; exposure time: usually between 0.002 and 0.01 s channel 2 (photo of the stained cells at the same level as the fluorescent beads): filter: XF100—Hoechst; exposure time: usually between 0.02 and 0.1 s; z offset: 0 μM channel 3 (photo of the stained cells 25 μM above the fluorescent beads): filter: XF100—Hoechst; exposure time: usually between 0.02 and 0.1 s; z offset: −25 μM channel 4 (photo of the fluorescent cells 50 μM above the fluorescent beads): filter: XF100—Hoechst; exposure time: usually between 0.02 and 0.1 s; z offset: −50 μM object identification: method: fixed threshold: 100-32767

| object selection parameters: | min. | max. |
| --- | --- | --- |
| SpotArea: | 20 | 1000000000000 |
| SpotShapeBFR: | 0.2 | 1000 |
| SpotShapeBAR: | 0 | 1000 |
| SpotAvgInten: | 200 | 32767 |
| SpotTotalInten: | ≤4000 (thus not limiting) | 1000000000000 |
| TargetAvgInten: | 0 | 32767 |
| TargetTotalInten: | 0 | 1000000000000 |

Analysis of the Results of the Scan Using vHCS Viewer:

export the results: for each well:

number of valid fields number of objects in each valid field in each of the channels 2, 3 and 4 ("field details")

mean numbers of objects per valid field for each well, in each of the channels 2, 3 and 4 exclude wells with less than 6 valid fields per well from further analysis visually check all photos for any apparent problems, such as bad focusing or obviously inhomogeneous collagen structure ("bubbles", . . . ), . . . ; in case of apparent problems: document, then exclude the corresponding wells from further analysis Further Analysis of the Results of the Invasion Assay (Using e.g. Excel):

For each well, the mean invasion distance was calculated as follows: (25 μm×number of cells at 25 μm+50 μm×number cells at 50 μm)/sum of cells at 0, 25 and 50 μm For all four parameters (number of cells at 0 μm, number of cells at 25 μm, number of cells at 50 μm, mean invasion distance of the counted cells), calculate means, SD and CV of the replicates (n=6 for the controls; n=3 for the samples).

Replicates having a CV≥50% (compound to be re-tested, or assay to be repeated if CV≥50% for the untreated negative control or the compound Y-27632-treated positive control) were invalidated. Y27632 is a selective inhibitor of the Rho-associated protein kinase p160ROCK of the following formula:

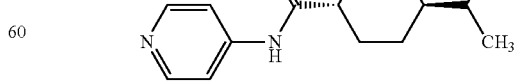

The assay was validated only if the mean invasion distance of the cells treated with 10 μM Y-27632 (positive control) was decreased by ≥40% as compared to the untreated negative control.

Graphs were plotted of all four parameters (number of cells at 0 μm, number of cells at 25 μm, number of cells at 50 μm, mean invasion distance of the counted cells).

Results

Anti-invasive effect at 5 μM on MDA-MB231 breast cancer cells (fold effect compared to 10 μM Y-27632 ref. compound)

| Compound (family) | Invasion of MDA MB231 cells at 5 mM (fold effect of positive control) |
|---|---|
| 148 (Iee) | 0.54 |
| 109 (Ie) | 0.41 |
| 110 (Ie) | 0.64 |
| 112 (Ie) | 0.26 |
| 143 (Iq) | 0.8 |
| 144 (Iq) | 0.73 |
| 63 (Ia) | 0.69 |
| 64 (Ia) | 1.16 |
| 6 (Ia) | 0.63 |
| 18 (Ia) | 0.52 |
| 45 (Ia) | 0.50 |
| 30 (Ia) | 0.33 |
| 35 (Ia) | 0.26 |
| 36 (Ia) | 0.43 |
| 37 (Ia) | 0.34 |
| 48 (Ia) | 0.63 |
| 53 (Ia) | 0.27 |
| 51 (Ia) | 1.06 |
| 52 (Ia) | 0.27 |
| 58 (Ia) | 0.33 |
| 61 (Ia) | 0.34 |
| 58 (Ia) | 0.33 |
| 55 (Ia) | 0.27 |
| 56 (Ia) | 0.26 |

The compounds according to the present invention demonstrated an anti-invasive effect predictive for their activity against cancer.

Therefore, the results of the tests carried out with the compounds described herein demonstrated properties that may be useful to inhibit, prevent and/or treat cancer. For example, the following types of cancers may more be treated by the compounds according to the present invention: colorectal cancer, pancreatic cancer, lung cancer including non-small cell lung cancer, breast cancer, bladder cancer, gall bladder cancer, thyroid cancer, melanoma, liver cancer, uterine/cervical cancer, oesophageal cancer, kidney cancer, ovarian cancer, prostate cancer, head and neck cancer, and stomach cancer, etc.

For this purpose an effective amount of a said compound may be administered to a patient suffering from cancer.

The present disclosure is also related to the use of at least a compound chosen among a compound of anyone of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present invention for the manufacture of a pharmaceutical composition intended for the treatment of cancer.

The present disclosure also encompasses pharmaceutical compositions comprising at least a compound chosen among new compounds of formula (Iq) or (Iee) as defined above and compounds (143), (144), (149), (166) and (167) as defined above or any pharmaceutically acceptable salt thereof.

Thus, these pharmaceutical compositions contain an effective amount of said compound, and one or more pharmaceutical excipients.

The aforementioned excipients are selected according to the dosage form and the desired mode of administration.

In this context, the compounds described herein can be present in any pharmaceutical form suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions, in doses which enable the daily administration of from 0.1 to 1000 mg of active substance.

The present disclosure is also related to the use of a compound of anyone of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above, and compounds (1) to (168) as defined above, or one of its pharmaceutically acceptable salts according to the present invention for the manufacture of a pharmaceutical composition intended for inhibiting, preventing and/or treating cancer.

The present disclosure further relates to a method of treatment of patients suffering form cancer, which comprises at least a step of administration to a patient suffering thereof of an effective amount of a compound of anyone of formula (I), (Ia), (Ib), (Ic), (Id), (Ie), (If), (Ig), (Ih), (Ii), (Ij), (Ik), (Il), (Im), (Io), (Ip), (Iq), (Ir) or (Iee) as defined above and (1) to (168) or one of its pharmaceutically acceptable salts.

What is claimed is:

1. A method of treating breast cancer, pancreatic cancer, prostate cancer, lung cancer, non-small cell lung cancer, thyroid cancer, liver cancer, and kidney cancer, comprising:
    contacting a cell with at least one compound of formula (Ia) or a pharmaceutically acceptable salt thereof:

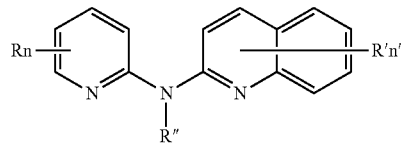

(Ia)

wherein:
R" is a hydrogen atom or a $(C_1-C_4)$alkyl group;
R independently represents a hydrogen atom, a halogen atom, a $(C_1-C_3)$alkyl group, a —CN group, a hydroxyl group, a —$COOR_1$ group, a $(C_1-C_3)$fluoroalkyl group, a —$NO_2$ group, a —$NR_1R_2$ group, or a $(C_1-C_3)$alkoxy group;
R' is a hydrogen atom, a halogen atom, a $(C_1-C_3)$alkyl group, a —$NO_2$ group, a $(C_1-C_3)$alkoxy group, or a —$NR_1R_2$ group; and
$R_1$ and $R_2$ are a hydrogen atom or a $(C_1-C_3)$ alkyl group.

2. The method of claim 1, wherein:
R independently represents a hydrogen atom, a halogen atom, a $(C_1-C_3)$alkyl group, a —CN group, a —$COOR_1$ group, or a $(C_1-C_3)$fluoroalkyl group;
R" is a hydrogen atom or a $(C_1-C_3)$alkyl group; and
R' is a hydrogen atom, a halogen atom or a $(C_1-C_3)$alkyl group.

3. A method of treating breast cancer, pancreatic cancer, prostate cancer, lung cancer, non-small cell lung cancer, thyroid cancer, liver cancer, and kidney cancer, comprising contacting a cell with at least one compound selected from the group consisting of:
    (1) (8-Chloro-quinolin-2-yl)-pyridin-2-yl-amine;
    (2) 2-(Quinolin-2-ylamino)-isonicotinic acid;
    (3) (4-Methyl-pyridin-2-yl)-quinolin-2-yl-amine;
    (4) Pyridin-2-yl-quinolin-2-yl-amine;
    (5) 2-(8-Chloro-quinolin-2-ylamino)-isonicotinic acid;
    (6) (8-Chloro-quinolin-2-yl)-(4-methyl-pyridin-2-yl)-amine;

(7) 6-(Quinolin-2-ylamino)-nicotinonitrile;
(8) Quinolin-2-yl-(4-trifluoromethoxy-phenyl)-amine;
(9) Pyridin-2-yl-quinolin-3-yl-amine;
(10) (3-Methoxy-pyridin-2-yl)-quinolin-3-yl-amine;
(11) Quinolin-3-yl-(5-trifluoromethyl-pyridin-2-yl)-amine;
(12) (5-Nitro-pyridin-2-yl)-quinolin-3-yl-amine;
(13) (5-Methyl-pyridin-2-yl)-quinolin-3-yl-amine;
(14) 2-(Quinolin-3-ylamino)-isonicotinic acid;
(15) Quinolin-6-yl-(5-trifluoromethyl-pyridin-2-yl)-amine;
(16) (6-Methyl-pyridin-2-yl)-quinolin-6-yl-amine;
(17) N-(6-methylpyridin-2-yl)quinolin-2-amine;
(18) 8-chloro-N-(6-methylpyridin-2-yl)quinolin-2-amine;
(19) 4-methyl-N-(pyridin-2-yl)quinolin-2-amine;
(20) 4-methyl-N-(4-methylpyridin-2-yl)quinolin-2-amine;
(21) 3-methyl-N-(4-methylpyridin-2-yl)quinolin-2-amine;
(22) 3-methyl-N-(pyridin-2-yl)quinolin-2-amine;
(23) 6-((4-methylquinolin-2-yl)amino)nicotinonitrile;
(24) 6-((3-methylquinolin-2-yl)amino)nicotinonitrile;
(25) 6-chloro-N-(4-methylpyridin-2-yl)quinolin-2-amine;
(26) 6-chloro-N-(6-methylpyridin-2-yl)quinolin-2-amine;
(27) 4-methyl-N-(5-nitropyridin-2-yl)quinolin-2-amine;
(28) N-(3-nitropyridin-2-yl)quinolin-2-amine;
(29) 8-chloro-N-(3-nitropyridin-2-yl)quinolin-2-amine;
(30) 2-((4-methylquinolin-2-yl)amino)nicotinonitrile;
(31) N-(3-methylpyridin-2-yl)quinolin-2-amine;
(32) N-(5-methylpyridin-2-yl)quinolin-2-amine;
(33) 2-(quinolin-2-ylamino)isonicotinonitrile;
(34) N-(5-(trifluoromethyl)pyridin-2-yl)quinolin-2-amine;
(35) 8-chloro-N-(3-methylpyridin-2-yl)quinolin-2-amine;
(36) 8-chloro-N-(5-methylpyridin-2-yl)quinolin-2-amine;
(37) 8-chloro-N-(5-(trifluoromethyl)pyridin-2-yl)quinolin-2-amine;
(38) N-(3-methoxypyridin-2-yl)quinolin-2-amine;
(39) N-(5-nitropyridin-2-yl)quinolin-2-amine;
(40) 6-((8-chloroquinolin-2-yl)amino)nicotinonitrile;
(41) N-(5-fluoropyridin-2-yl)quinolin-2-amine;
(42) N-(6-(trifluoromethyl)pyridin-2-yl)quinolin-2-amine;
(43) 8-chloro-N-(5-fluoropyridin-2-yl)quinolin-2-amine;
(44) 2-((8-chloroquinolin-2-yl)amino)nicotinic acid;
(45) 4-methyl-N-(6-methylpyridin-2-yl)quinolin-2-amine;
(46) 3-methyl-N-(6-methylpyridin-2-yl)quinolin-2-amine;
(47) 5-cyano-2-(quinolin-2-ylamino)pyridin-1-ium chloride;
(48) 2-((8-chloroquinolin-2-yl)amino)-4-methylpyridin-1-ium chloride;
(49) 8-chloro-N-(4-ethylpyridin-2-yl)quinolin-2-amine;
(50) 8-chloro-N-(6-ethylpyridin-2-yl)quinolin-2-amine;
(51) 8-chloro-N-(4,6-dimethylpyridin-2-yl)quinolin-2-amine;
(52) 6-((8-chloroquinolin-2-yl)amino)-2-methylnicotinonitrile;
(53) 8-chloro-N-(4-chloropyridin-2-yl)quinolin-2-amine;
(54) 8-methyl-N-(4-methylpyridin-2-yl)quinolin-2-amine;
(55) N-(5-bromo-4-methylpyridin-2-yl)-8-chloroquinolin-2-amine;
(56) 8-chloro-N-(3-ethyl-6-methylpyridin-2-yl)quinolin-2-amine;
(57) 8-fluoro-N-(4-methylpyridin-2-yl)quinolin-2-amine;
(58) 8-bromo-N-(4-methylpyridin-2-yl)quinolin-2-amine;
(59) methyl 6-(quinolin-2-ylamino)nicotinate;
(60) methyl 6-[(8-chloroquinolin-2-yl)amino]pyridine-3-carboxylate;
(61) methyl 6-[(3-methylquinolin-2-yl)amino]pyridine-3-carboxylate;
(62) methyl 2-[(8-chloroquinolin-2-yl)amino]pyridine-3-carboxylate;
(63) 8-methoxy-N-(4-methylpyridin-2-yl)quinolin-2-amine;
(64) N-(4-methylpyridin-2-yl)-5-nitroquinolin-2-amine;
(65) 2-N-(4-methylpyridin-2-yl)quinoline-2,8-diamine;
(66) N-(4-methylpyridin-2-yl)-5-aminoquinolin-2-amine;
(67) methyl 6-[(4-methylquinolin-2-yl)amino]pyridine-3-carboxylate;
(68) 8-chloro-N-[4-(trifluoromethyl)pyridin-2-yl]quinolin-2-amine;
(69) 2-[(8-chloroquinolin-2-yl)amino]pyridin-3-ol;
(70) 8-chloro-N-[6-(trifluoromethyl)pyridin-2-yl]quinolin-2-amine;
(71) 6-chloro-N-(5-fluoropyridin-2-yl)quinolin-2-amine;
(72) N-(6-ethylpyridin-2-yl)-3-methylquinolin-2-amine;
(73) N-(5-fluoropyridin-2-yl)-3-methylquinolin-2-amine;
(74) 3-methyl-N-[5-(trifluoromethyl)pyridin-2-yl]quinolin-2-amine;
(75) 4-N-(8-chloroquinolin-2-yl)-1-N,1-N-dimethylbenzene-1,4-diamine;
(76) N-(4-methoxyphenyl)quinolin-2-amine;
(77) 8-chloro-N-(4-methoxyphenyl)quinolin-2-amine;
(78) 4-methyl-N-[4-(trifluoromethoxy)phenyl]quinolin-2-amine;
(79) N-(4-methoxyphenyl)-3-methylquinolin-2-amine;
(80) 3-methyl-N-[4-(trifluoromethoxy)phenyl]quinolin-2-amine;
(81) 1-N,1-N-dimethyl-4-N-(3-methylquinolin-2-yl)benzene-1,4-diamine;
(82) N-[2-methyl-4-(trifluoromethoxy)phenyl]quinolin-2-amine;
(83) N-[3-(trifluoromethoxy)phenyl]quinolin-2-amine;
(84) N-[2-(trifluoromethoxy)phenyl]quinolin-2-amine;
(85) N-(4-nitrophenyl)quinolin-2-amine;
(86) N-(3-fluorophenyl)quinolin-2-amine;
(87) 8-chloro-N-[3-(trifluoromethoxy)phenyl]quinolin-2-amine;
(88) 8-chloro-N-(3-fluorophenyl)quinolin-2-amine;
(89) 2-{[4-(trifluoromethoxy)phenyl]amino}quinolin-1-ium chloride;
(90) 8-chloro-N-[4-(trifluoromethoxy)phenyl]quinolin-2-amine;
(91) 3-methyl-N-[2-methyl-4-(trifluoromethoxy)phenyl]quinolin-2-amine;
(92) 3-methyl-N-[3-(trifluoromethoxy)phenyl]quinolin-2-amine;
(93) 3-methyl-N-[2-(trifluoromethoxy)phenyl]quinolin-2-amine;
(94) 8-chloro-N-[2-methyl-4-(trifluoromethoxy)phenyl]quinolin-2-amine;
(95) 3-methyl-2-{[4-(trifluoromethoxy)phenyl]amino}quinolin-1-ium chloride;
(96) 6-chloro-N-(4-(trifluoromethoxy)phenyl)quinolin-2-amine;
(97) 4-methyl-2-{[4-(trifluoromethoxy)phenyl]amino}quinolin-1-ium chloride;
(98) 8-bromo-N-[4-(trifluoromethoxy)phenyl]quinolin-2-amine;
(99) 8-fluoro-N-[4-(trifluoromethoxy)phenyl]quinolin-2-amine;

(100) 8-methyl-N-[4-(trifluoromethoxy)phenyl]quinolin-2-amine;
(101) N-(4-butoxyphenyl)-8-chloroquinolin-2-amine;
(102) N-(4-phenoxyphenyl)quinolin-2-amine;
(103) 8-methoxy-N-[4-(trifluoromethoxy)phenyl]quinolin-2-amine;
(104) 8-chloro-N-[3-chloro-4-(trifluoromethoxy)phenyl]quinolin-2-amine;
(105) N-(6-methylpyridin-2-yl)quinolin-3-amine;
(106) N-(3-nitropyridin-2-yl)quinolin-3-amine;
(107) N-(5-methylpyridin-2-yl)quinolin-6-amine;
(108) N-(3-methoxypyridin-2-yl)quinolin-6-amine;
(109) 6-chloro-N-(pyrazin-2-yl)quinolin-2-amine;
(110) 8-bromo-N-(pyrazin-2-yl)quinolin-2-amine;
(111) 8-methyl-N-(pyrazin-2-yl)quinolin-2-amine;
(112) 8-chloro-N-(pyrazin-2-yl)quinolin-2-amine;
(113) N-(pyrazin-2-yl)quinolin-2-amine;
(114) 4-methyl-N-(pyrazin-2-yl)quinolin-2-amine;
(115) 3-methyl-N-(pyrazin-2-yl)quinolin-2-amine;
(116) 8-fluoro-N-(pyrazin-2-yl)quinolin-2-amine;
(117) 8-methoxy-N-(pyrazin-2-yl)quinolin-2-amine;
(118) N-(pyridin-3-yl)quinolin-3-amine;
(119) 8-chloro-N-(pyridin-4-yl)quinolin-2-amine;
(120) N-(pyridin-4-yl)quinolin-2-amine;
(121) N-(pyridin-4-yl)quinolin-3-amine;
(122) N-[4-(trifluoromethoxy)phenyl]quinolin-3-amine;
(123) N-(4-methoxyphenyl)quinolin-3-amine;
(124) N-[4-(trifluoromethoxy)phenyl]quinoxalin-2-amine;
(125) N-[2-methyl-4-(trifluoromethoxy)phenyl]quinoxalin-2-amine;
(126) N-[3-(trifluoromethoxy)phenyl]quinoxalin-2-amine;
(127) N-[2-(trifluoromethoxy)phenyl]quinoxalin-2-amine;
(128) N-(pyrimidin-2-yl)quinolin-2-amine;
(129) 8-chloro-N-(pyrimidin-2-yl)quinolin-2-amine;
(130) 4-methyl-N-(pyrimidin-2-yl)quinolin-2-amine;
(131) N-(pyrazin-2-yl)quinolin-6-amine;
(132) N-(pyrazin-2-yl)quinolin-3-amine;
(133) 6-methyl-N-(naphthalen-2-yl)pyridin-2-amine;
(134) N-(naphthalen-2-yl)pyridin-2-amine;
(135) N-(pyridin-2-yl)quinoxalin-2-amine;
(136) N-(4-methylpyridin-2-yl)quinoxalin-2-amine;
(137) 6-(quinoxalin-2-ylamino)pyridine-3-carbonitrile;
(138) N-(6-methylpyridin-2-yl)quinoxalin-2-amine;
(139) N-(4-methylpyridin-2-yl)-3-(trifluoromethyl)quinoxalin-2-amine;
(140) N-(3,5-dichloro-4-methylpyridin-2-yl)quinoxalin-2-amine;
(141) N-(4-methyl-3-nitropyridin-2-yl)quinoxalin-2-amine;
(142) N-(pyrimidin-2-yl)quinoxalin-2-amine;
(143) 4-N,4-N-dimethyl-7-N-[4-(trifluoromethoxy)phenyl]quinoline-4,7-diamine;
(144) 4-(morpholin-4-yl)-N-[4-(trifluoromethoxy)phenyl]quinolin-7-amine;
(145) 4-methoxy-N-(pyridin-2-yl)quinolin-7-amine;
(146) 4-methoxy-N-(4-methylpyridin-2-yl)quinolin-7-amine;
(147) 4-N,4-N-dimethyl-7-N-(4-methylpyridin-2-yl)quinoline-4,7-diamine;
(148) 5,8-dimethyl-N-(5-methylpyridin-2-yl)isoquinolin-6-amine;
(149) 5,8-dimethyl-N-(5-trifluoromethylpyridin-2-yl)isoquinolin-6-amine;
(150) N-(4-methylpyridin-2-yl)-8-nitroquinolin-2-amine;
(151) 6-chloro-N-(6-ethylpyridin-2-yl)quinolin-2-amine;
(152) 6-chloro-N-(5-methylpyridin-2-yl)quinolin-2-amine;
(153) 6-chloro-N-[5-(trifluoromethyl)pyridin-2-yl]quinolin-2-amine;
(154) N2-(8-chloroquinolin-2-yl)-4-methylpyridine-2,3-diamine;
(155) N-(4-butoxyphenyl)-3-methylquinolin-2-amine;
(156) 4-N-(6-chloroquinolin-2-yl)-1-N,1-N-dimethylbenzene-1,4-diamine;
(157) 8-chloro-N-(3-chloro-4-methoxyphenyl)quinolin-2-amine;
(158) N1-(8-chloroquinolin-2-yl)-4-(trifluoromethoxy)benzene-1,2-diamine;
(159) N-(3-aminopyridin-2-yl)quinolin-3-amine;
(160) 6-chloro-N-(4-methylpyridin-2-yl)quinoxalin-2-amine;
(161) N-(4-ethylpyridin-2-yl)quinoxalin-2-amine;
(162) N-(5-bromo-4-methylpyridin-2-yl)quinoxalin-2-amine;
(163) N-(4,6-dimethylpyridin-2-yl)quinoxalin-2-amine;
(164) [2-(quinoxalin-2-ylamino)pyridin-4-yl]methanol;
(165) N-(4-methyl-5-nitropyridin-2-yl)quinoxalin-2-amine;
(166) N-(4-methoxyphenyl)-4-(4-methylpiperazin-1-yl)quinolin-7-amine;
(167) 4-methoxy-N-[4-(trifluoromethoxy)phenyl]quinolin-7-amine;
(168) N-(4-methylpyridin-2-yl)-4-(morpholin-4-yl)quinolin-7-amine; and pharmaceutically acceptable salts thereof.

4. The method of claim 3, wherein:
the compound is selected from the group consisting of compounds (1), (2), (5)-(7), (10)-(16), (18), (21)-(44), (46)-(74), (105)-(108), (124)-(130), (135)-(141), (145)-(147), (150)-(154), (159), (160)-(165), (168), and their pharmaceutically acceptable salts; and
the pharmaceutically acceptable salts are hydrobromide, tartrate, citrate, trifluoroacetate, ascorbate, hydrochloride, tartrate, triflate, maleate, mesylate, formate, acetate, and fumarate.

5. The method of claim 1, wherein the compound is in a pharmaceutical composition.

6. The method of claim 4, wherein the compound is in a pharmaceutical composition.

7. The method of claim 1, further comprising a step of administering the compound to a patient in need of cancer treatment.

8. The method of claim 7, wherein the compound is administered to the patient orally.

9. The method of claim 3, further comprising a step of administering the compound to a patient in need of cancer treatment.

10. The method of claim 9, wherein the compound is administered to the patient orally.

* * * * *